(12) United States Patent
Jia et al.

(10) Patent No.: US 10,611,762 B2
(45) Date of Patent: Apr. 7, 2020

(54) CRYSTALLINE FORMS OF A FGFR INHIBITOR AND PROCESSES FOR PREPARING THE SAME

(71) Applicant: Incyte Corporation, Wilmington, DE (US)

(72) Inventors: Zhongjiang Jia, Kennett Square, PA (US); Qun Li, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/989,414

(22) Filed: May 25, 2018

(65) Prior Publication Data
US 2019/0055237 A1    Feb. 21, 2019

Related U.S. Application Data

(60) Provisional application No. 62/511,525, filed on May 26, 2017.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .......................... C07D 471/04; C07B 2200/13
USPC ........................................................ 514/300
See application file for complete search history.

(56) References Cited

U.S. PATENT DOCUMENTS

| | | |
|---|---|---|
| 850,370 A | 4/1907 | Hynes |
| 3,894,021 A | 7/1975 | Denzel et al. |
| 4,271,074 A | 6/1981 | Lohmann et al. |
| 4,339,267 A | 7/1982 | Levitt |
| 4,347,348 A | 8/1982 | Chernikhov et al. |
| 4,402,878 A | 9/1983 | D'Alelio et al. |
| 4,405,519 A | 9/1983 | D'Alelio et al. |
| 4,405,520 A | 9/1983 | D'Alelio et al. |
| 4,405,786 A | 9/1983 | D'Alelio et al. |
| 4,460,773 A | 7/1984 | Suzuki et al. |
| 4,874,803 A | 10/1989 | Baron et al. |
| 4,940,705 A | 7/1990 | Boshagen et al. |
| 5,159,054 A | 10/1992 | Keller |
| 5,240,941 A | 8/1993 | Bruneau |
| 5,480,887 A | 1/1996 | Hornback et al. |
| 5,536,725 A | 7/1996 | Cullen et al. |
| 5,541,324 A | 7/1996 | TenBrink et al. |

(Continued)

FOREIGN PATENT DOCUMENTS

| | | |
|---|---|---|
| CL | 201702117 | 6/2018 |
| CN | 1863774 | 11/2006 |

(Continued)

OTHER PUBLICATIONS

ICH harmonized tripartite guideline , ICH (Year: 1999).*

(Continued)

*Primary Examiner* — Rita J Desai
(74) *Attorney, Agent, or Firm* — Fish & Richardson P.C.

(57) ABSTRACT

The present disclosure relates to solid forms of N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide, methods of preparation thereof, and intermediates in the preparation thereof, which are useful in the treatment of the FGFR-associated or mediated diseases such as cancer.

67 Claims, 29 Drawing Sheets

Specification includes a Sequence Listing.

(56) References Cited

U.S. PATENT DOCUMENTS

| | | |
|---|---|---|
| 5,783,577 A | 7/1998 | Houghten et al. |
| 5,845,025 A | 12/1998 | Garito et al. |
| 5,994,364 A | 11/1999 | Njoroge et al. |
| 6,465,484 B1 | 10/2002 | Bilodeau et al. |
| 6,998,408 B2 | 2/2006 | Pinto |
| 7,074,801 B1 | 7/2006 | Yoshida et al. |
| 7,125,880 B1 | 10/2006 | Chen |
| 7,618,975 B2 | 11/2009 | Cai et al. |
| 7,642,255 B2 | 1/2010 | Sim |
| 8,754,114 B2 | 6/2014 | Yao et al. |
| 8,889,711 B2 | 11/2014 | Bedjeguelal |
| 9,266,892 B2 | 2/2016 | Zhuo et al. |
| 9,388,185 B2 | 7/2016 | Lu et al. |
| 9,533,954 B2 | 1/2017 | Yao et al. |
| 9,533,984 B2 | 1/2017 | Sun et al. |
| 9,580,423 B2 | 2/2017 | Lu et al. |
| 9,611,267 B2 | 4/2017 | Wu et al. |
| 9,708,318 B2 | 7/2017 | Lu et al. |
| 9,745,311 B2 | 8/2017 | Lu et al. |
| 9,801,889 B2 | 10/2017 | Lu et al. |
| 9,890,156 B2 * | 2/2018 | Lu .............. C07D 471/04 |
| 10,016,348 B2 | 7/2018 | Lu et al. |
| 10,040,790 B2 | 8/2018 | Sun et al. |
| 10,131,667 B2 | 11/2018 | Wu et al. |
| 10,213,427 B2 | 2/2019 | Yao et al. |
| 10,214,528 B2 * | 2/2019 | Lu .............. C07D 471/04 |
| 10,251,892 B2 | 4/2019 | Sokolsky et al. |
| 2003/0078255 A1 | 4/2003 | Pinto |
| 2003/0078277 A1 | 4/2003 | Hibi et al. |
| 2003/0181622 A1 | 9/2003 | Chiu et al. |
| 2004/0044012 A1 | 3/2004 | Dobrusin et al. |
| 2004/0067948 A1 | 4/2004 | Hallett |
| 2004/0097493 A1 | 5/2004 | Chen et al. |
| 2004/0122029 A1 | 6/2004 | Liu et al. |
| 2004/0204427 A1 | 10/2004 | Chen et al. |
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0280943 A1 | 12/2007 | Friedman et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0243308 A1 | 8/2014 | Yao et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |
| 2016/0280713 A1 | 9/2016 | Lu et al. |
| 2017/0107216 A1 | 4/2017 | Wu et al. |
| 2017/0119782 A1 | 5/2017 | Lu et al. |
| 2017/0137424 A1 | 5/2017 | Wu et al. |
| 2017/0145025 A1 | 5/2017 | Li et al. |
| 2017/0165263 A1 | 6/2017 | Yao et al. |
| 2017/0166564 A1 | 6/2017 | Sun et al. |
| 2017/0174671 A1 | 6/2017 | Wu et al. |
| 2017/0174679 A1 | 6/2017 | Lajkiewicz et al. |
| 2017/0290839 A1 | 10/2017 | Lu et al. |
| 2017/0320875 A1 | 11/2017 | Li et al. |
| 2017/0320877 A1 | 11/2017 | Wu et al. |
| 2017/0342060 A1 | 11/2017 | Lu et al. |
| 2017/0362253 A1 | 12/2017 | Xiao et al. |
| 2018/0008610 A1 | 1/2018 | Lu et al. |
| 2018/0016260 A1 | 1/2018 | Yu et al. |
| 2018/0244672 A1 | 8/2018 | Lu et al. |
| 2019/0062327 A1 | 2/2019 | Sun et al. |
| 2019/0127376 A1 | 5/2019 | Wu et al. |
| 2019/0240220 A1 | 8/2019 | Yao et al. |
| 2019/0241560 A1 | 8/2019 | Lu et al. |

FOREIGN PATENT DOCUMENTS

| | | |
|---|---|---|
| CN | 101007778 | 8/2007 |
| CN | 102399220 | 4/2012 |
| CN | 102399233 | 4/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S6310630 | 1/1988 |
| JP | 02009895 | 1/1990 |
| JP | H0348656 | 3/1991 |
| JP | H03275669 | 12/1991 |
| JP | 04179576 | 6/1992 |
| JP | H04158084 | 6/1992 |
| JP | H04328121 | 11/1992 |

(56) References Cited

FOREIGN PATENT DOCUMENTS

| | | |
|---|---|---|
| JP | H05320173 | 12/1993 |
| JP | H05320515 | 12/1993 |
| JP | H09188812 | 7/1997 |
| JP | H1060426 | 3/1998 |
| JP | H11171865 | 6/1999 |
| JP | 2000123973 | 4/2000 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 200628027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 20119348 | 1/2011 |
| JP | 201144637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 201349251 | 3/2013 |
| JP | 2013179181 | 9/2013 |
| JP | 2015517376 | 6/2015 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/24744 | 5/2000 |
| WO | WO 2000/68186 | 11/2000 |
| WO | WO 2001/02369 | 1/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/037891 | 5/2003 |
| WO | WO 2003/040131 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099818 | 12/2003 |
| WO | WO 2003/101985 | 12/2003 |
| WO | WO 2004/002986 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056822 | 7/2004 |
| WO | WO 2004/056830 | 7/2004 |
| WO | WO 2004/065378 | 8/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/040119 | 5/2005 |
| WO | WO 2005/047289 | 5/2005 |
| WO | WO 2005/056524 | 6/2005 |

(56) References Cited

FOREIGN PATENT DOCUMENTS

| | | |
|---|---|---|
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |

(56) References Cited

FOREIGN PATENT DOCUMENTS

| | | |
|---|---|---|
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |

(56) References Cited

FOREIGN PATENT DOCUMENTS

| | | |
|---|---|---|
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/049352 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/174307 | 10/2014 |
| WO | WO-2014172644 A2 * 10/2014 ........... C07D 471/04 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |
| WO | WO-2016134314 A1 * 8/2016 ........... C07D 471/04 |

OTHER PUBLICATIONS

Australian Office Action in Australian Application No. 2018208772, dated Jul. 1, 2018, 5 pages.

Australian Office Action in Australian Application No. 2016219822, dated Jul. 8, 2019, 4 pages.

Chilean Office Action in Chilean Application No. 2122-2017, dated Apr. 22, 2019, 25 pages.

Costa Rican Office Action in Costa Rican Application No. 2014-0577, dated Jun. 13, 2019, 17 pages.

(56) References Cited

OTHER PUBLICATIONS

Desnoyers et al., "Targeting FGF19 inhibits tumor growth in colon cancer xenograft and FGF19 transgenic hepatocellular carcinoma models," Oncogene, 2008, 27:85-97.
Ding et al., "Somatic mutations affect key pathways in lung adenocarcinoma," Nature., Oct. 23, 2008, 455:1069-1075.
Heinzle C, et al., "Differential Effects of Polymorphic Alleles of FGF Receptor 4 on Colon Cancer Growth and Metastasis," Cancer Research, Nov. 2012, 72(22):5767-5777.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Japanese Office Action in Japanese Application No. 2018-228352, dated Aug. 20, 2019, 6 pages.
Marks et al., "Mutational Analysis of EGFR and Related Signaling Pathway Genes in Lung Adenocarcinomas Identifies a Novel Somatic Kinase Domain Mutation in FGFR4," PLoS ONE, May 9, 2007, 2:e426.
Philippine Office Action in Philippine Application No. 1/2015/502383, dated Jul. 8, 2019, 7 pages.
Seitzer et al., "A single nucleotide change in the mouse genome accelerates breast cancer progression," Cancer Res., Jan. 2010, 70(2):802-812.
Tang et al., "Role of fibroblast growth factor receptor 4 in cancer," Cancer Science, Oct. 2018, 109(10):3024-3031.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Turkington et al., "Fibroblast growth factor receptor 4 (FGFR4): a targetable regulator of drug resistance in colorectal cancer," Cell Death Dis., Feb. 6, 2014, 5:e1046.
Wang et al., "The fibroblast growth factor receptor-4 Arg388 allele is associated with prostate cancer initiation and progression," Clin Cancer Res. 2004, 10:6169-6178.
Yu et al., "FGFR-4 Arg(3)(8)(8) enhances prostate cancer progression via extracellular signal-related kinase and serum response factor signaling," Clin Cancer Res., Jul. 2011, 17:4355-4366.
Ying et al., "Genome-wide screening for genetic alterations in esophageal cancer by aCGH identifies 11q13 amplification oncogenes associated with nodal metastasis," PLoS One, Jun. 25, 2012, 7:e39797.
"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Arai et al., "Characterization of the cell or origin and propagation potential of the fibroblast growth factor 9-induced mouse model of lung adenocarcinoma," J. Pathol., Mar. 2015, 235(4): 593-605.

Ash and Ash, "Handbook of Pharmaceutical Additives," Gower Publishing Company, 2007, 3rd ed.
Australian Office Action in Australian Application No. 2013287176, dated Sep. 12, 2017, 4 pages.
Australian Office Action in Australian Application No. 2014253798, dated Jul. 31, 2017, 4 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 66(2):1-19 (1977).
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R )-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J. Combi Chem., 5, 670 (2003).
Blom et al., Preparative LC-MS Purification: Improved Compound Specific Method Optimization, J. Combi. Chem. 2004, 6(6), 874-883.
Blom, K., "Two-Pump at Column Dilution Configuration for Preparative LC-MS", J. Combi Chem., 4, 295 (2002).
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.

(56) References Cited

OTHER PUBLICATIONS

Bono et al., "Inhibition of Tumor Angiogenesis and Growth by a Small-Molecule Multi-FGF Receptor Blocker with Allosteric Properties," Cancer Cell, Apr. 2013, 477-488.
Brooks et al., "Fibroblast growth factor signaling: a new therapeutic opportunity in cancer," Clinical Cancer Research, 2012, 1-23.
Cancer [online], [retrieved on Jul. 6, 2007] Retrieved from the Internet, URL: http://www.nlm.nih.gov/medlineplus/cancer.html.
Cappellen et al., "Frequent activating mutations of FGFR3 in human bladder and cervix.carcinomas," Nature Genetics, Sep. 1999, 23: 18-20.
Capelletti et al., "Identification of Recurrent FGFR3-TACC3 Fusion Oncogenes from Lung Adenocarcinoma," AACR Journals, 2014, 6551-6558.
Carmichael et al., "Familial Tumoral Calcinosis: A Forty-Year Follow-up on One Family," The Journal of Bone & Joint Surgery, 2009, 664-671.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," PLOS ONE, Aug. 2015, 23 pages.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 2015-003089, dated Apr. 24, 2017, 13 pages (English Summary).
Chilean Office Action in Chilean Application No. 3355-2014, dated Jan. 18, 2017, 17 pages (with English translation).
Chilean Opposition in Chilean Application No. 3355-2014, 3 pages (English translation only).
Chilean Office Action in Chilean Application No. 2015-003089, dated Jan. 23, 2018, 8 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Cole et al "Inhibition of FGFR2 and FGFR1 increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Columbian Office Action in Columbian Application No. 14-275934-6, dated May 31, 2016, 3 pages (English translation only).
Columbian Office Action in Columbian Application No. 14-275934-6, dated Nov. 17, 2015, 12 pages (English translation only).
Columbian Office Action in Columbian Application No. 16100866, dated Aug. 10, 2017, 9 pages.
Columbian Office Action in Columbian Application No. NC2017/0008795, dated Aug. 29, 2017, 2 pages.
Columbian Office Action in Columbian Application No. NC2017/0008795, dated Nov. 29, 2018, 8 pages.
Columbian Office Action in Columbian Application No. NC2017/0008824, dated Aug. 31, 2017, 3 pages.
Columbian Office Action in Columbian Application No. NC2017/0008824, dated Nov. 29, 2018, 8 pages.
Corre et al., "Synthesis and biological evaluation of a triazole-based library of pyrido [2,3-d]pyrimidines as FGFR3 tyrosine kinase inhibitors," Organic & Biomolecular Chemistry, 2010, 8:2164-2173.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Eissa, "Synthesis and evaluation of some surface active agents from long chain fatty amine," Spanish National Research Council, Jan. 2007, 58(4):379-389.

(56) References Cited

OTHER PUBLICATIONS

Elsheikh et al., "FGFR1 amplification in breast carcinomas: a chromogenic in situ hybridisation analysis," Breast Cancer Research, Mar. 2007, 9(2): 1-12.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.
European Communication pursuant to Article 94(3) EPC in European Application No. 13783125.1, dated Jan. 26, 2016, 4 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Faul et al., "FGF23 induces left ventricular hypertrophy," The Journal of Clinical Investigation, 2010, 1-16.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cel lung cancer cells: therapeutic implications and synergism with epidermal growth factor receptor inhibition," Mol Cancer Therapy, 2008, 3408-3419.
French et al., "Targeting FGFR4 Inhibits Hepatocellular Carcinoma in Preclinical Mouse Models," PLoS ONE, 2012, 7(5):e36713, 1-12.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fukumoto and Yamashita, "FGF23 is a hormone-regulating phophate metabolism—Unique biological characteristics of FGF23," Bone, 2007, 1190-1195.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297:282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gerby et al., "2-Arylidenedihydroindole-3-ones: Design, synthesis, and biological activity on bladder carcinoma cell lines," Bioorganic & Medicinal Chemistry Letters, 2007, 208-213.

Ghorab et al., "Synthesis of some sulfur containing Tetrahydrobenzoabuthieno[b] Thieno(Pyridines, Quinolines, Oxazins and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed.
Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999).
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindolebased indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Hackam, et al. JAMA, 296(14), 2006, 1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinzle et al., "Is fibroblast growth factor receptor 4 a suitable target of cancer therapy?," Cur. Pharm. Des. 2014, 20:2881-98.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 259-267.
Hideshima and Anderson, "Preclinical Studies of Novel Targeted Therapies," Hematol Oncol Clin N Am, 2007, 1071-1091.

(56) References Cited

OTHER PUBLICATIONS

Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
Ichikawa et al., "A homozygous missense mutation in human KLOTHO causes severe tumoral.calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Inokuchi et al., "Therapeutic targeting of fibroblast growth factor receptors in gastric cancer," Gastroenterol Res Pract., Apr. 27, 2015, 2015:796380, 8 pages.
International Preliminary Report on Patentability and Written Opinion in International Application No. PCT/US2011/066473, dated Jun. 25, 2013, 10 pages.
International Preliminary Report on Patentability in International Application No. PCT/US2013/045309, dated Dec. 24, 2014, 11 pages.
International Preliminary Report on Patentability in International Application No. PCT/US2013/054361, dated Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Search Report and Written Opinion for International Application No. PCT/US2015/056583, dated Dec. 15, 2015, 10 pages.
International Search Report and Written Opinion in International Application No. PCT/US2013/045309, dated Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, dated Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report dated Jun. 19, 2012 for International Application No. PCT/US2011/066473 (15 pgs.).
International Search Report and Written Opinion in International Application No. PCT/US2018/034559, dated Mar. 8, 2019, 14 pages.
Invitation to Pay Additional Fees and, Where Applicable, Protest Fee in International Application No. PCT/US2013/045309, dated Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Jebar et al., "FGFR3 and RAS gene mutations are mutually exclusive genetic events in urothelial cell carcinoma," Oncogene, 2005, 24: 5218-5225.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, V.C. Nature Reviews: Drug Discovery, 2, 2003, 205.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.

(56) References Cited

OTHER PUBLICATIONS

Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Pammeteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido [2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.

L'Hote and Knowles, "Cell responses to FGFR3 signalling: growth, differentiation and apoptosis," Experimental Cell Research, 2005, 417-431.
Li et al., "Compound deletion of FGFR3 and FGFR4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of FGF23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5): 2115-2123.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martino et al., "Mutant fibroblast growth factor receptor 3 induces intracellular signaling and cellular transformation in a cell type- and mutation-specific manner," Oncogene, 2009, 28: 4306-4316.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Miyake et al., "1-tert-Butyl-3-[6-(3,5-dimethoxy-phenyl)-2-(4-diethylamino-butylamino)-pyrido[2,3-d]pyrimidin-7-yl-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain" The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.

(56) References Cited

OTHER PUBLICATIONS

Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)-mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
New Zealand Office Action in New Zealand Application No. 743274, dated Jul. 19, 2018, 5 pages.
New Zealand Examination Report in New Zealand Application No. 743274, dated Jul. 18, 2018, 4 pages.
New Zealand Office Action in New Zealand Application No. 702747, dated Sep. 16, 2016, 3 pages.
New Zealand Office Action in New Zealand Application No. 702747, dated Mar. 8, 2019, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth in vitro and in vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington's Pharmaceutical Sciences, 17th ed., Mack Publishing Company, Easton, Pa., 1985, p. 1418.
Remington, "The Science and Practice of Pharmacy," Lippincott Williams & Wilkins, 2005, 21st edition.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/ fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Rowe et al., "Handbook of Pharmaceutical Excipients," The Pharmaceutical Press and the American Pharmaceutical Association, 2009, 6th Edition, Front Matter only, 8 pages.
Ryan et al., "Toxicologic Pathology of Unique Biotechnology Agents and Biotherapies," Toxicologic Pathology, 1999, 27(1): 78-86.

(56) References Cited

OTHER PUBLICATIONS

Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Segev et al., "Restrained chondrocyte proliferation and maturation with abnormal growth plate vascularization and ossification in human FRFR-3$^{G380R}$ trasngenic mice," Human Molecular Genetics, 2000, 9(2): 249-258.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgical Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptro 3-lllc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.

Squires et al., "Development of inhibitors of the fibroblast growth factor receptor (FGFR) kinase using a fragment based approach," Cancer Res, 2008, 1 page.
Sun et al., "Design, Synthesis, and Evaluations of Substituted 3-[3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Tan et al., "Development of covalent inhibitors that can overcome resistance to first-generation FGFR kinase inhibitors," PNAS, Oct. 2014, E4869-E4877.
Taylor et al., "Identification of FGFR4-activating mutations in human rhabdomyasarcomas that promote metastasis in xenotransplanted models," J Clin Invest, Nov. 2009, 119(11): 3395-407.
Taylor, "Inhibitor PD-173074 Bound to the Tyrosine Kinase Domain of FGFR 1," Molecular & Behavioral Neuroscience Institute, Feb. 2006, 1 page.
Taylor, "Inhibitor SU-5402 Bound to the Tyrosine Kinase Domain of FGFR 1," Molecular & Behavioral Neuroscience Institute, Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
Thome and Weil, "Post-translational modifications regulate distinct functions of CARMA1 and BCL10," TRENDS in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.

(56) References Cited

OTHER PUBLICATIONS

Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Vietnamese Office Action in Vietnamese Application No. 1-2015-00102, dated Mar. 18, 2015, 4 pages.
Von Massenhausen et al., "Evaluation of FGFR3 as a Therapeutic Target in Head and Neck Squamous Cell Carcinoma," Targ. Oncol., 2016, 11: 631-642.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Wu, "Urothelial Tumorigenesis: A Tale of Divergent Pathways," Nature Reviews, Sep. 2005, 5: 713-725.

Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in a Newly Developed Fibroblast Growth Factor Receptor 3—Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Yu et al., "Analysis of the Biochemical Mechanisms for the Endocrine Actions of Firbroblast Growth Factor-23," Endocrinology, Nov. 2005, 146(11): 4647-4656.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
Malaysian Office Action in Malaysian Application No. 2014003396, dated Dec. 15, 2017, 4 pages.
Mexican Office Action in Mexican Application No. MX/a/2014/015192, dated Jan. 24, 2018, 6 pages.
Japanese Office Action in Japanese Application No. 2016-509131, dated Feb. 20, 2018, 5 pages (English Translation).
Eurasian Office Action in Eurasian Application No. 201791866, dated Feb. 19, 2018, 10 pages (English Translation).
Eurasian Office Action in Eurasian Application No. 201590005, dated Mar. 28, 2018, 6 pages.
Taiwan Office Action in Taiwan Application No. 103114284, dated Apr. 9, 2018, 4 pages (English Search Report).
Chinese Office Action in Chinese Application No. 201480028858.7, dated Apr. 4, 2018, 10 pages (English Translation).

(56) References Cited

OTHER PUBLICATIONS

Eurasian Office Action in Eurasian Application No. 201791867, dated Apr. 4, 2018, 4 pages (English Translation).
Indonesian Office Action in Indonesian Application No. P00201507153, dated Apr. 27, 2018, 5 pages (English Translation).
Williams et al., "Oncogenic FGFR3 gene fusions in bladder cancer," Hum Mol Genet, 2013, 22:795-803.
The Cancer Genome Atlas Research Network, "Comprehensive molecular characterization of urothelial bladder carcinoma," Nature, 2014, 507: 315-22.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Zhang et al., "Enhanced FGFR signaling predisposes pancreatic cancer to the effect of a potent FGFR inhibitor in preclinical models," British Journal of Cancer, 2014, 110: 320-329.
Peruvian Office Action in Peruvian Application No. 2433, dated Nov. 27, 2018, 13 pages.
Chinese Office Action in Chinese Application No. 201710874686.0, dated Feb. 25, 2019, 17 pages.
Chinese Office Action in Chinese Application No. 201710395346.X, dated Jan. 22, 2019, 17 pages.
Indian Office Action in Indian Application No. 9781/DELNP/2015, dated Jan. 18, 2019, 6 pages.

\* cited by examiner

CRYSTALLINE FORMS OF A FGFR INHIBITOR AND PROCESSES FOR PREPARING THE SAME

FIELD OF THE INVENTION

This application relates to crystalline forms of a Fibroblast Growth Factor Receptors (FGFR) inhibitor, including methods of preparation thereof, and intermediates in the preparation thereof, which are useful in the treatment of FGFR mediated disease such as cancer.

BACKGROUND OF THE INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes. The FGFR4-FGF19 signaling axis, specifically, has been implicated in the pathogenesis of a number of cancers including hepatocellular carcinoma (Heinzle et al., Cur. Pharm. Des. 2014, 20:2881). Ectopic expression of FGF19 in transgenic mice was shown to lead to tumor formation in the liver and a neutralizing antibody to FGF19 was found to inhibit tumor growth in mice. In addition, overexpression of FGFR4 has been observed in a multiple tumor types including hepatocellular carcinoma, colorectal, breast, pancreatic, prostate, lung, and thyroid cancers. Furthermore, activating mutations in FGFR4 have been reported in rhabdomyosarcoma (Taylor et al. JCI 2009, 119:3395).

Inhibitors of FGFR are currently being developed for the treatment of cancer. For example, the molecule N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide and other small molecule inhibitors of FGFR are reported in e.g., US Publication Nos.: 2012/0165305; 2014-0045814; 2013-0338134; 2014/0171405; 2014/0315902; 2016/0115164; 2016/0244448; 2016/0244449; and 2016-0244450. Accordingly, there is a need for new forms of FGFR-inhibiting molecules for preparing pharmaceutically useful formulations and dosage forms with suitable properties related to, for example, facilitating the manufacture of safe, effective, and high quality drug products.

SUMMARY OF THE INVENTION

Provided herein are solid forms of N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide, or salts thereof.

Provided herein are also pharmaceutical compositions, which include the solid forms (e.g., crystalline forms) as described herein, and one or more pharmaceutically acceptable carriers or excipients.

The present disclosure also provides methods of inhibiting FGFR4 enzyme using the solid forms (e.g., crystalline forms) as described herein.

The present disclosure also provides therapeutic methods of using the solid forms (e.g., crystalline forms) as described herein.

Provided herein are also processes for preparing N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide and its solid forms (e.g., crystalline forms) as described herein.

Provided herein are also intermediates useful for the preparation of N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide and its solid forms (e.g., crystalline forms) described herein.

DETAILED DESCRIPTION

Figure 1:
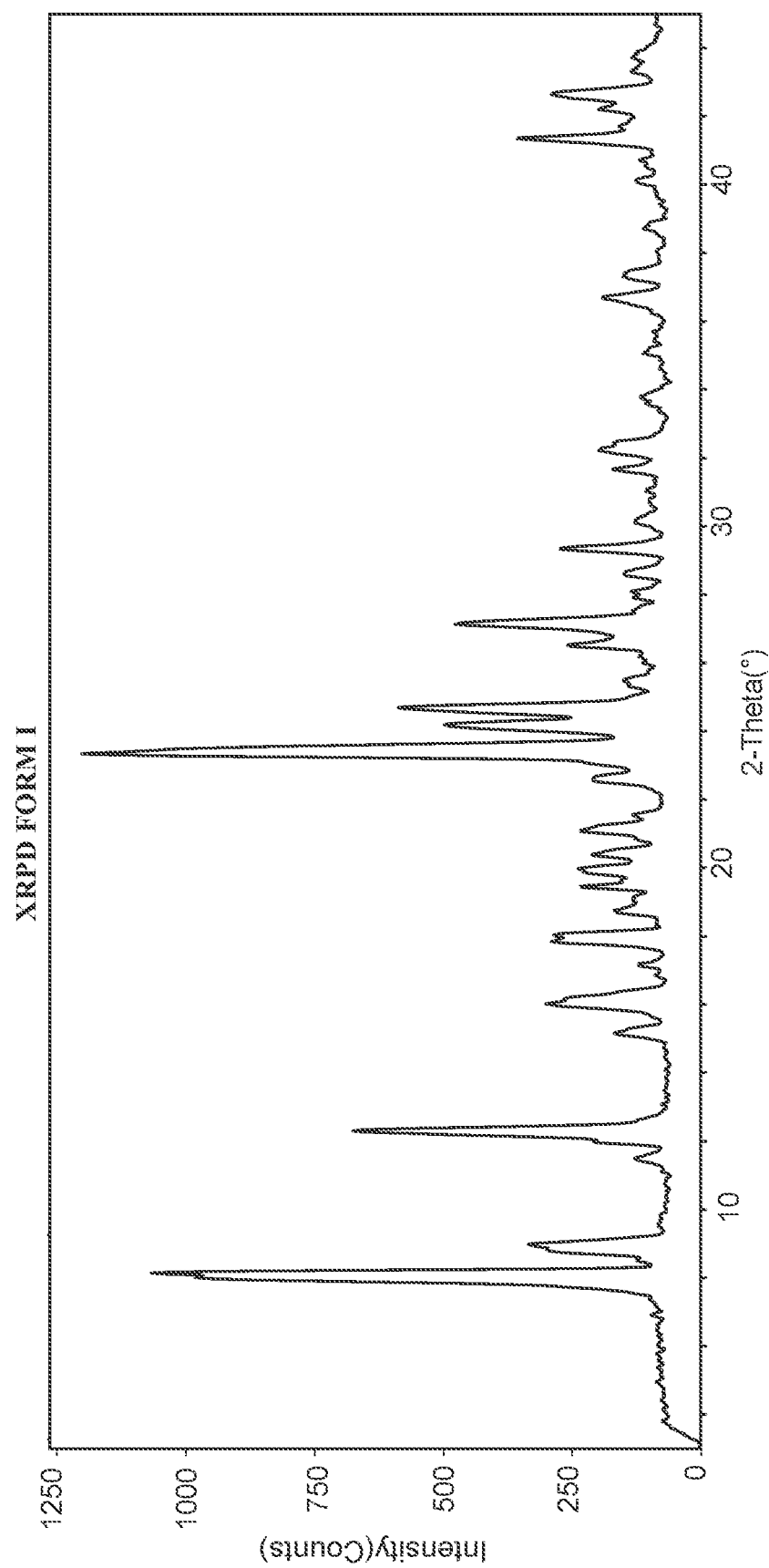
FIG. 1 shows an X-ray powder diffraction (XRPD) pattern of Compound 1, Form I.

The present disclosure is directed to, inter alia, solid forms of N-((2'-(2,6-difluoro-3,5-dimethoxyphenyl)-3'-oxo-2',3'-dihydro-1'H-spiro[cyclopropane-1,4'-[2,7]naphthyridine]-6'-yl)methyl)acrylamide (Compound 1), or a salt thereof, the structure of which is shown below.

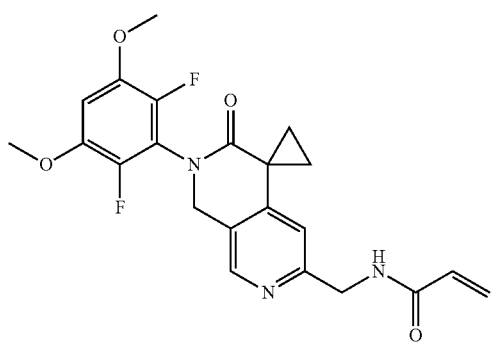

Compound 1

Compound 1 is described in US 2016/0244448, the entirety of which is incorporated herein by reference.

Compound 1 can be isolated as one or more solid forms. The solid forms (e.g., crystalline forms) described herein have many advantages, for example they have desirable properties, such as ease of handling, ease of processing, storage stability, and ease of purification. Moreover, the crystalline forms can be useful for improving the performance characteristics of a pharmaceutical product such as dissolution profile, shelf-life and bioavailability As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}C$ NMR, DSC, TGA and XRPD), indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. The term "about", when used in reference to a degree 2-theta value refers to +/−0.3 degrees 2-theta or +/−0.2 degrees 2-theta.

As used herein, the phrase "solid form" refers to a compound provided herein in either an amorphous state or a crystalline state ("crystalline form" or "crystalline solid" or "crystalline solid form"), whereby a compound provided herein in a crystalline state may optionally include solvent or water within the crystalline lattice, for example, to form a solvated or hydrated crystalline form.

As used herein, the term "peak" or "characteristic peak" refers to a reflection having a relative height/intensity of at least about 3% of the maximum peak height/intensity.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystal. For example, crystalline means having a regularly repeating and/or ordered arrangement of molecules, and possessing a distinguishable crystal lattice. The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

Different crystalline forms of a particular substance, such as Compound 1 as described herein, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 3% or at least about 4% of the maximum peak height/intensity. Moreover, instrument variation and other factors can affect the 2-theta values. Thus, peak assignments, such as those reported herein, can vary by plus or minus about 0.2° (2-theta) or about 0.3° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

As used herein, the term "amorphous" or "amorphous form" is intended to mean that the substance, component, or product in question is not crystalline as determined, for instance, by XRPD or where the substance, component, or product in question, for example is not birefringent when viewed microscopically. For example, amorphous means essentially without regularly repeating arrangement of molecules or lacks the long range order of a crystal, i.e., amorphous form is non-crystalline. An amorphous form does not display a defined x-ray diffraction pattern with sharp maxima. In certain embodiments, a sample comprising an amorphous form of a substance may be substantially free of other amorphous forms and/or crystalline forms. For example, an amorphous substance can be identified by an XRPD spectrum having an absence of reflections.

As used herein, the term "substantially amorphous" means a majority of the weight of a sample or preparation of Compound 1 is amorphous and the remainder of the sample is a crystalline form of the same compound. In some embodiments, a substantially amorphous sample has less than about 5% crystallinity (e.g., about 95% of the non-crystalline form of the same compound), less than about 4% crystallinity (e.g., about 96% of the non-crystalline form of the same compound), less than about 3% crystallinity (e.g., about 97% of the non-crystalline form of the same compound), less than about 2% crystallinity (e.g., about 98% of the non-crystalline form of the same compound), less than about 1% crystallinity (e.g., about 99% of the non-crystalline form of the same compound), or about 0% crystallinity (e.g., about 100% of the non-crystalline form of the same compound). In some embodiments, the term "fully amorphous" means less than about 99% or about 0% crystallinity.

Compound 1 can be prepared in batches referred to as batches, samples, or preparations. The batches, samples, or preparations can include Compound 1 in any of the crystalline or non-crystalline forms described herein, including hydrated and non-hydrated forms, and mixtures thereof.

Compounds provided herein (e.g., Compound 1) can also include all isotopes of atoms occurring in the intermediates or final compounds. Isotopes include those atoms having the same atomic number but different mass numbers. For example, isotopes of hydrogen include tritium and deuterium. One or more constituent atoms of the compounds provided herein can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

In some embodiments, Compound 1 is substantially isolated. The term "substantially isolated" is meant that the compound is at least partially or substantially separated from the environment in which it was formed or detected. Partial separation can include, e.g., a composition enriched in the compound, salts, hydrates, solvates, or solid forms provided herein. Substantial separation can include compositions containing at least about 50%, at least about 60%, at least about 70%, at least about 80%, at least about 90%, at least about 95%, at least about 97%, or at least about 99% by weight of the compound, salts, hydrates, solvates, or solid forms provided herein.

The term "hydrate," as used herein, is meant to refer to a solid form of Compound 1 that includes water. The water in a hydrate can be present in a stoichiometric amount with respect to the amount of salt in the solid, or can be present in varying amounts, such as can be found in connection with channel hydrates.

As used herein, the term "substantially" when referring to a characteristic figure of a crystal form, such as an XRPD pattern, a DSC thermogram, a TGA thermogram, or the like, means that a subject figure may be non-identical to the reference depicted herein, but it falls within the limits of experimental error and thus may be deemed as derived from the same crystal form as disclosed herein, as judged by a person of ordinary skill in the art.

As used herein, the term "substantially crystalline," means a majority of the weight of a sample or preparation of Compound 1 is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), at least about 96% crystallinity (e.g., about 4% of the non-crystalline form of the same compound), at least about 97% crystallinity (e.g., about 3% of the non-crystalline form of the same compound), at least about 98% crystallinity (e.g., about 2% of the non-crystalline form of the same compound), at least about 99% crystallinity (e.g., about 1% of the non-crystalline form of the same compound), or about 100% crystallinity (e.g., about 0% of the non-crystalline form of the same compound). In some embodiments, the term "fully crystalline" means at least about 99% or about 100% crystallinity.

As used herein, the term "% crystallinity" or "crystalline purity," means percentage of a crystalline form in a preparation or sample which may contain other forms such as an amorphous form of the same compound, or at least one other crystalline form of the compound, or mixtures thereof. In some embodiments, the crystalline forms can be isolated with a purity of at least about 80%, about 85%, about 90%, about 95%, about 96%, about 97%, about 98%, or about 99%. In some embodiments, the crystalline forms can be isolated with a purity greater than about 99%.

As used herein, the term "reacting" is used as known in the art and generally refers to the bringing together of chemical reagents in such a manner so as to allow their interaction at the molecular level to achieve a chemical or physical transformation. In some embodiments, the reacting involves at least two reagents, wherein one or more equivalents of second reagent are used with respect to the first reagent. In some embodiments, the reacting step of a synthetic process may involve one or more substances in addition to the reagents such as solvent and/or a catalyst. The reacting steps of the processes described herein can be conducted for a time and under conditions suitable for preparing the identified product.

As used herein, the terms "converting" with respect to changing an intermediate or starting reagent or material in a chemical reaction refers to subjecting the intermediate or starting reagent or material to the suitable reagents and conditions (e.g., temperature, time, solvent, etc.) to effect certain changes (e.g., breaking or formation of a chemical bond) to generate the desired product.

Compound 1 can be prepared in various solid forms including, e.g., Forms I, Form II, Form III, Form IV, Form V, Form VI, Form VII, Form VIII, Form IX, Form IXa, Form X, and Form XI.

Compound 1 Form I

Provided herein is a solid form of Compound 1 having Form I, which is described below in the Examples. In some embodiments, Form I has one or more characteristic XRPD peaks selected from about 8.1, about 9.0, and about 12.3 degrees 2-theta.

In some embodiments, Form I has at least one characteristic XRPD peaks selected from about 8.1, about 9.0, about 12.3, about 16.0, about 18.0, and about 23.3 degrees 2-theta.

In some embodiments, Form I has at least two characteristic XRPD peaks selected from about 8.1, about 9.0, about 11.5, about 12.3, about 15.1, about 16.0, about 18.0, about 19.6, about 20.0, about 20.4, about 21.0, about 23.3, about 24.2, about 24.7, and about 27.1 degrees 2-theta.

In some embodiments, Form I has at least three characteristic XRPD peaks selected from about 8.1, about 9.0, about 11.5, about 12.3, about 15.1, about 16.0, about 18.0, about 19.6, about 20.0, about 20.4, about 21.0, about 23.3, about 24.2, about 24.7, and about 27.1 degrees 2-theta.

In some embodiments, Form I has an XRPD pattern with characteristic peaks as substantially shown in FIG. 1.

Figure 2:
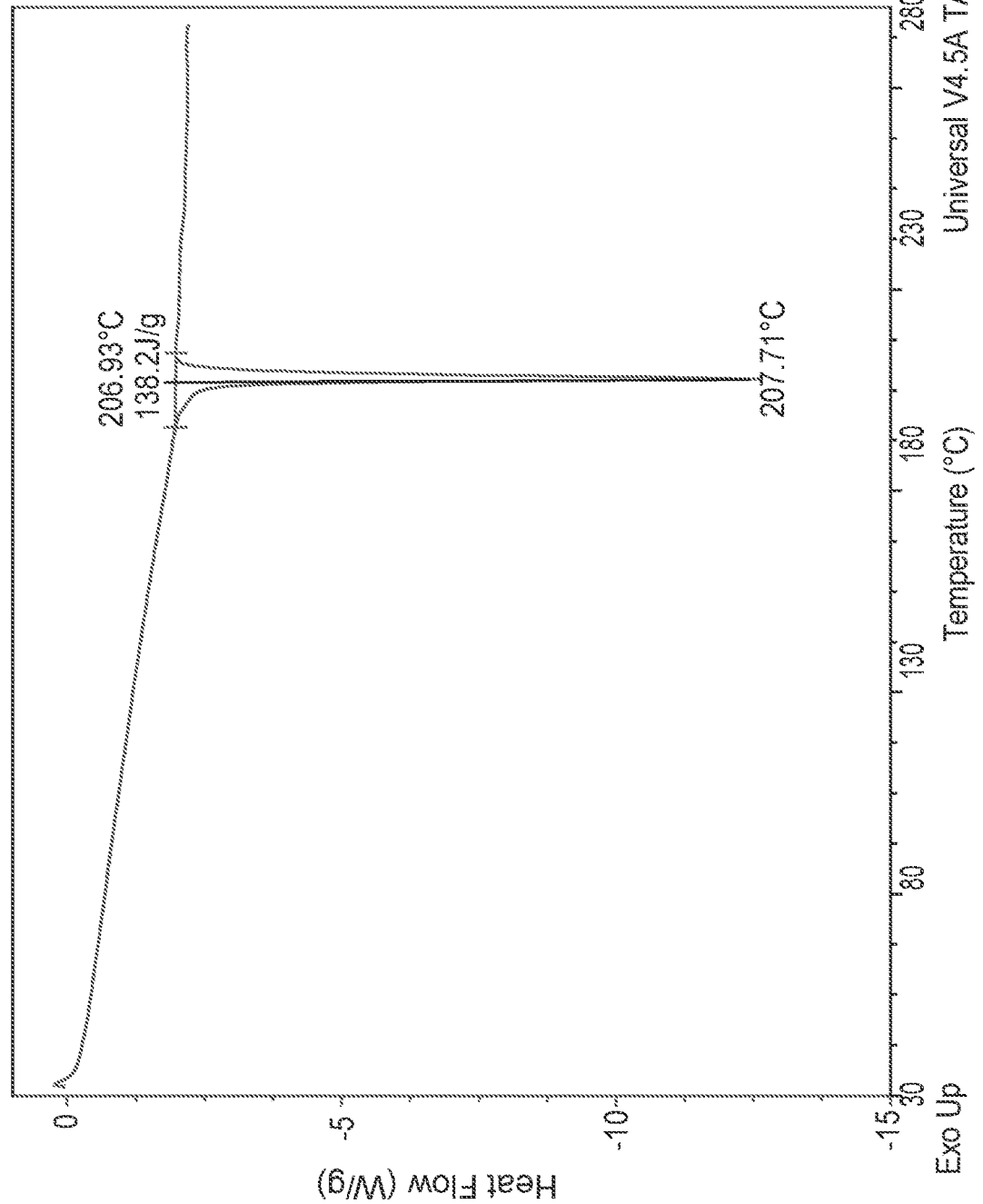
FIG. 2 shows a differential scanning calorimetry (DSC) thermogram of Compound 1, Form I.
Figure 3:
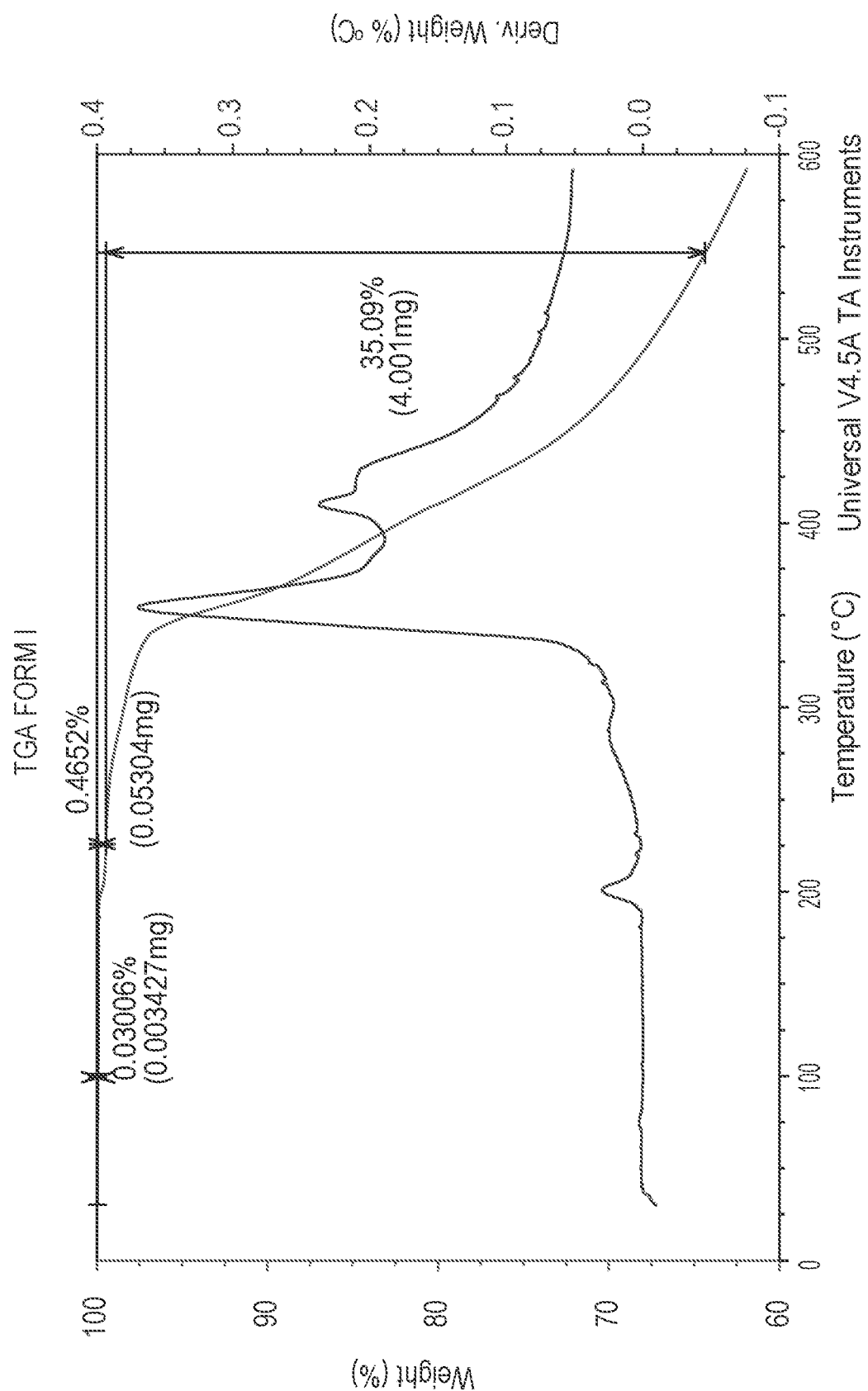
FIG. 3 shows a thermogravimetric analysis (TGA) thermogram of Compound 1, Form I.

In some embodiments, Form I exhibits a DSC thermogram having an endotherm peak at a temperature of about 208° C. In some embodiments, Form I has a DSC thermogram substantially as depicted in FIG. 2. In some embodiments, Form I has a TGA thermogram substantially as depicted in FIG. 3.

In some embodiments, Form I has one or more characteristic XRPD peaks selected from about 8.1, about 9.0, and about 12.3 degrees 2-theta; and exhibits a DSC thermogram having an endotherm peak at a temperature of about 208° C. In some embodiments, Form I has at least one characteristic XRPD peaks selected from about 8.1, about 9.0, about 12.3, about 16.0, about 18.0, and about 23.3 degrees 2-theta; and exhibits a DSC thermogram having an endotherm peak at a temperature of about 208° C.

In some embodiments, Form I has an XRPD pattern substantially as depicted in FIG. 1 and a DSC thermogram substantially as depicted in FIG. 2.

Provided herein are also processes for preparing Form I of Compound 1 comprising dissolving Compound 1 in a solvent to form a solution; and isolating Form I from the solution. The isolating can include precipitating or crystallizing Compound 1 from the solution to produce Form I.

In some embodiments, the isolating is carried out by (1) reducing the temperature of the solution of Compound 1, (2) concentrating the solution of Compound 1, or (3) a combination thereof.

Provided herein are also processes for preparing Form I of Compound 1 comprising mixing Compound 1 with a solvent to generate Form I. The process can further comprise isolating Form I. In some embodiments, the mixing includes stirring a mixture comprising compound 1 and the solvent. In some embodiments, the isolating comprises filtrating the mixture to obtain Form I.

In some embodiments, the solvent comprises acetone, water, or a mixture thereof.

In some embodiments:
the dissolving comprises heating the solution of Compound 1 to a temperature of about 40° C. to about 60° C.; and
the isolating comprises reducing the volume of the solution of Compound 1 to form a reduced-volume solution of Compound 1; and cooling the reduced-volume solution of Compound 1 to precipitate Form I. For example, the solution can be cooled to 22° C.

In some embodiments:
the dissolving comprises heating the solution of Compound 1 to a temperature of about 40° C. to about 60° C., wherein the solution comprises acetone and water as solvent; and
the isolating comprises reducing the volume of the solution of Compound 1 to form a reduced-volume solution of Compound 1; and cooling the reduced-volume solution of Compound 1 to precipitate Form I.

In some embodiments, Form I can be isolated with a purity of at least about 80%, about 85%, about 90%, about 95%, about 96%, about 97%, about 98%, or about 99%. In some embodiments, Form I can be isolated with a purity greater than about 99%.

Compound 1 Form II

Provided herein is a solid form of Compound 1 having Form II, which is described below in the Examples. In some embodiments, Form II has one or more characteristic XRPD peaks selected from about 11.4, about 12.6, about 14.7, and about 16.1 degrees 2-theta.

In some embodiments, Form II has at least one characteristic XRPD peaks selected from about 11.4, about 12.6, about 14.7, about 16.1, about 18.3, about 21.2, and about 24.8 degrees 2-theta.

In some embodiments, Form II has at least two characteristic XRPD peaks selected from about 11.4, about 12.6, about 14.5, about 14.7, about 16.1, about 18.3, about 21.2, about 24.8, about 27.9, and about 28.3 degrees 2-theta.

In some embodiments, Form II has at least three characteristic XRPD peaks selected from about 11.4, about 12.6, about 14.5, about 14.7, about 16.1, about 18.3, about 21.2, about 24.8, about 27.9, and about 28.3 degrees 2-theta.

Figure 4:
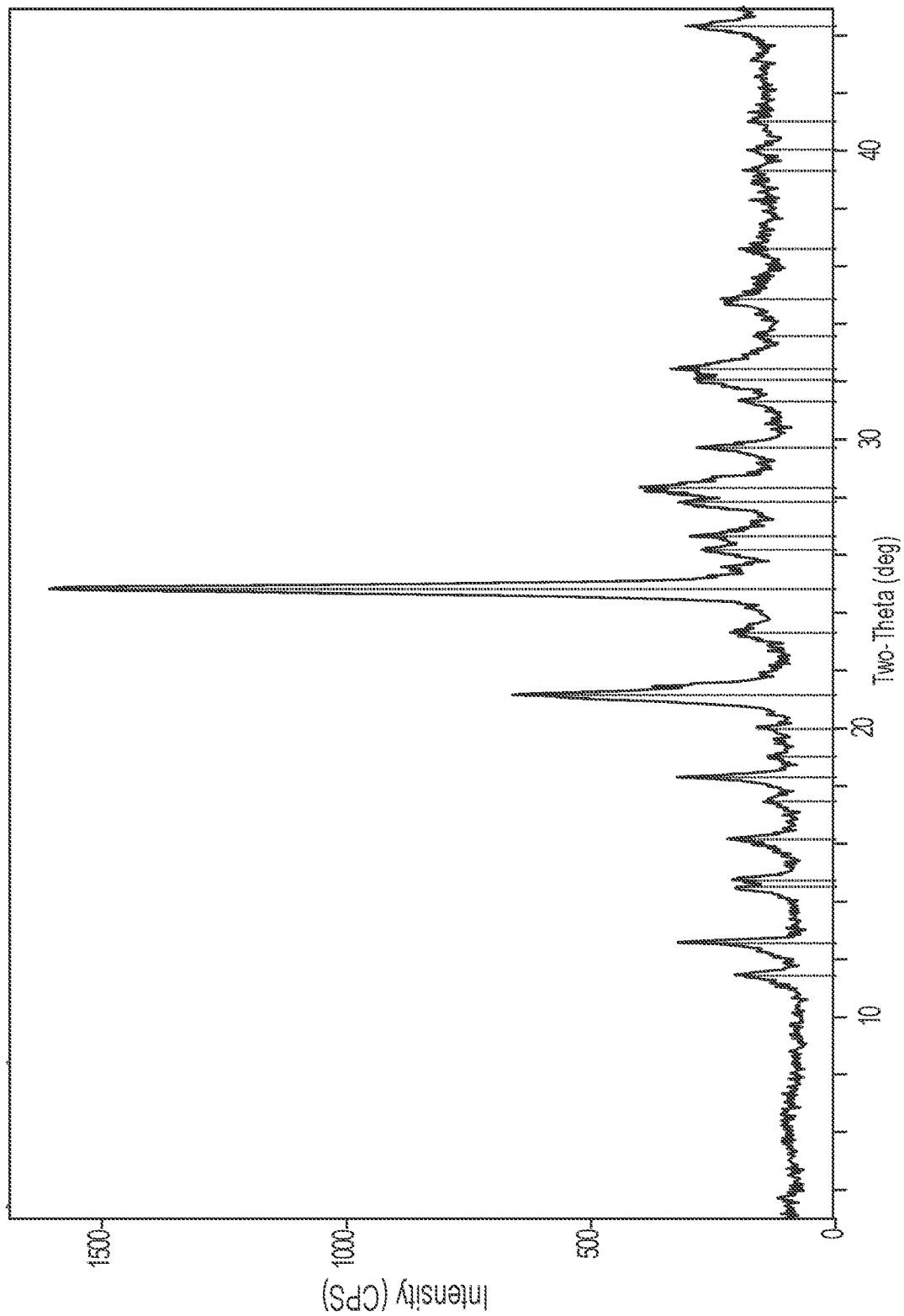
FIG. 4 shows an XRPD pattern of Compound 1, Form II.

In some embodiments, Form II has an XRPD pattern with characteristic peaks as substantially shown in FIG. 4.

Figure 5:
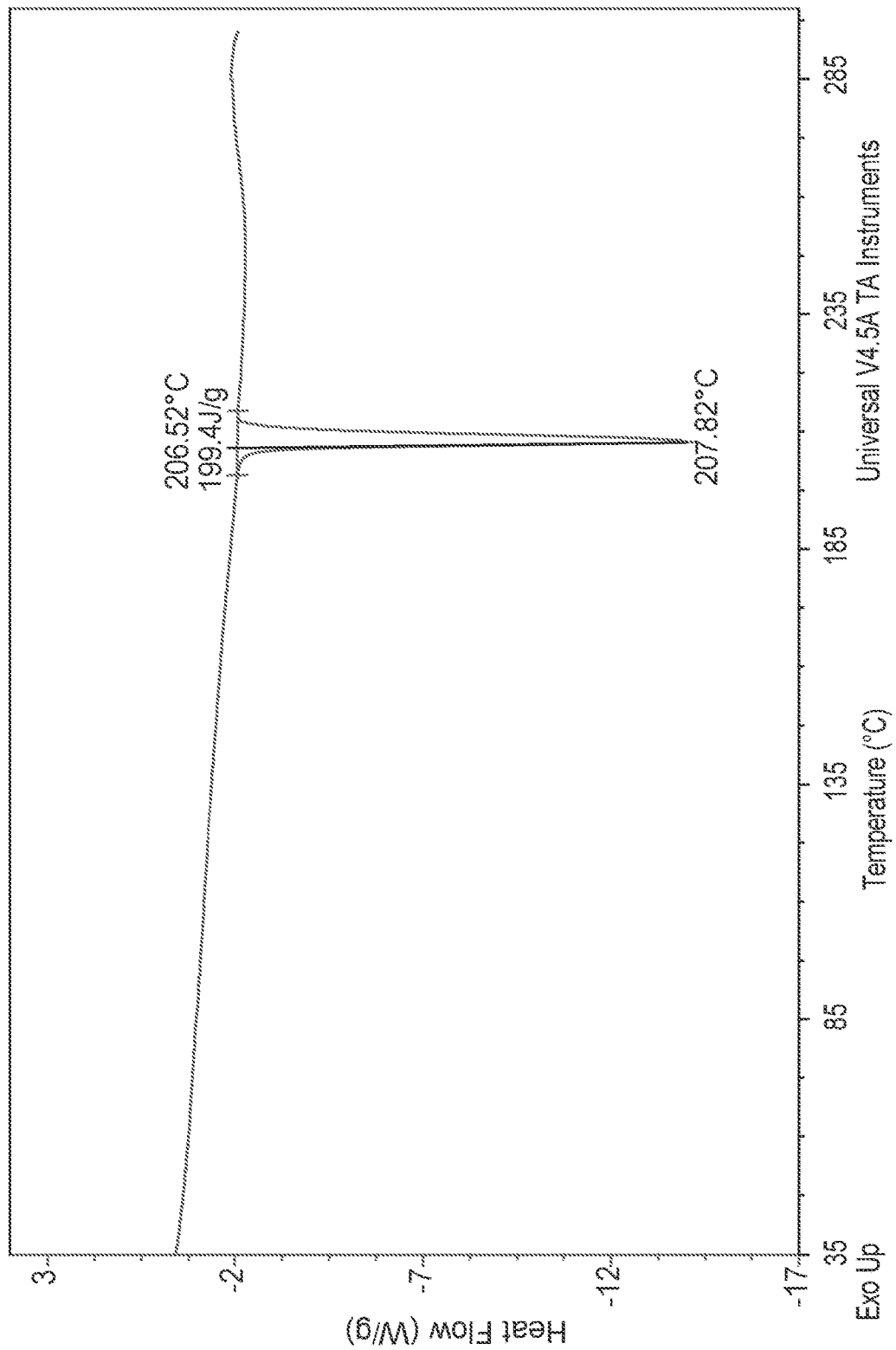
FIG. 5 shows a DSC thermogram of Compound 1, Form II.
Figure 6:
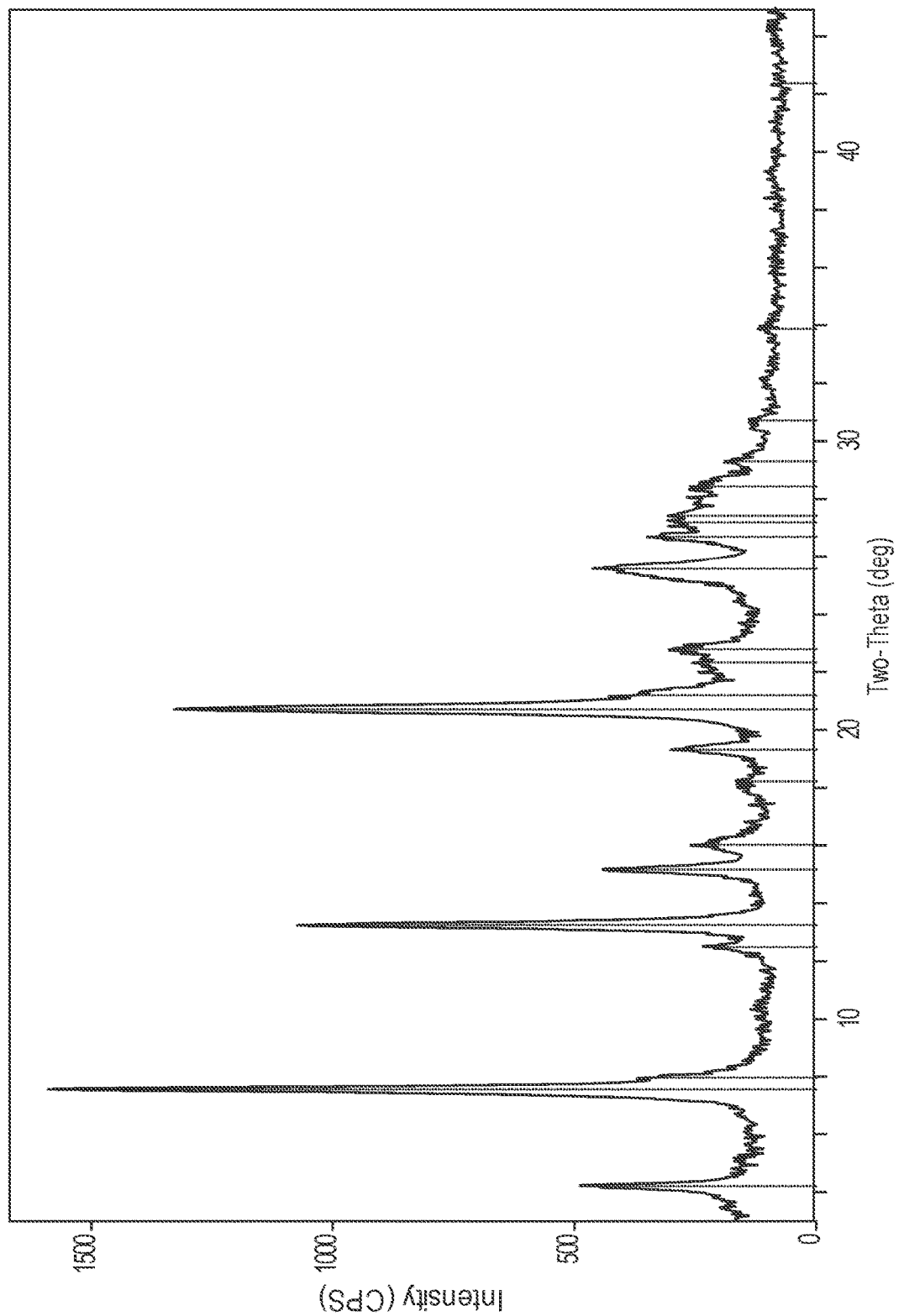
FIG. 6 shows an XRPD pattern of Compound 1, Form III.

In some embodiments, Form II exhibits a DSC thermogram having an endotherm peak at a temperature of about 208° C. In some embodiments, Form II has a DSC thermogram substantially as depicted in FIG. 5. In some embodiments, Form II has a TGA thermogram substantially as depicted in FIG. 6.

In some embodiments, Form II has one or move characteristic XRPD peaks selected from about 11.4, about 12.6, about 14.7, and about 16.1 degrees 2-theta; and exhibits a DSC thermogram having an endotherm peak at a temperature of about 208° C.

In some embodiments, Form II has at least one characteristic XRPD peaks selected from about 11.4, about 12.6, about 14.7, about 16.1, about 18.3, about 21.2, and about 24.8 degrees 2-theta; and exhibits a DSC thermogram having an endotherm peak at a temperature of about 208° C.

In some embodiments, Form II has an XRPD pattern substantially as depicted in FIG. 4 and a DSC thermogram substantially as depicted in FIG. 5.

In some embodiments, Form II can be isolated with a purity of at least about 80%, about 85%, about 90%, about 95%, about 96%, about 97%, about 98%, or about 99%. In some embodiments, Form II can be isolated with a purity greater than about 99%.

Compound 1 Form III

Provided herein is a solid form of Compound 1 having Form III, which is described below in the Examples. In some embodiments, Form III has one or more characteristic XRPD peaks selected from about 4.2, about 7.6, and about 15.2 degrees 2-theta.

In some embodiments, Form III has at least one characteristic XRPD peak selected from about 4.2, about 7.6, about 13.2, about 15.2, about 19.3, and about 20.7 degrees 2-theta.

In some embodiments, Form III has at least two characteristic XRPD peaks selected from about 4.2, about 7.6, about 8.0, about 12.5, about 13.2, about 15.2, about 16.0, about 19.3, about 20.7, and about 25.6 degrees 2-theta.

In some embodiments, Form III has at least three characteristic XRPD peaks selected from about 4.2, about 7.6, about 8.0, about 12.5, about 13.2, about 15.2, about 16.0, about 19.3, about 20.7, and about 25.6 degrees 2-theta.

In some embodiments, Form III has an XRPD pattern with characteristic peaks as substantially shown in FIG. 6.

In some embodiments, Form III exhibits a DSC thermogram having an endotherm peak at a temperature of about 207° C. In some embodiments, Form III has a DSC thermogram substantially as depicted in FIG. 7.

In some embodiments, Form III has one or more characteristic XRPD peak selected from about 4.2, about 7.6, and about 15.2 degrees 2-theta; and exhibits a DSC thermogram having an endotherm peak at a temperature of about 207° C.

In some embodiments, Form III has at least one characteristic XRPD peaks selected from about 4.2, about 7.6, about 13.2, about 15.2, about 19.3, and about 20.7 degrees 2-theta; and exhibits a DSC thermogram having an endotherm peak at a temperature of about 207° C.

Figure 7:
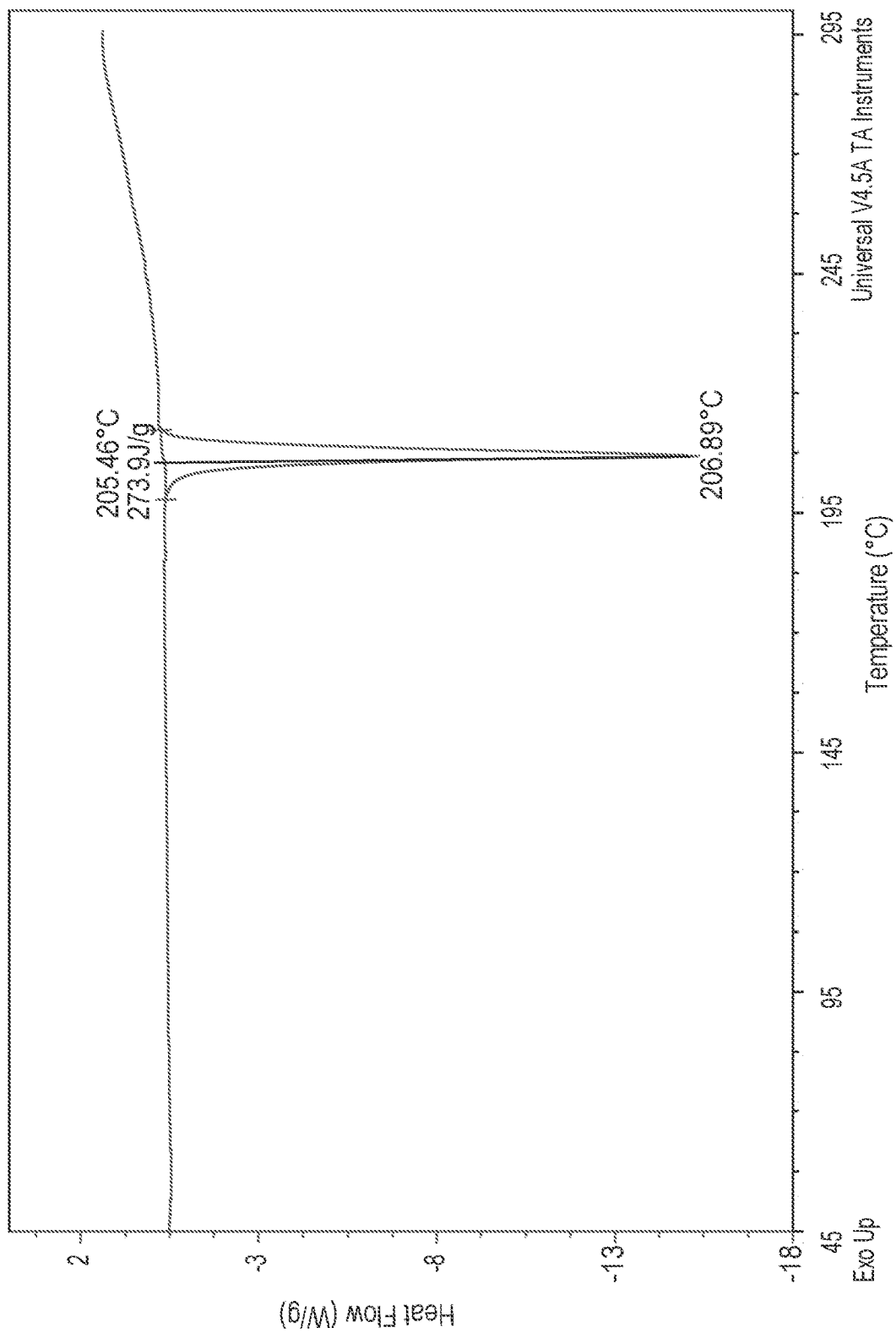
FIG. 7 shows a DSC thermogram of Compound 1, Form III.

In some embodiments, Form III has an XRPD pattern substantially as depicted in FIG. 6 and a DSC thermogram substantially as depicted in FIG. 7.

In some embodiments, Form III can be isolated with a purity of at least about 80%, about 85%, about 90%, about 95%, about 96%, about 97%, about 98%, or about 99%. In some embodiments, Form III can be isolated with a purity greater than about 99%.

Compound 1 Form IV

Provided herein is a solid form of Compound 1 having Form IV, which is described below in the Examples. In some embodiments, Form IV has one or more characteristic XRPD peaks selected from about 4.3, about 11.9, and about 12.9 degrees 2-theta.

In some embodiments, Form IV has at least one characteristic XRPD peak selected from about 4.3, about 11.9, about 12.9, about 14.3, about 15.1, and about 18.0 degrees 2-theta.

In some embodiments, Form IV has at least two characteristic XRPD peaks selected from about 4.3, about 11.9, about 12.9, about 14.3, about 15.1, about 15.5, about 18.0, about 23.3, about 24.5, about 25.1, and about 26.8 degrees 2-theta.

In some embodiments, Form IV has at least three characteristic XRPD peaks selected from about 4.3, about 11.9, about 12.9, about 14.3, about 15.1, about 15.5, about 18.0, about 23.3, about 24.5, about 25.1, and about 26.8 degrees 2-theta.

Figure 8:
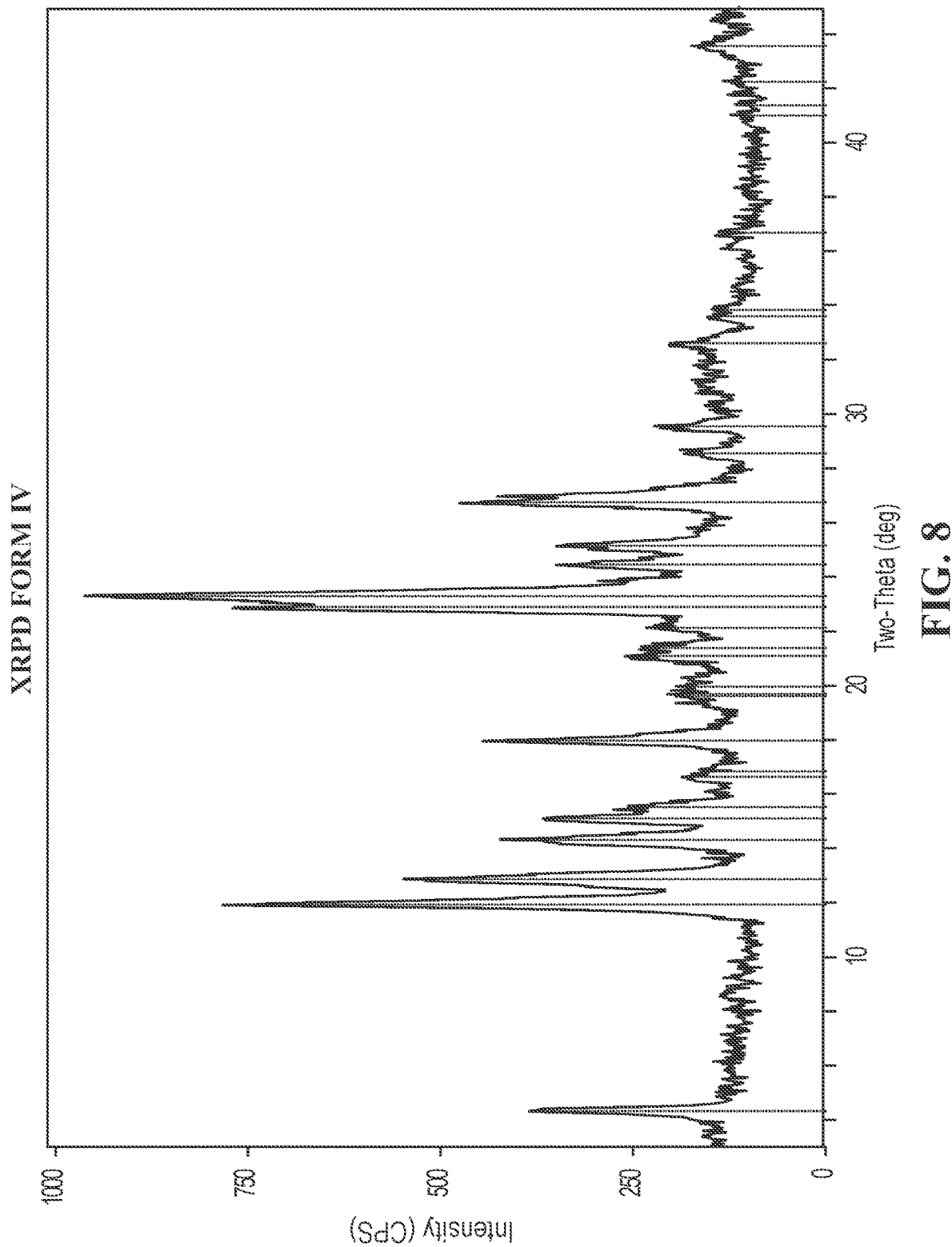
FIG. 8 shows an XRPD pattern of Compound 1, Form IV.

In some embodiments, Form IV has an XRPD pattern with characteristic peaks as substantially shown in FIG. 8.

In some embodiments, Form IV exhibits a DSC thermogram having an endotherm peak at a temperature of about 208° C. In some embodiments, Form IV has a DSC thermogram substantially as depicted in FIG. 9.

In some embodiments, Form IV has one or more characteristic XRPD peaks selected from about 4.3, about 11.9, and about 12.9 degrees 2-theta; and exhibits a DSC thermogram having endotherm peak at a temperature of about 208° C.

In some embodiments, Form IV has at least one characteristic XRPD peaks selected from about 4.3, about 11.9, about 12.9, about 14.3, about 15.1, and about 18.0 degrees 2-theta; and exhibits a DSC thermogram having an endotherm peak at a temperature of about 208° C.

Figure 9:
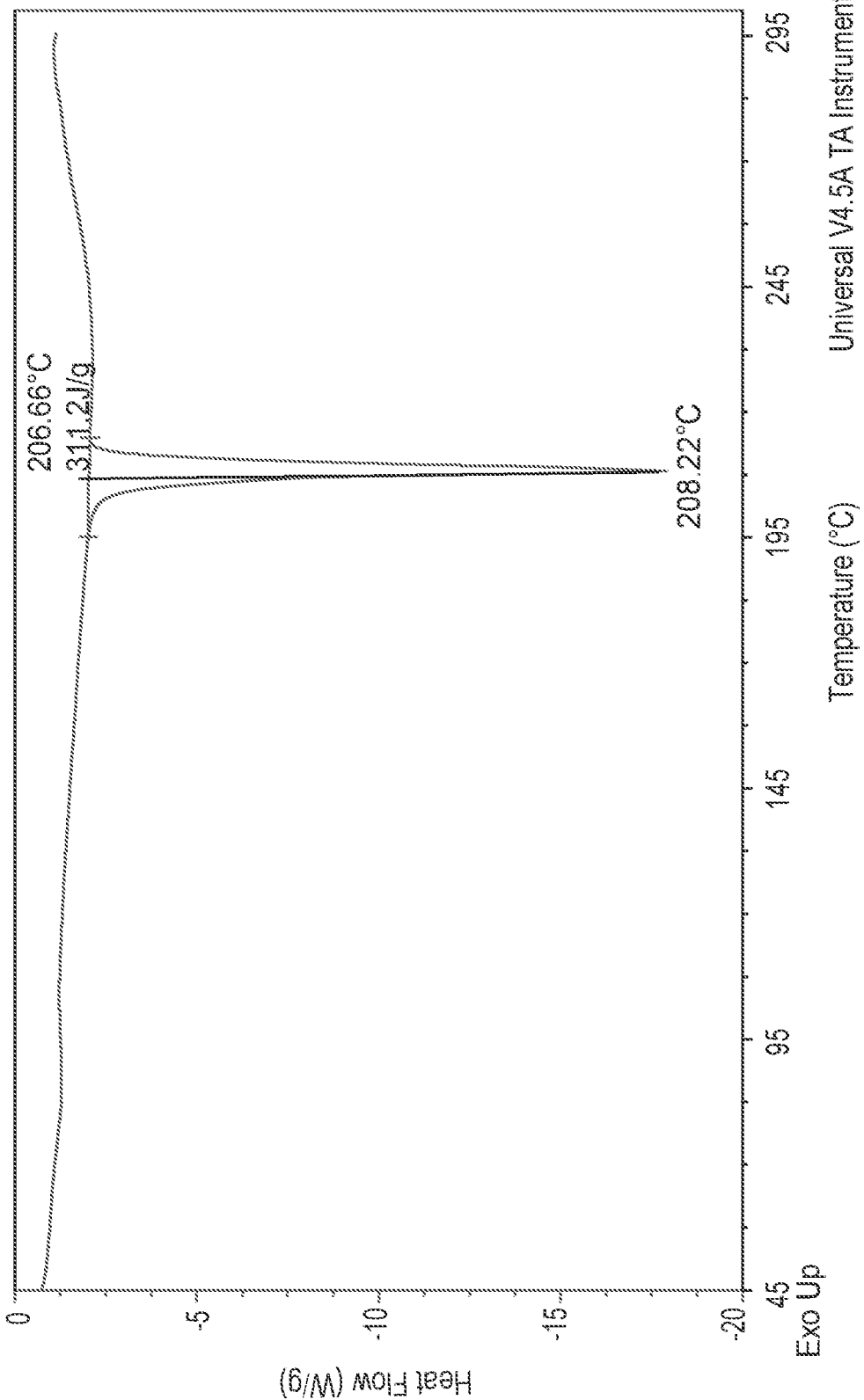
FIG. 9 shows a DSC thermogram of Compound 1, Form IV.

In some embodiments, Form IV has an XRPD pattern substantially as depicted in FIG. 8 and a DSC thermogram substantially as depicted in FIG. 9.

In some embodiments, Form IV can be isolated with a purity of at least about 80%, about 85%, about 90%, about 95%, about 96%, about 97%, about 98%, or about 99%. In some embodiments, Form IV can be isolated with a purity greater than about 99%.

Compound 1 Form V

Provided herein is a solid form of Compound 1 having Form V, which is described below in the Examples. In some embodiments, Form V has one or more characteristic XRPD peaks selected from about 6.6, about 8.2, about 9.2, and about 17.9 degrees 2-theta.

In some embodiments, Form V has at least one characteristic XRPD peak selected from about 6.6, about 8.2, about 9.2, about 11.5, about 13.5, about 15.6, about 17.9, about 19.4, and about 20.7 degrees 2-theta.

In some embodiments, Form V has at least two characteristic XRPD peaks selected from about 6.6, about 8.2, about 9.2, about 11.5, about 13.5, about 15.6, about 17.9, about 19.4, about 20.7, about 23.5, and about 26.8 degrees 2-theta.

In some embodiments, Form V has at least three characteristic XRPD peaks selected from about 6.6, about 8.2, about 9.2, about 11.5, about 13.5, about 15.6, about 17.9, about 19.4, about 20.7, about 23.5, and about 26.8 degrees 2-theta.

Figure 10:
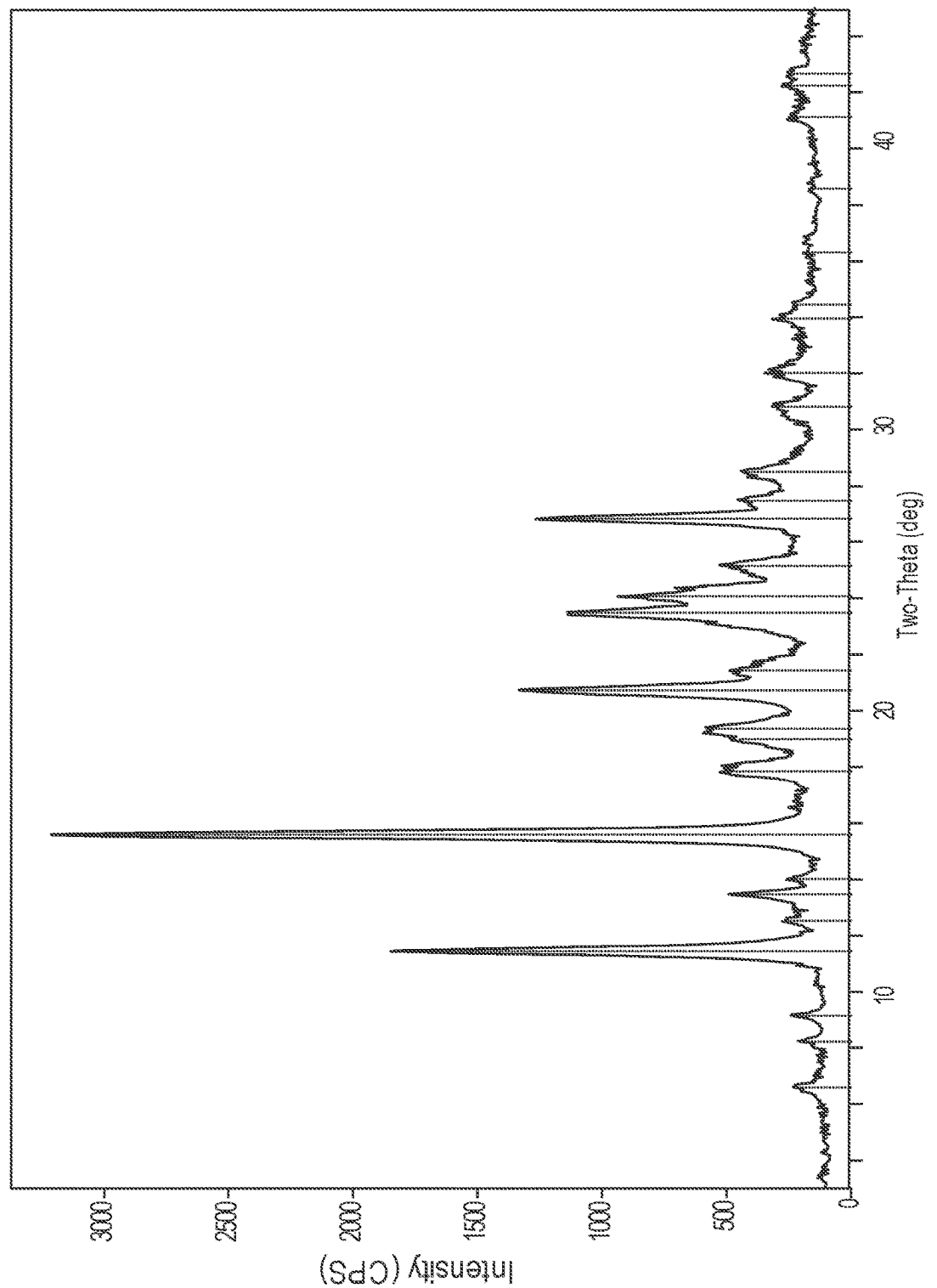
FIG. 10 shows an XRPD pattern of Compound 1, Form V.

In some embodiments, Form V has an XRPD pattern with characteristic peaks as substantially shown in FIG. 10.

Figure 11:
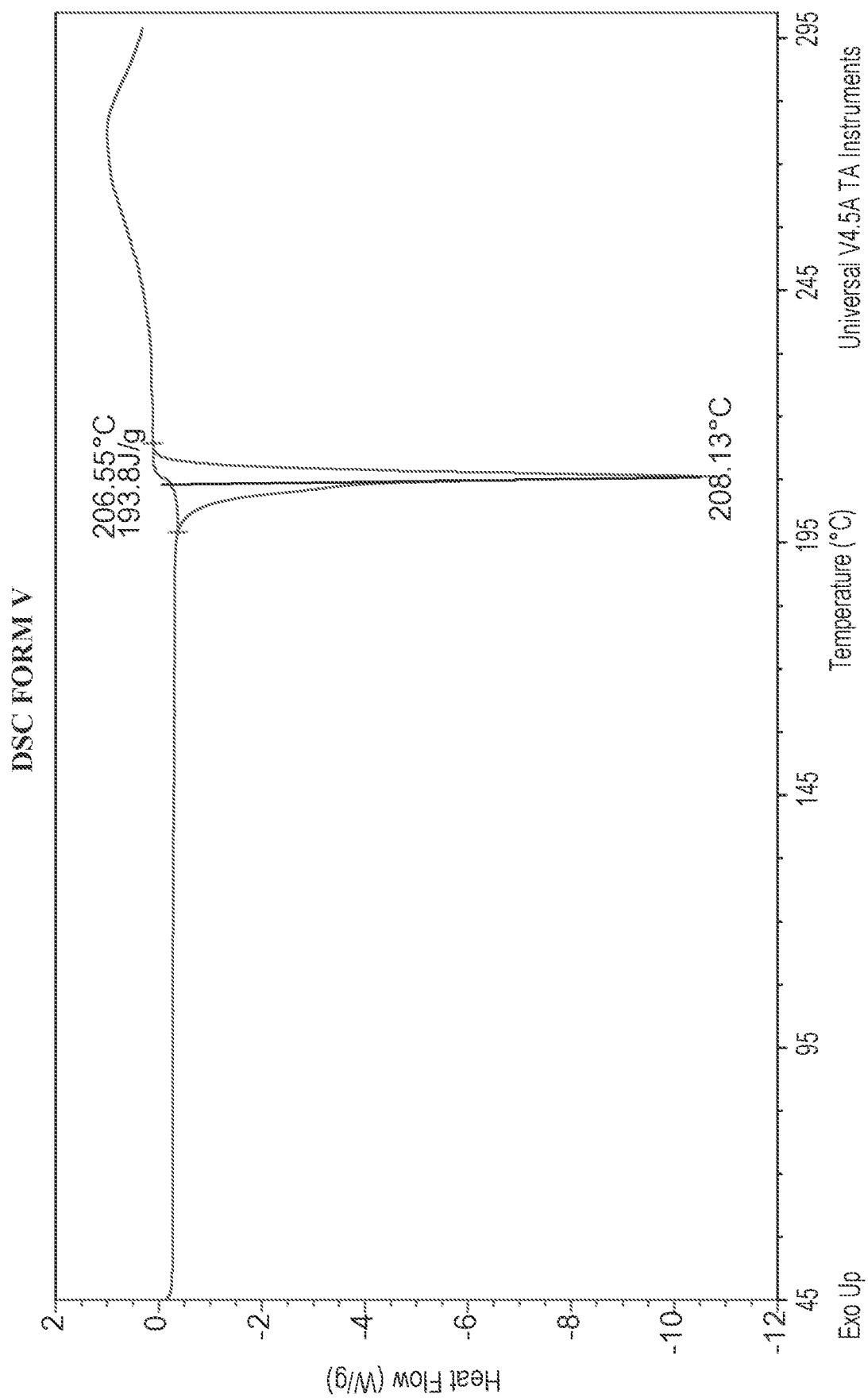
FIG. 11 shows a DSC thermogram of Compound 1, Form V.
Figure 12:
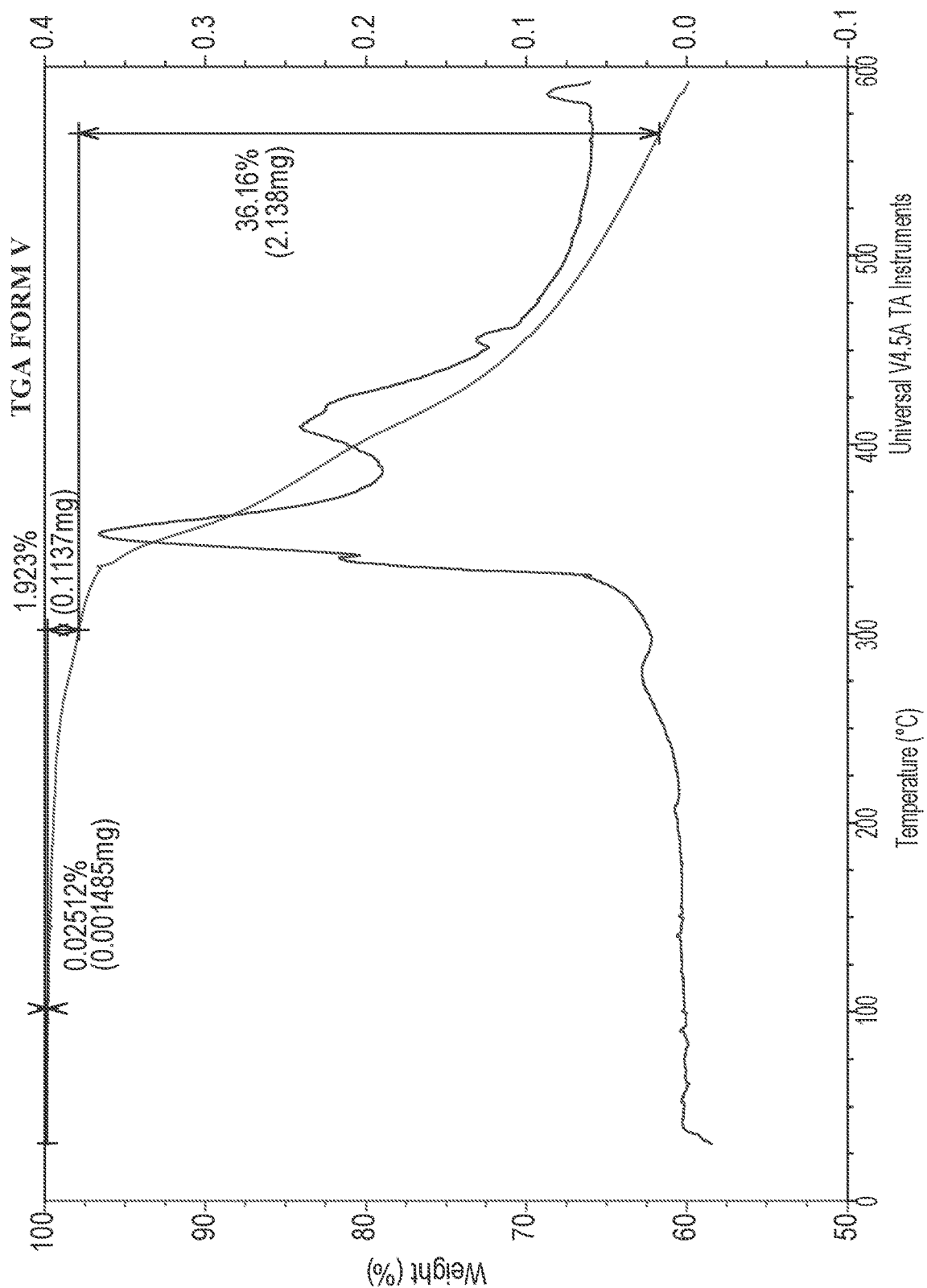
FIG. 12 shows a TGA thermogram of Compound 1, Form V.

In some embodiments, Form V exhibits a DSC thermogram having an endotherm peak at a temperature of about 208° C. In some embodiments, Form V has a DSC thermogram substantially as depicted in FIG. 11. In some embodiments, Form V has a TGA thermogram substantially as depicted in FIG. 12.

In some embodiments, Form V has one or more characteristic XRPD peaks selected from about 6.6, about 8.2, about 9.2, and about 17.9 degrees 2-theta; and exhibits a DSC thermogram having an endotherm peak at a temperature of about 208° C.

In some embodiments, Form V has at least one characteristic XRPD peaks selected from about 6.6, about 8.2, about 9.2, about 11.5, about 13.5, about 15.6, about 17.9, about 19.4, and about 20.7 degrees 2-theta; and exhibits a DSC thermogram having an endotherm peak at a temperature of about 208° C.

In some embodiments, Form V has an XRPD pattern substantially as depicted in FIG. 10 and a DSC thermogram substantially as depicted in FIG. 11.

In some embodiments, Form V can be isolated with a purity of at least about 80%, about 85%, about 90%, about 95%, about 96%, about 97%, about 98%, or about 99%. In some embodiments, Form V can be isolated with a purity greater than about 99%.

Compound 1 Form VI

Provided herein is a solid form of Compound 1 having Form VI, which is described below in the Examples. In some embodiments, Form VI has one or more characteristic XRPD peaks selected from about 4.4, about 5.2, and about 6.8 degrees 2-theta.

In some embodiments, Form VI has at least one characteristic XRPD peaks selected from about 4.4, about 5.2, about 6.8, about 10.1, about 10.5, about 13.2, and about 15.8 degrees 2-theta.

In some embodiments, Form VI has at least two characteristic XRPD peaks selected from about 4.4, about 5.2, about 6.8, about 10.1, about 10.5, about 12.7, about 13.2, about 15.8, about 18.4, about 19.2, about 19.6, and about 20.4 degrees 2-theta.

In some embodiments, Form VI has at least three characteristic XRPD peaks selected from about 4.4, about 5.2, about 6.8, about 10.1, about 10.5, about 12.7, about 13.2, about 15.8, about 18.4, about 19.2, about 19.6, and about 20.4 degrees 2-theta.

Figure 13:
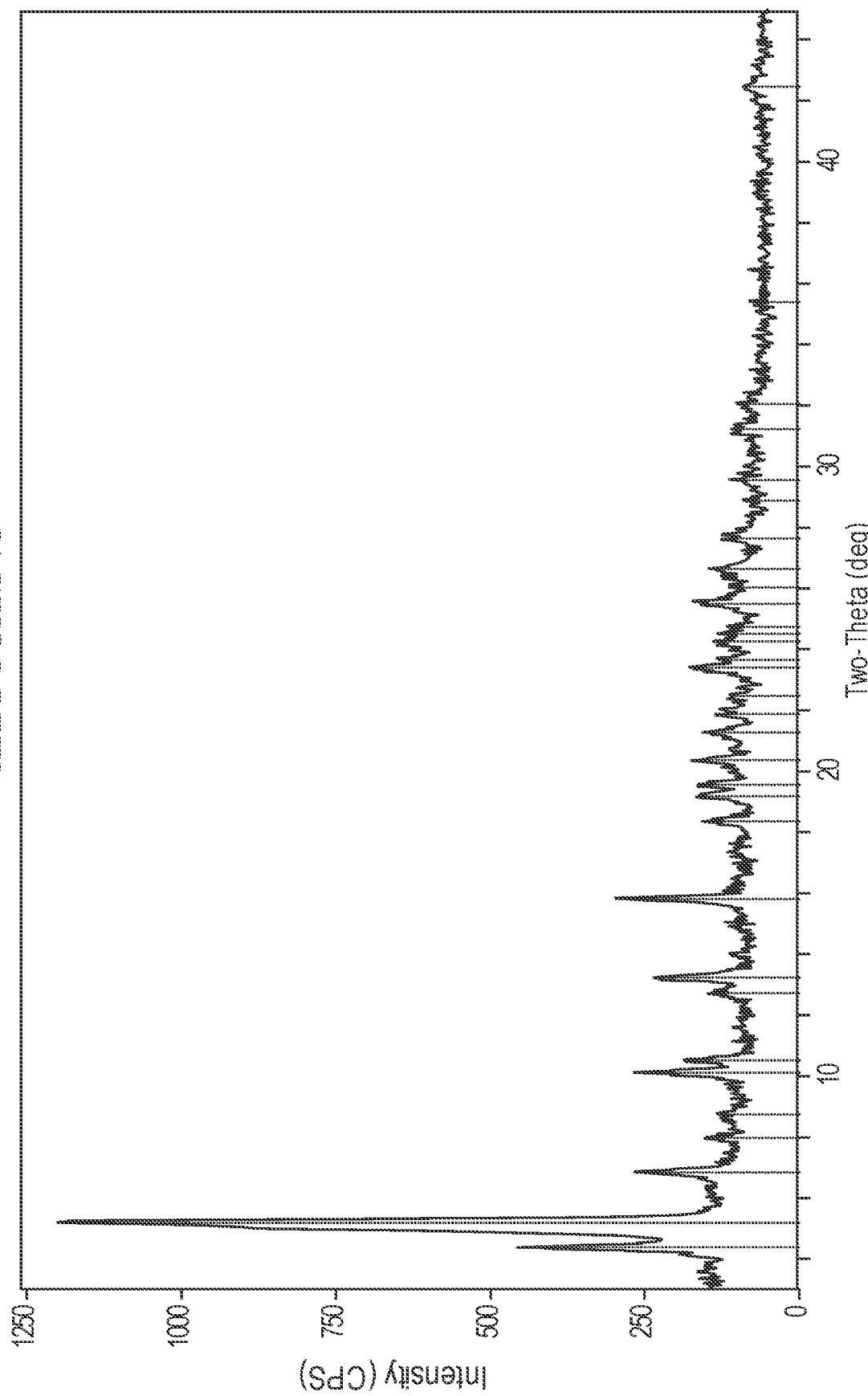
FIG. 13 shows an XRPD pattern of Compound 1, Form VI.

In some embodiments, Form VI has an XRPD pattern with characteristic peaks as substantially shown in FIG. 13.

In some embodiments, Form VI can be isolated with a purity of at least about 80%, about 85%, about 90%, about 95%, about 96%, about 97%, about 98%, or about 99%. In some embodiments, Form VI can be isolated with a purity greater than about 99%.

Compound 1 Form VII

Provided herein is a solid form of Compound 1 having Form VII, which is described below in the Examples. In some embodiments, Form VII has one or more characteristic XRPD peaks selected from about 5.1, about 8.0, and about 10.2 degrees 2-theta.

In some embodiments, Form VII has at least one characteristic XRPD peaks selected from about 5.1, about 8.0, about 10.2, about 12.3, about 13.0, about 13.5, and about 16.3 degrees 2-theta.

In some embodiments, Form VII has at least two characteristic XRPD peaks selected from about 5.1, about 8.0, about 10.2, about 12.3, about 13.0, about 13.5, about 15.6, about 16.3, about 18.2, about 21.3, about 24.7, and about 37.4 degrees 2-theta.

In some embodiments, Form VII has at least three characteristic XRPD peaks selected from about 5.1, about 8.0, about 10.2, about 12.3, about 13.0, about 13.5, about 15.6, about 16.3, about 18.2, about 21.3, about 24.7, and about 37.4 degrees 2-theta.

Figure 14:
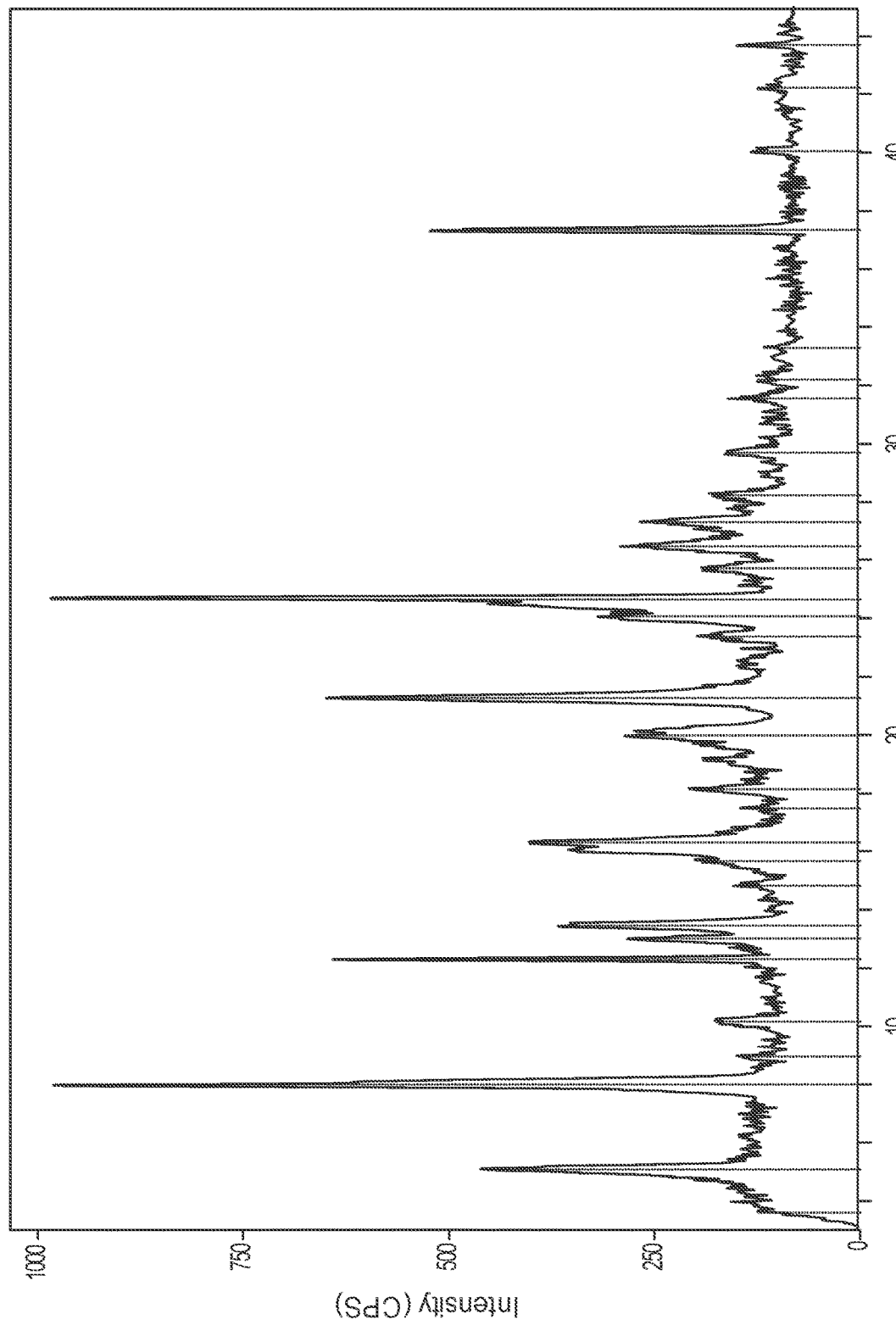
FIG. 14 shows an XRPD pattern of Compound 1, Form VII.

In some embodiments, Form VII has an XRPD pattern with characteristic peaks as substantially shown in FIG. 14.

Figure 15:
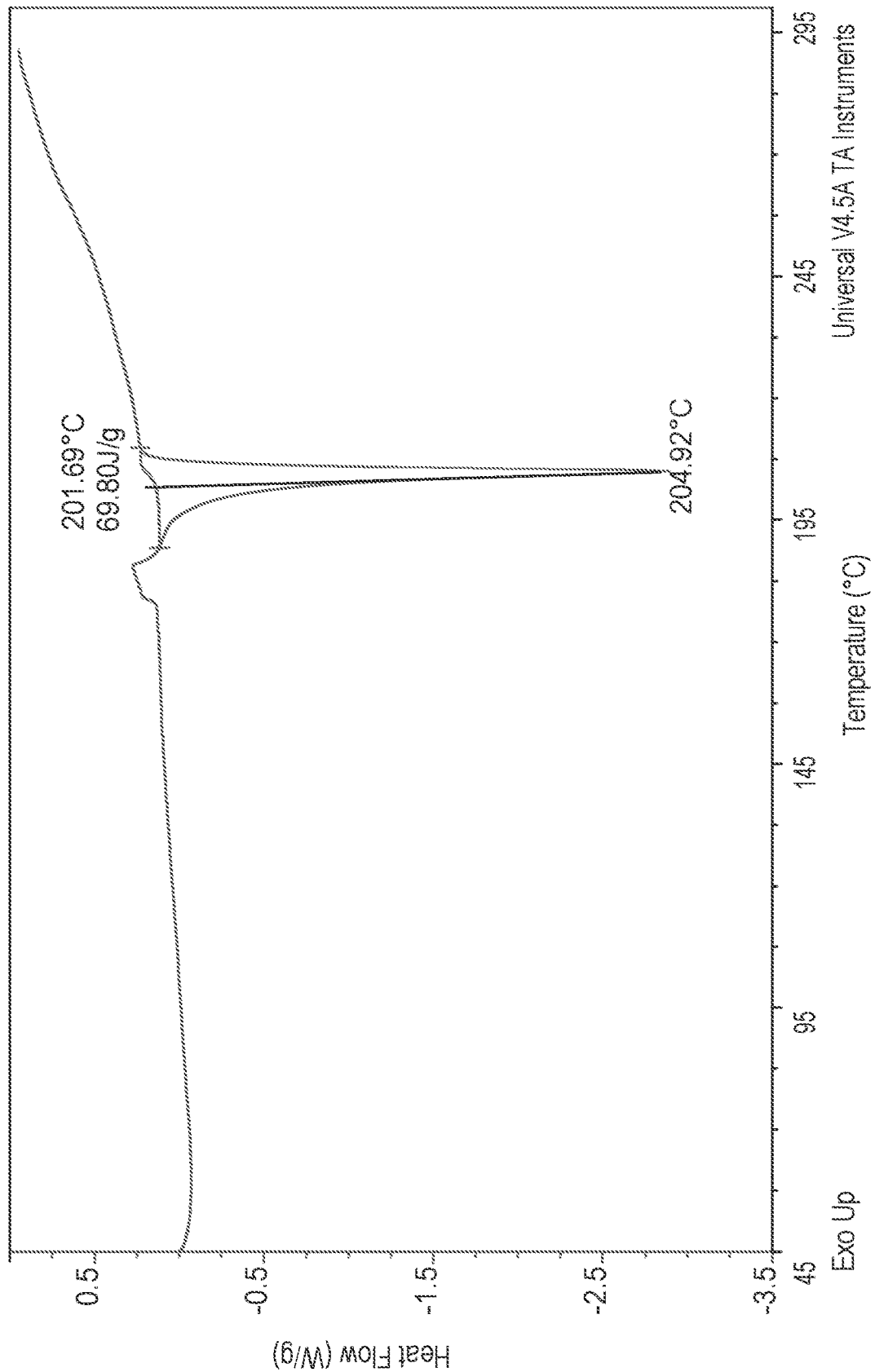
FIG. 15 shows a DSC thermogram of Compound 1, Form VII.
Figure 16:
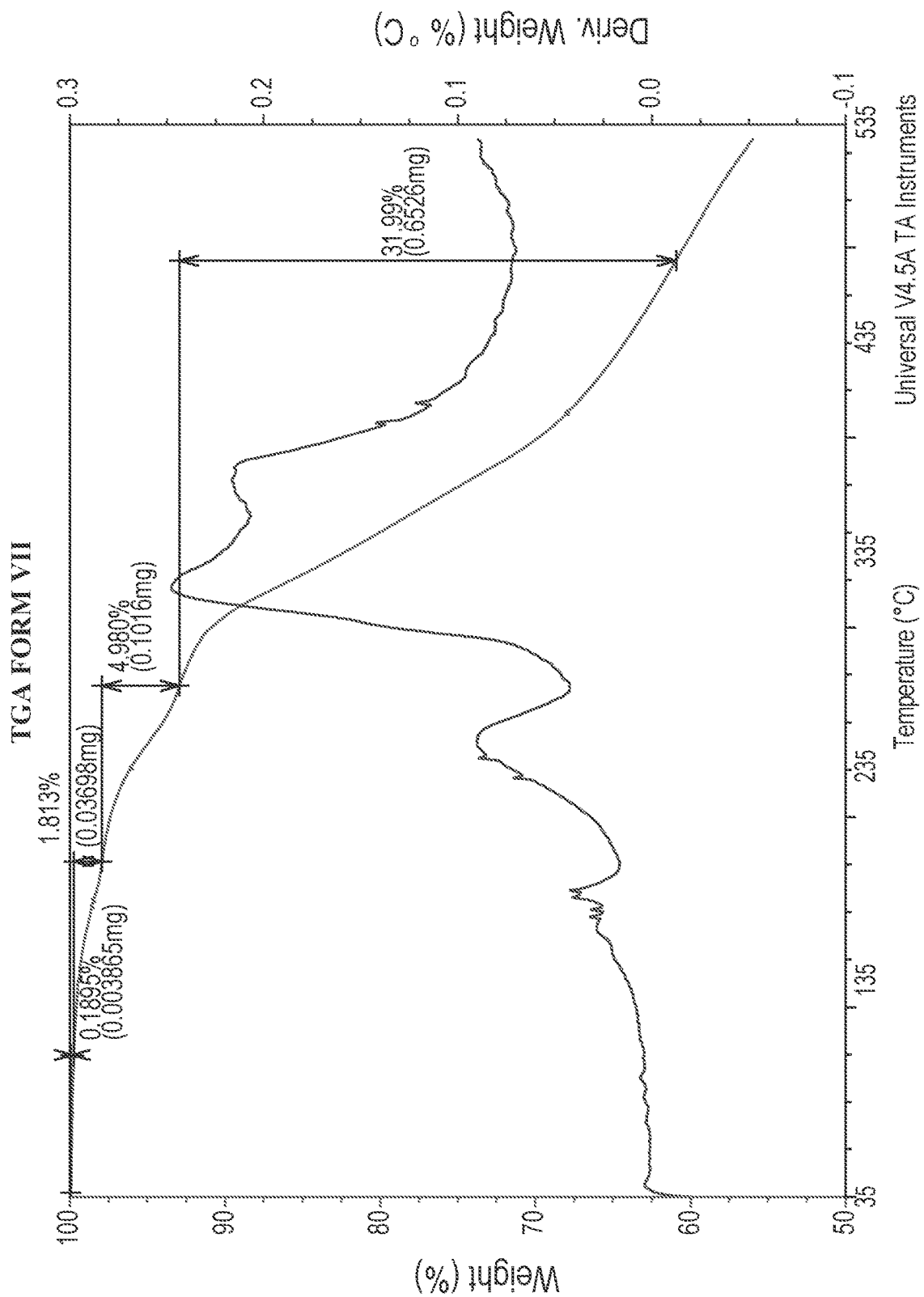
FIG. 16 shows a TGA thermogram of Compound 1, Form VII.

In some embodiments, Form VII exhibits a DSC thermogram having an endotherm peak at a temperature of about 205° C. In some embodiments, Form VII has a DSC thermogram substantially as depicted in FIG. 15. In some embodiments, Form VII has a TGA thermogram substantially as depicted in FIG. 16.

In some embodiments, Form VII has one or more characteristic XRPD peaks selected from about 5.1, about 8.0, and about 10.2 degrees 2-theta; and exhibits a DSC thermogram having an endotherm peak at a temperature of about 205° C.

In some embodiments, Form VII has at least one characteristic XRPD peaks selected from about 5.1, about 8.0, about 10.2, about 12.3, about 13.0, about 13.5, and about 16.3 degrees 2-theta; exhibits a DSC thermogram having an endotherm peak at a temperature of about 205° C.

In some embodiments, Form VII has an XRPD pattern substantially as depicted in FIG. 14 and a DSC thermogram substantially as depicted in FIG. 15.

In some embodiments, Form VII can be isolated with a purity of at least about 80%, about 85%, about 90%, about 95%, about 96%, about 97%, about 98%, or about 99%. In some embodiments, Form VII can be isolated with a purity greater than about 99%.

Compound 1 Form VIII

Provided herein is a solid form of Compound 1 having Form VIII, which is described below in the Examples. In some embodiments, Form VIII has one or more characteristic XRPD peaks selected from about 4.5, about 8.0, and about 9.0 degrees 2-theta.

In some embodiments, Form VIII has at least one characteristic XRPD peaks selected from about 4.5, about 8.0, about 9.0, about 12.7, about 13.3, about 14.3, about 15.5, about 16.4, and about 18.1 degrees 2-theta.

In some embodiments, Form VIII has at least two characteristic XRPD peaks selected from about 4.5, about 8.0, about 9.0, about 12.7, about 13.3, about 14.3, about 15.5, about 16.4, about 18.1, about 19.6, about 20.2, about 20.7, about 24.0, about 25.4, and about 26.6 degrees 2-theta.

In some embodiments, Form VIII has at least three characteristic XRPD peaks selected from about 4.5, about 8.0, about 9.0, about 12.7, about 13.3, about 14.3, about 15.5, about 16.4, about 18.1, about 19.6, about 20.2, about 20.7, about 24.0, about 25.4, and about 26.6 degrees 2-theta.

Figure 17:
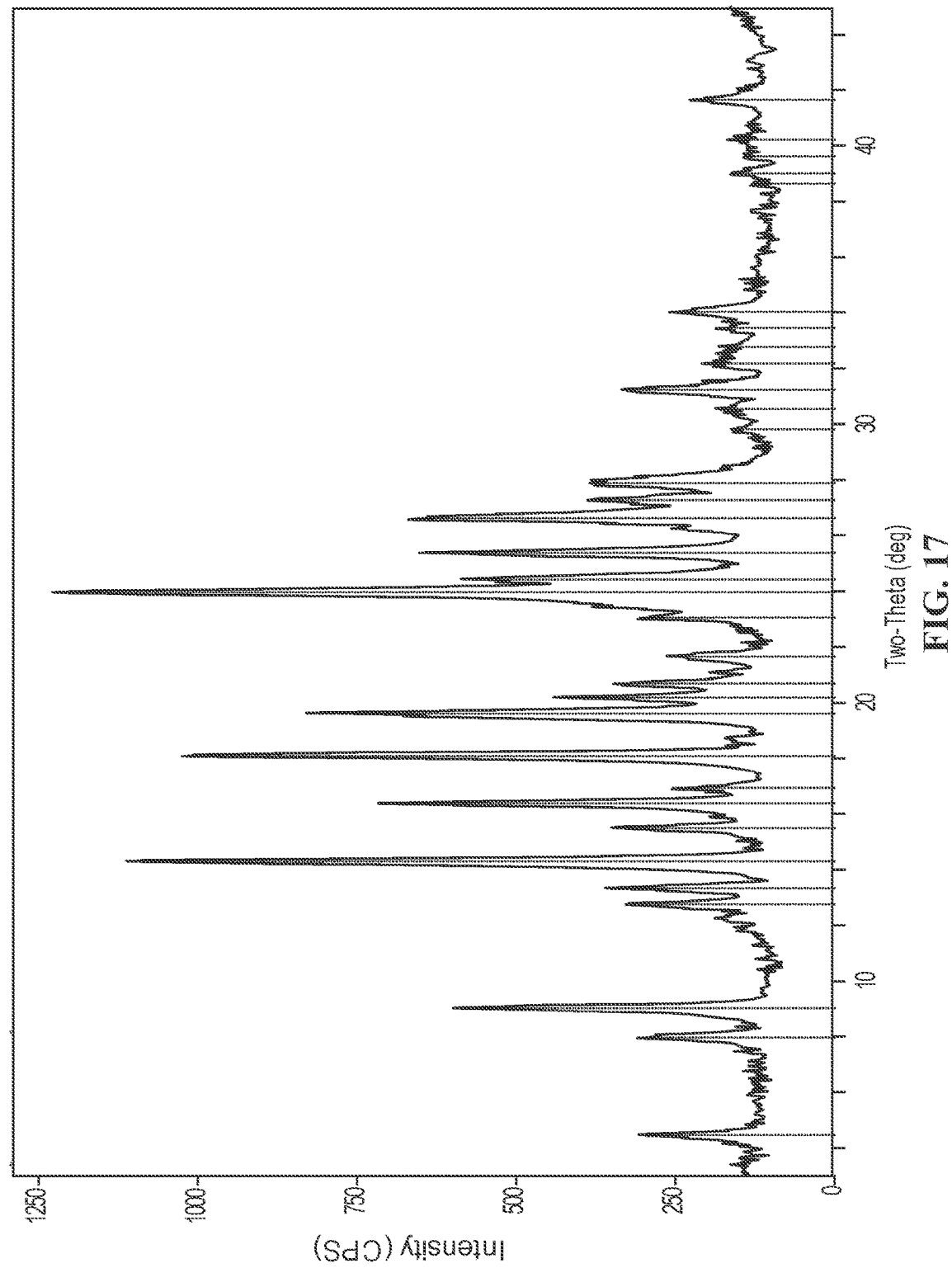
FIG. 17 shows an XRPD pattern of Compound 1, Form VIII.

In some embodiments, Form VIII has an XRPD pattern with characteristic peaks as substantially shown in FIG. 17.

Figure 18:
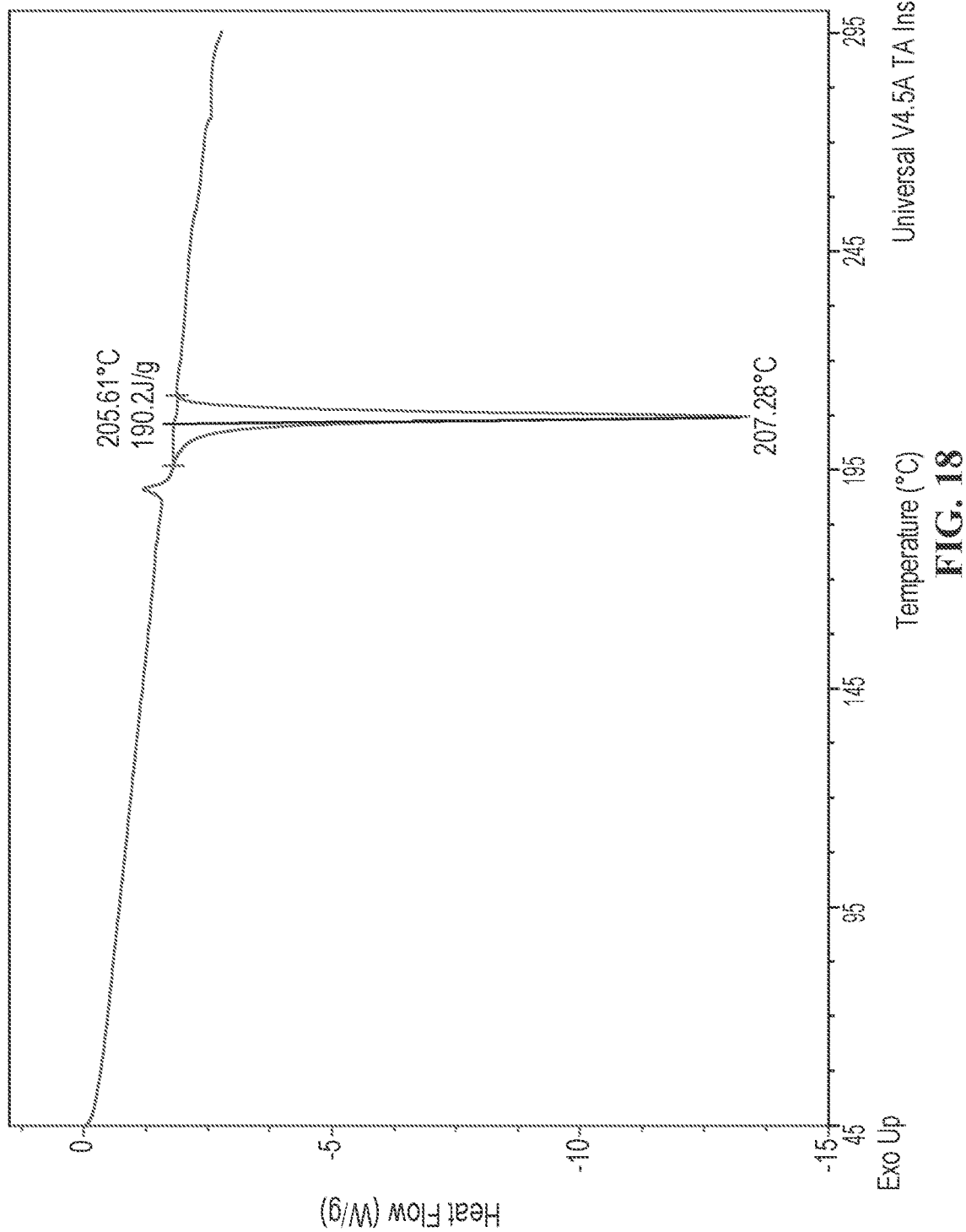
FIG. 18 shows a DSC thermogram of Compound 1, Form VIII.
Figure 19:
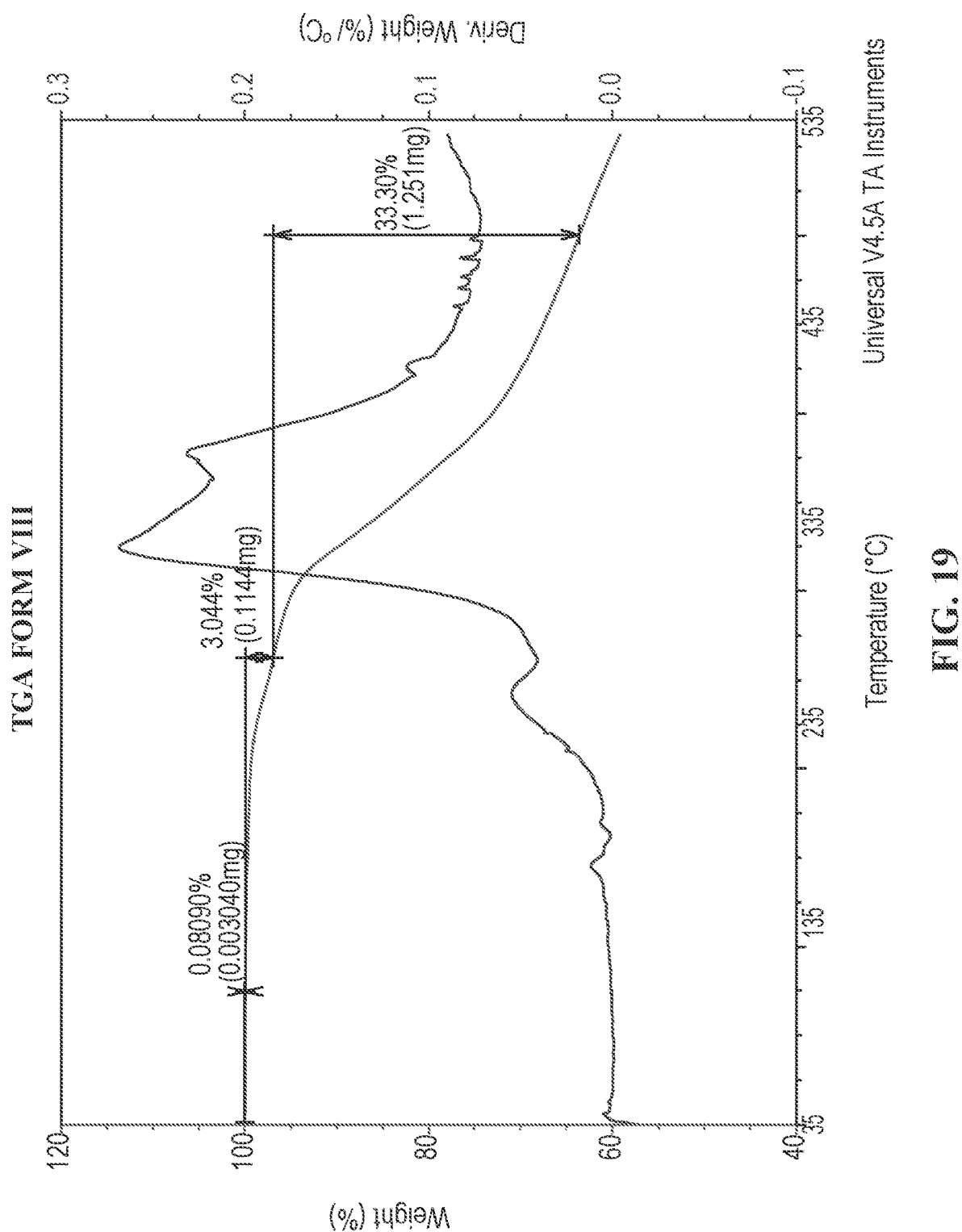
FIG. 19 shows a TGA thermogram of Compound 1, Form VIII.

In some embodiments, Form VIII exhibits a DSC thermogram having an endotherm peak at a temperature of about 207° C. In some embodiments, Form VIII has a DSC thermogram substantially as depicted in FIG. 18. In some embodiments, Form VIII has a TGA thermogram substantially as depicted in FIG. 19.

In some embodiments, Form VIII has one or more characteristic XRPD peaks selected from about 4.5, about 8.0, and about 9.0 degrees 2-theta; and exhibits a DSC thermogram having an endotherm peak at a temperature of about 207° C.

In some embodiments, Form VIII has at least one characteristic XRPD peaks selected from about 4.5, about 8.0, about 9.0, about 12.7, about 13.3, about 14.3, about 15.5, about 16.4, and about 18.1 degrees 2-theta; and exhibits a DSC thermogram having an endotherm peak at a temperature of about 207° C.

In some embodiments, Form VIII has an XRPD pattern substantially as depicted in FIG. 17 and a DSC thermogram substantially as depicted in FIG. 18.

In some embodiments, Form VIII can be isolated with a purity of at least about 80%, about 85%, about 90%, about 95%, about 96%, about 97%, about 98%, or about 99%. In some embodiments, Form VIII can be isolated with a purity greater than about 99%.

Compound 1 Form IX

Provided herein is a solid form of Compound 1 having Form IX, which is described below in the Examples. In some embodiments, Form IX has one or more characteristic XRPD peaks selected from about 6.4, about 8.0, and about 9.6 degrees 2-theta.

In some embodiments, Form IX has at least one characteristic XRPD peaks selected from about 6.4, about 8.0, about 9.6, about 13.3, about 15.3, about 16.0, and about 17.9 degrees 2-theta.

In some embodiments, Form IX has at least two characteristic XRPD peaks selected from about 6.4, about 8.0, about 9.6, about 13.3, about 15.3, about 16.0, about 17.9, about 18.7, about 19.7, about 20.5, about 22.4, about 23.3, about 24.2 degrees 2-theta.

In some embodiments, Form IX has at least three characteristic XRPD peaks selected from about 6.4, about 8.0, about 9.6, about 13.3, about 15.3, about 16.0, about 17.9, about 18.7, about 19.7, about 20.5, about 22.4, about 23.3, about 24.2 degrees 2-theta.

Figure 20:
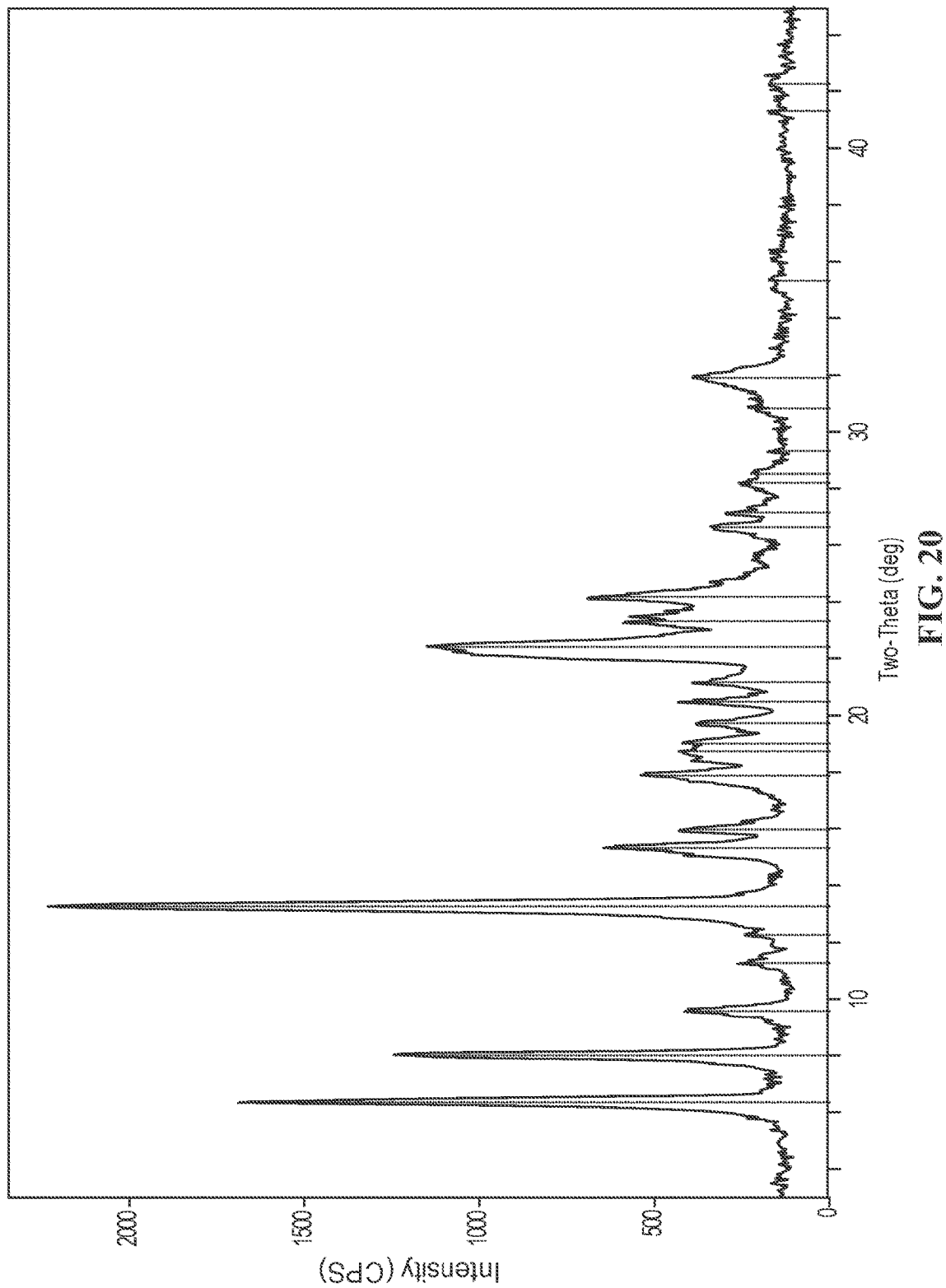
FIG. 20 shows an XRPD pattern of Compound 1, Form IX.

In some embodiments, Form IX has an XRPD pattern with characteristic peaks as substantially shown in FIG. 20.

Figure 21:
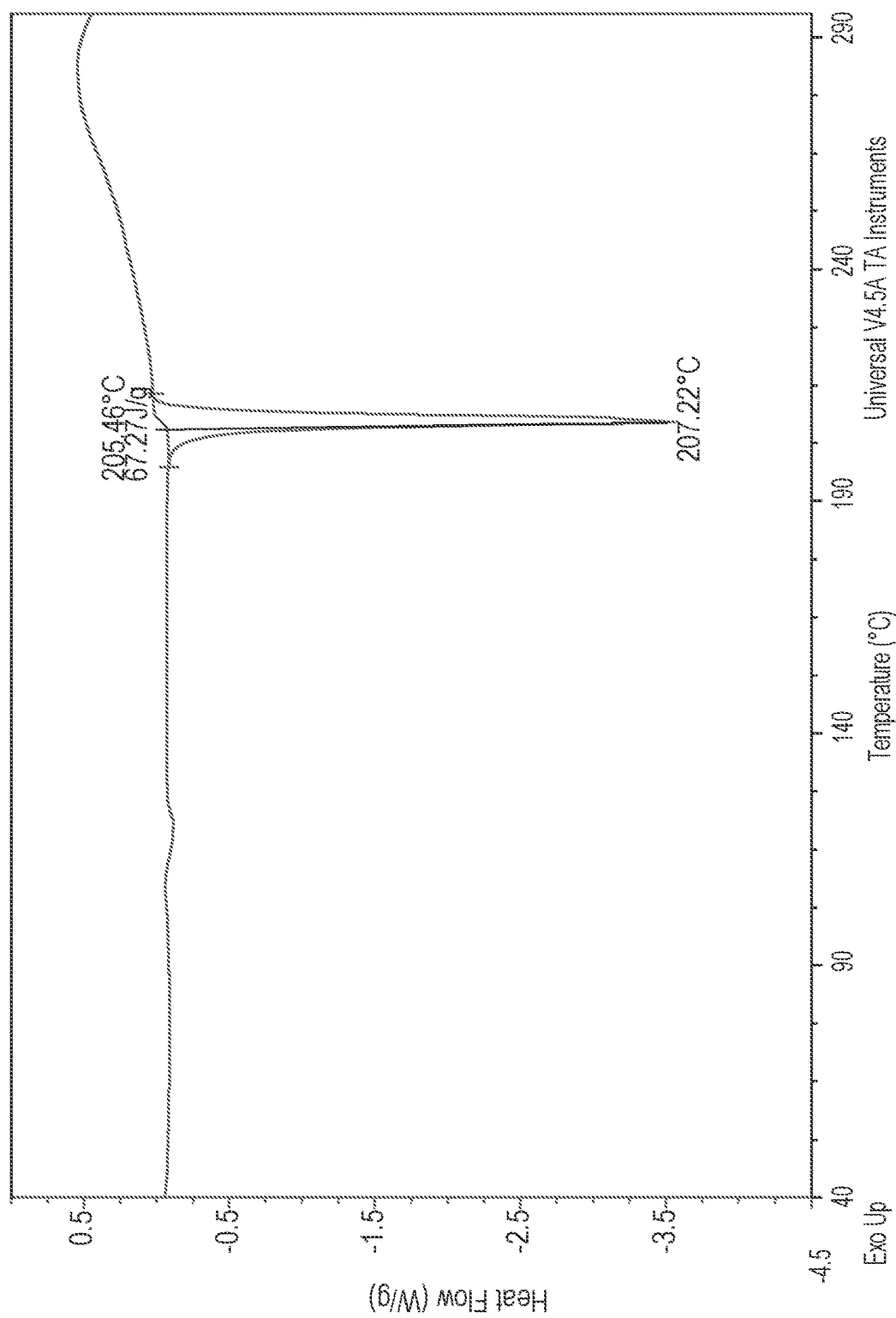
FIG. 21 shows a DSC thermogram of Compound 1, Form IX.
Figure 22:
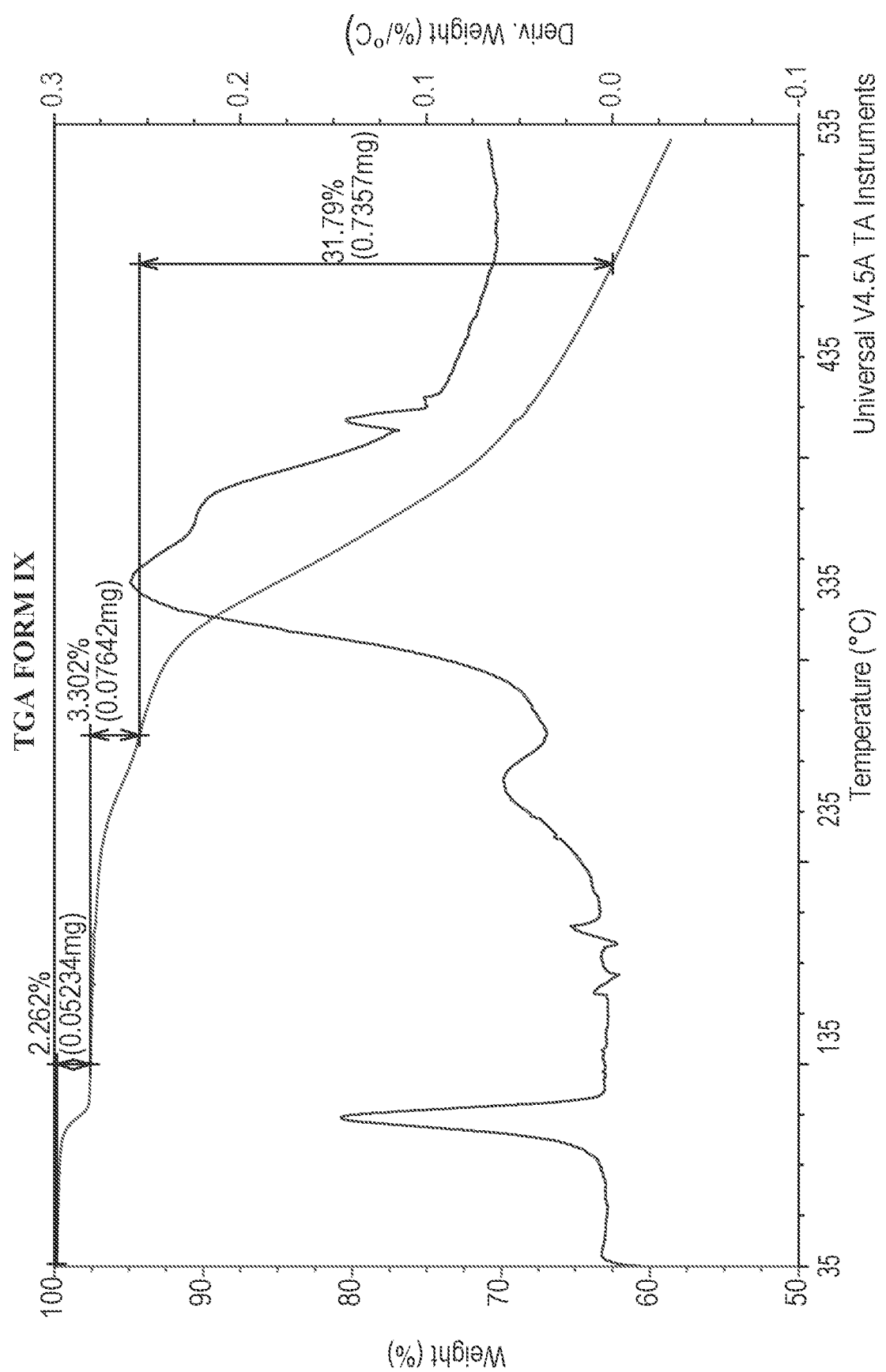
FIG. 22 shows a TGA thermogram of Compound 1, Form IX.

In some embodiments, Form IX exhibits a DSC thermogram having an endotherm peak at a temperature of about 207° C. In some embodiments, Form IX has a DSC thermogram substantially as depicted in FIG. 21. In some embodiments, Form IX has a TGA thermogram substantially as depicted in FIG. 22.

In some embodiments, Form IX has one or more characteristic XRPD peaks selected from about 6.4, about 8.0, and about 9.6 degrees 2-theta; and exhibits a DSC thermogram having an endotherm peak at a temperature of about 207° C.

In some embodiments, Form IX has at least one characteristic XRPD peaks selected from about 6.4, about 8.0, about 9.6, about 13.3, about 15.3, about 16.0, and about 17.9 degrees 2-theta; and exhibits a DSC thermogram having an endotherm peak at a temperature of about 207° C.

In some embodiments, Form IX has an XRPD pattern substantially as depicted in FIG. 20 and a DSC thermogram substantially as depicted in FIG. 21.

In some embodiments, Form IX can be isolated with a purity of at least about 80%, about 85%, about 90%, about 95%, about 96%, about 97%, about 98%, or about 99%. In some embodiments, Form IX can be isolated with a purity greater than about 99%.

Compound 1 Form IXa

Provided herein is a solid form of Compound 1 having Form IXa, which is described below in the Examples. In some embodiments, Form IXa has one or more characteristic XRPD peaks selected from about 6.4, about 8.1, and about 11.3 degrees 2-theta.

In some embodiments, Form IXa has at least one characteristic XRPD peaks selected from about 6.4, about 8.1, about 11.3, about 12.4, about 13.2, about 15.4, about 17.8, and about 19.0 degrees 2-theta.

In some embodiments, Form IXa has at least two characteristic XRPD peaks selected from about 6.4, about 8.1, about 11.3, about 12.4, about 13.2, about 15.4, about 17.8, about 19.0, about 20.5, about 21.3, about 22.8, about 23.3, about 23.9, and about 26.6 degrees 2-theta.

In some embodiments, Form IXa has at least three characteristic XRPD peaks selected from about 6.4, about 8.1, about 11.3, about 12.4, about 13.2, about 15.4, about 17.8, about 19.0, about 20.5, about 21.3, about 22.8, about 23.3, about 23.9, and about 26.6 degrees 2-theta.

Figure 23:
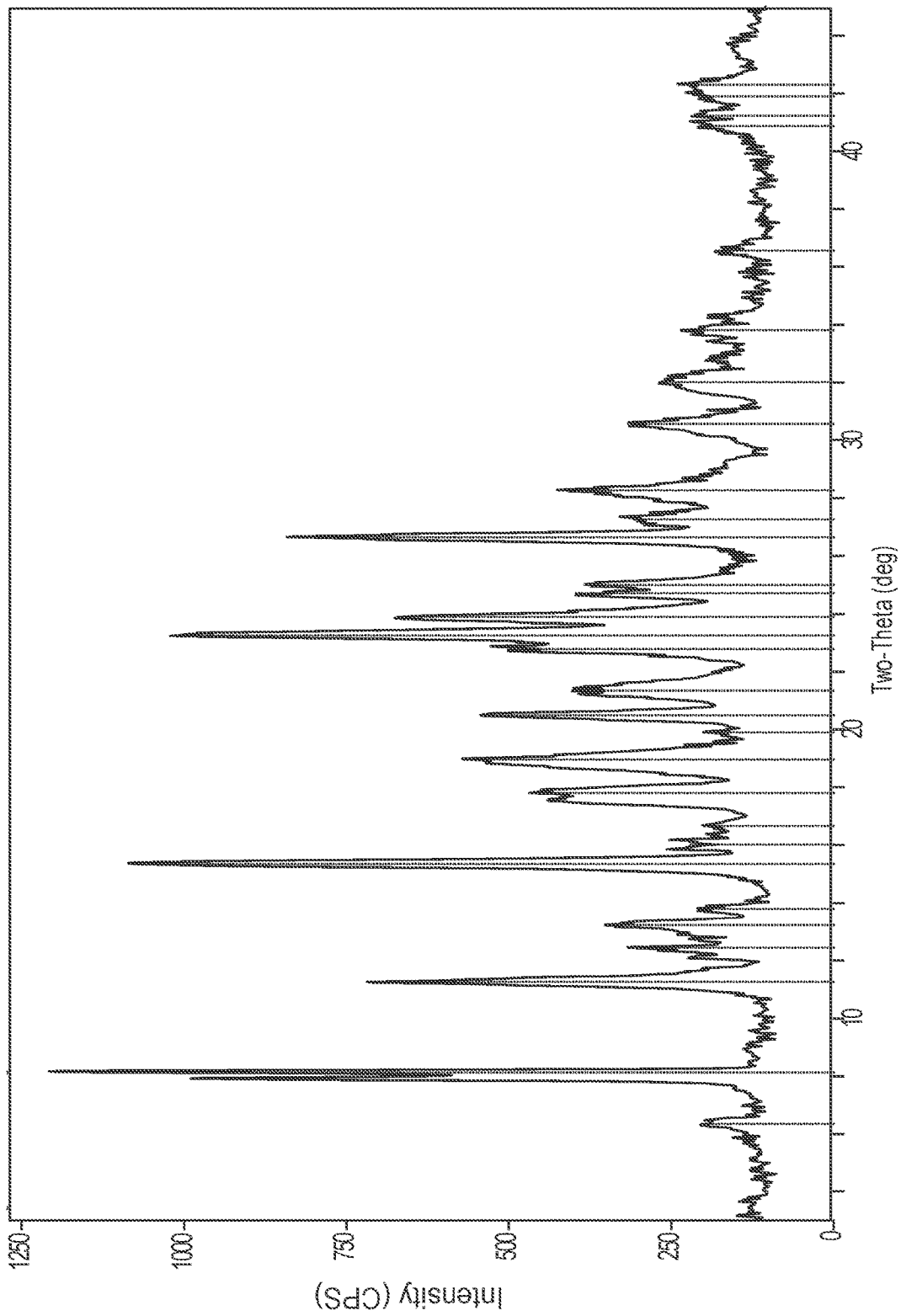
FIG. 23 shows an XRPD pattern of Compound 1, Form IXa.

In some embodiments, Form IXa has an XRPD pattern with characteristic peaks as substantially shown in FIG. 23.

Figure 24:
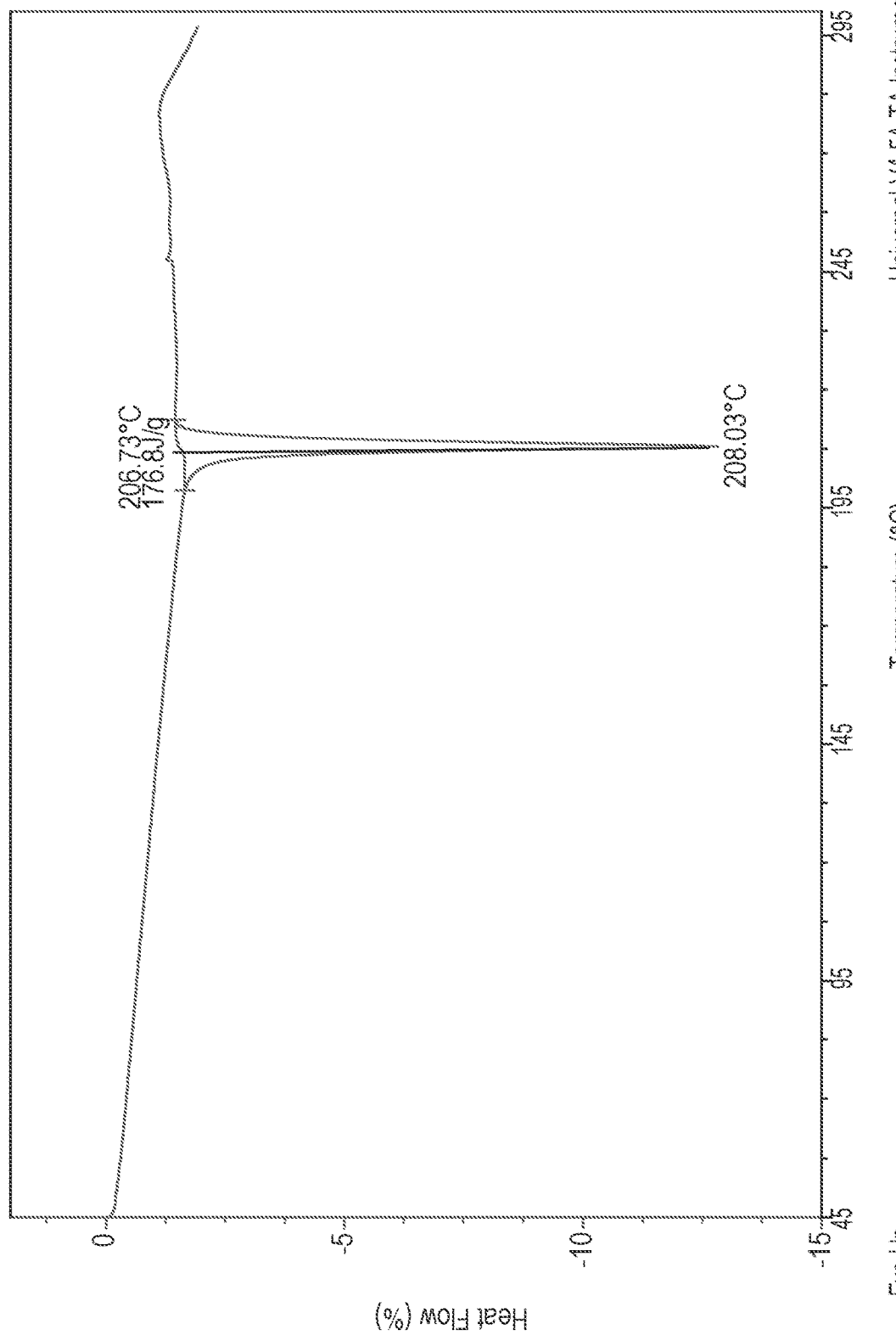
FIG. 24 shows a DSC thermogram of Compound 1, Form IXa.
Figure 25:
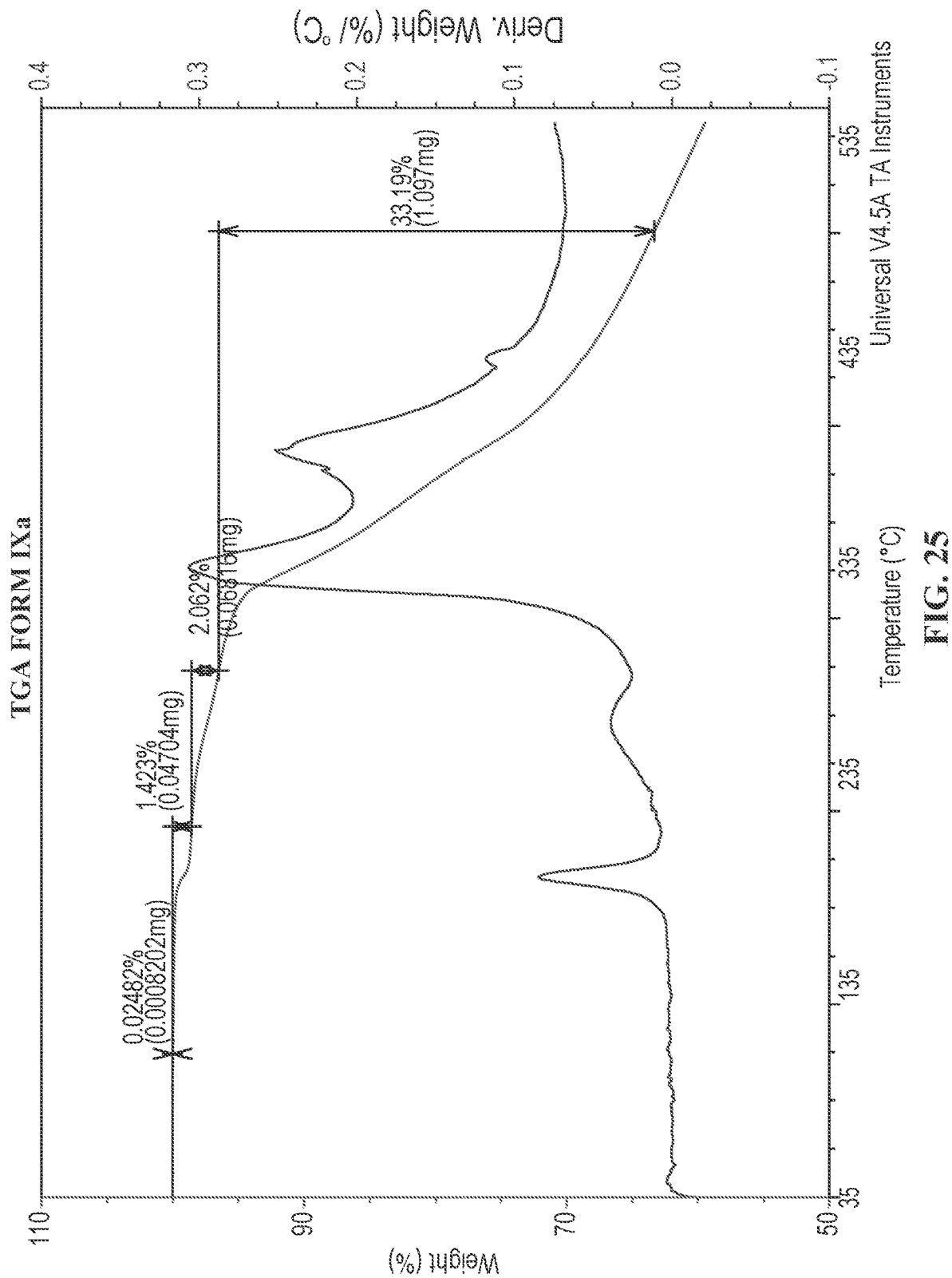
FIG. 25 shows a TGA thermogram of Compound 1, Form IXa.

In some embodiments, Form IXa exhibits a DSC thermogram having an endotherm peak at a temperature of about 208° C. In some embodiments, Form IXa has a DSC thermogram substantially as depicted in FIG. 24. In some embodiments, Form IXa has a TGA thermogram substantially as depicted in FIG. 25.

In some embodiments, Form IXa has one or more characteristic XRPD peaks selected from about 6.4, about 8.1, and about 11.3 degrees 2-theta; and exhibits a DSC thermogram having an endotherm peak at a temperature of about 208° C.

In some embodiments, Form IXa has at least one characteristic XRPD peaks selected from about 6.4, about 8.1, about 11.3, about 12.4, about 13.2, about 15.4, about 17.8, and about 19.0 degrees 2-theta; and exhibits a DSC thermogram having an endotherm peak at a temperature of about 208° C.

In some embodiments, Form IXa has an XRPD pattern substantially as depicted in FIG. 23 and a DSC thermogram substantially as depicted in FIG. 24.

In some embodiments, Form IXa can be isolated with a purity of at least about 80%, about 85%, about 90%, about 95%, about 96%, about 97%, about 98%, or about 99%. In some embodiments, Form IXa can be isolated with a purity greater than about 99%.

Compound 1 Form X

Provided herein is a solid form of Compound 1 having Form X, which is described below in the Examples. In some embodiments, Form X has one or more characteristic XRPD peaks selected from about 4.4, about 6.6, and about 8.2 degrees 2-theta.

In some embodiments, Form X has at least one characteristic XRPD peaks selected from about 4.4, about 6.6, about 8.2, about 8.8, about 12.9, about 21.4, about 22.4, and about 23.3 degrees 2-theta.

In some embodiments, Form X has at least two characteristic XRPD peaks selected from about 4.4, about 6.6, about 8.2, about 8.8, about 12.9, about 16.3, about 21.4, about 22.4, about 23.3, and about 25.8 degrees 2-theta.

In some embodiments, Form X has at least three characteristic XRPD peaks selected from about 4.4, about 6.6, about 8.2, about 8.8, about 12.9, about 16.3, about 21.4, about 22.4, about 23.3, and about 25.8 degrees 2-theta.

Figure 26:
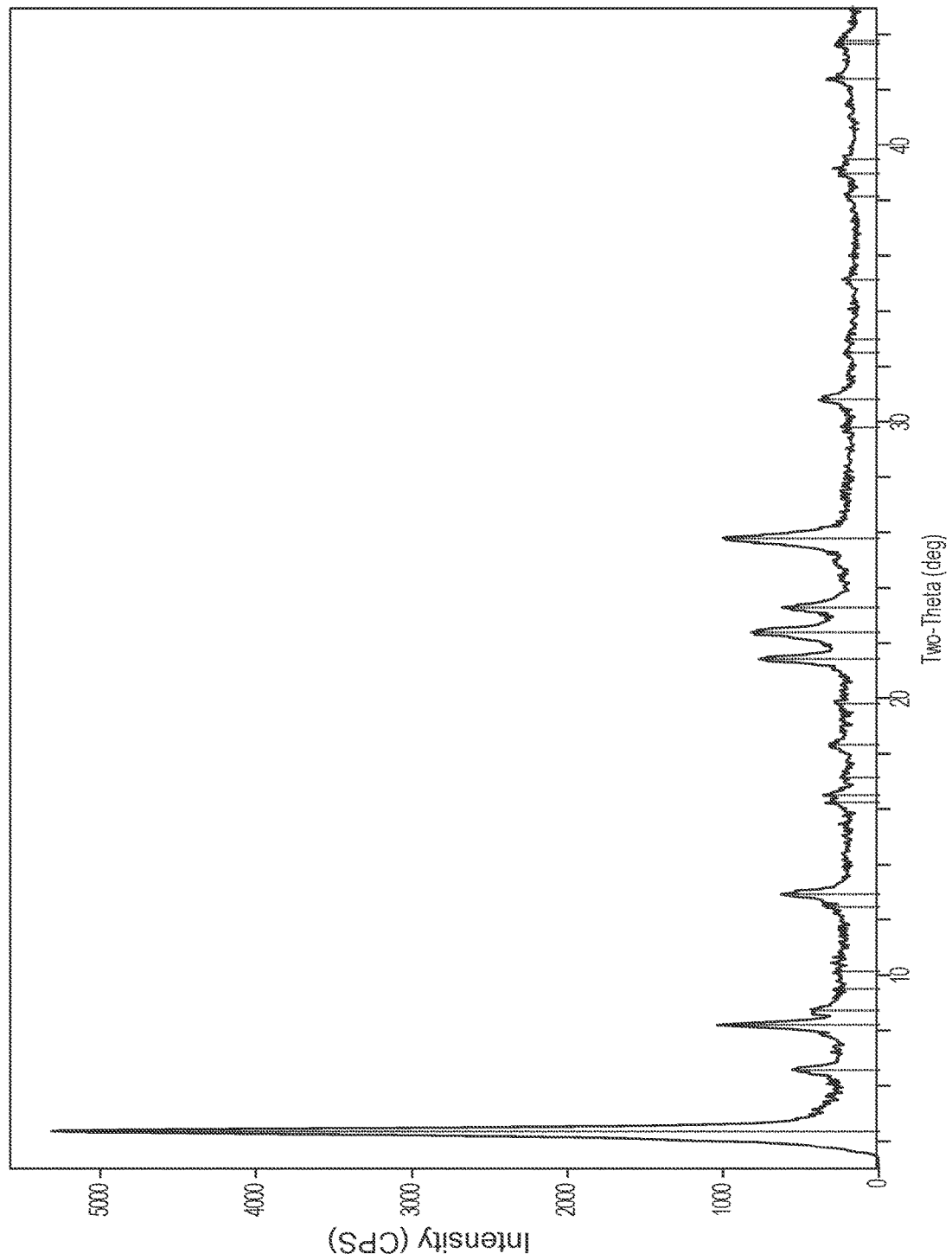
FIG. 26 shows an XRPD pattern of Compound 1, Form X.

In some embodiments, Form X has an XRPD pattern with characteristic peaks as substantially shown in FIG. 26.

In some embodiments, Form X can be isolated with a purity of at least about 80%, about 85%, about 90%, about 95%, about 96%, about 97%, about 98%, or about 99%. In some embodiments, Form X can be isolated with a purity greater than about 99%.

Compound 1 Form XI

Provided herein is a solid form of Compound 1 having Form XI, which is described below in the Examples. In some embodiments, Form XI has one or more characteristic XRPD peaks selected from about 8.2, about 9.8, and about 13.5 degrees 2-theta.

In some embodiments, Form XI has at least one characteristic XRPD peaks selected from about 8.2, about 9.8, about 13.5, about 16.1, about 18.0, and about 22.7 degrees 2-theta.

In some embodiments, Form XI has at least two characteristic XRPD peaks selected from about 8.2, about 9.8, about 13.5, about 16.1, about 18.0, about 18.9, about 19.7, about 20.5, about 22.7, and about 23.6 degrees 2-theta.

In some embodiments, Form XI has at least three characteristic XRPD peaks selected from about 8.2, about 9.8, about 13.5, about 16.1, about 18.0, about 18.9, about 19.7, about 20.5, about 22.7, and about 23.6 degrees 2-theta.

Figure 27:
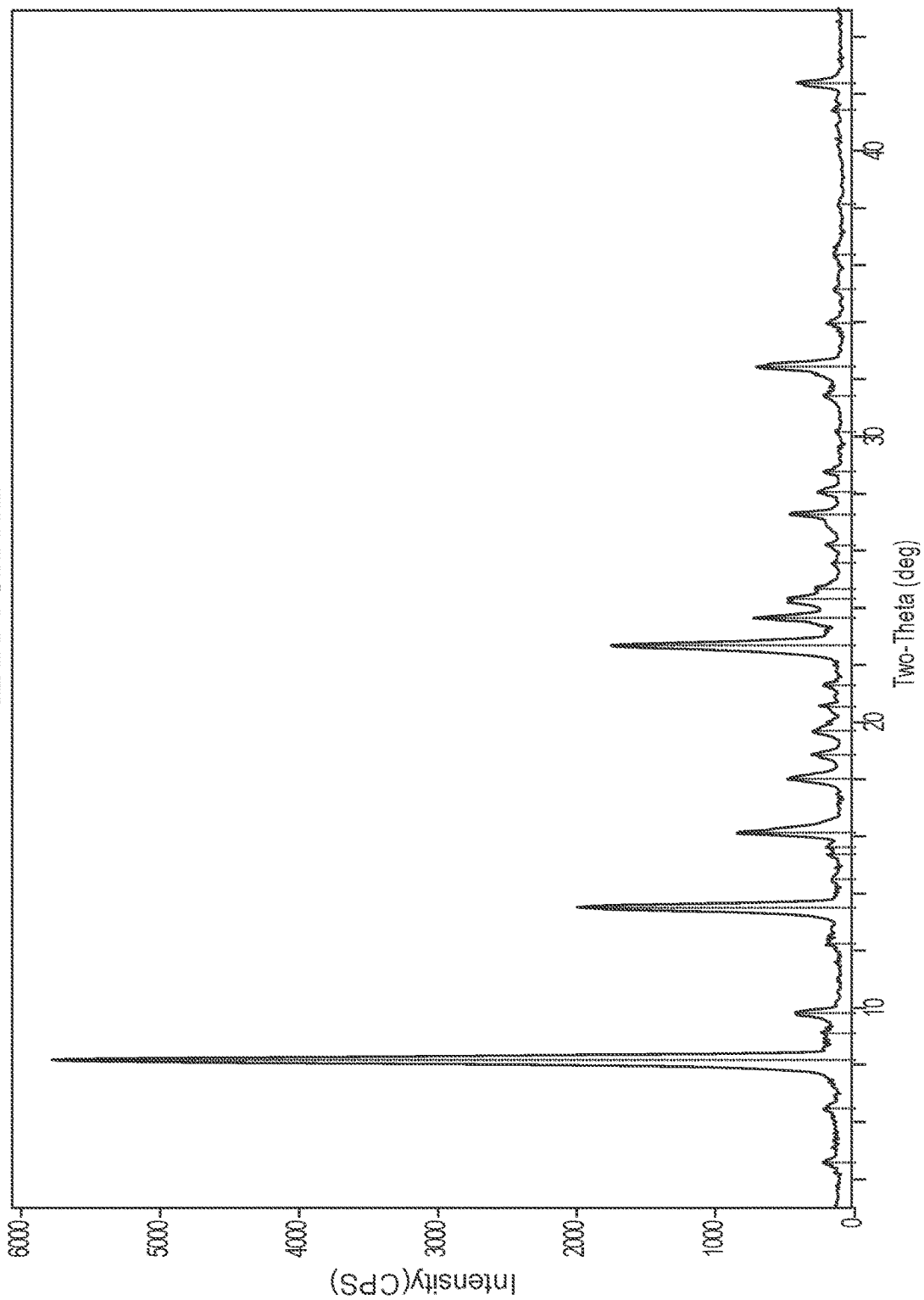
FIG. 27 shows an XRPD pattern of Compound 1, Form XI.

In some embodiments, Form XI has an XRPD pattern with characteristic peaks as substantially shown in FIG. 27.

Figure 28:
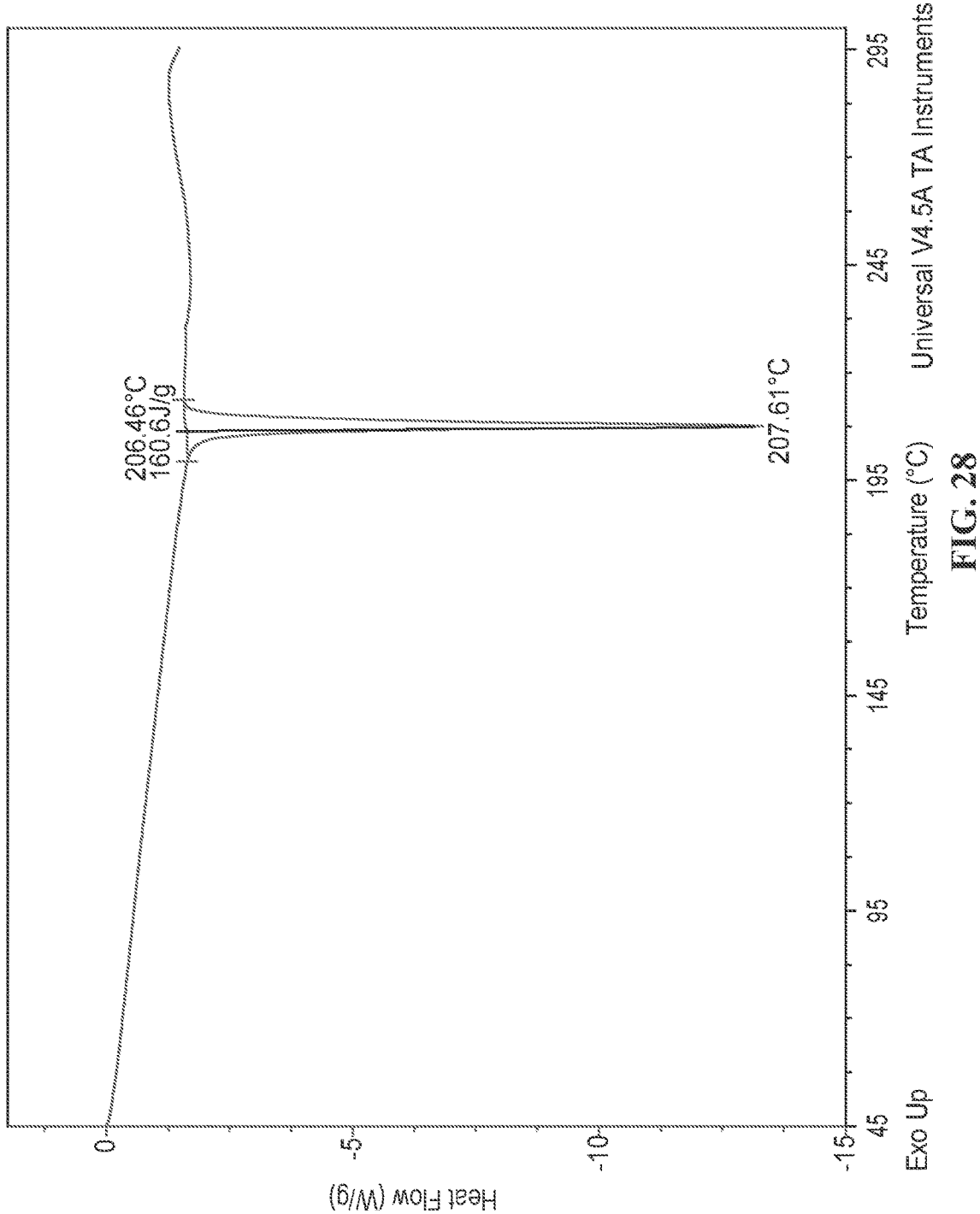
FIG. 28 shows a DSC thermogram of Compound 1, Form XI.
Figure 29:
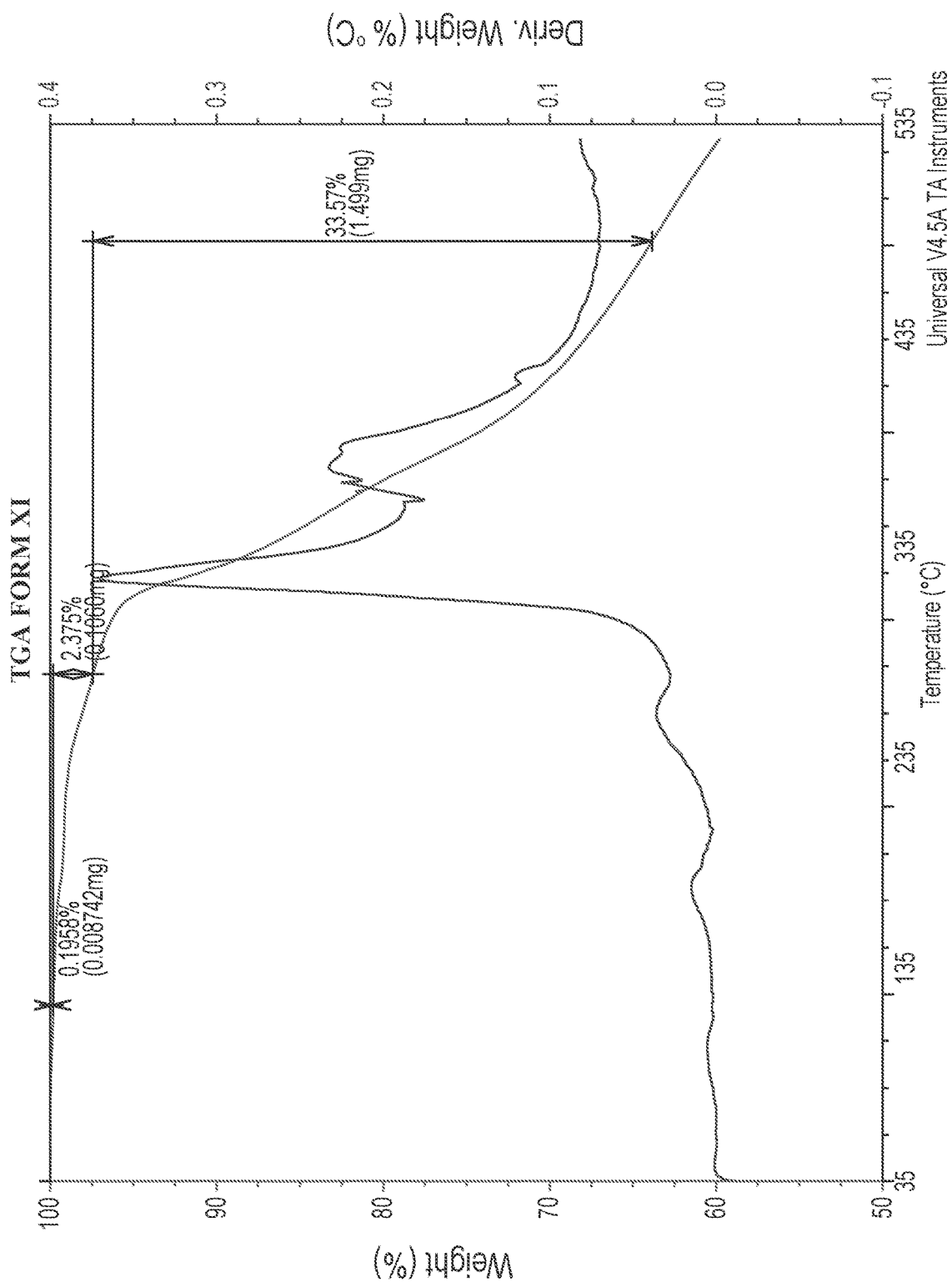
FIG. 29 shows a TGA thermogram of Compound 1, Form XI.

In some embodiments, Form XI exhibits a DSC thermogram having an endotherm peak at a temperature of about 208° C. In some embodiments, Form XI has a DSC thermogram substantially as depicted in FIG. 28. In some embodiments, Form XI has a TGA thermogram substantially as depicted in FIG. 29.

In some embodiments, Form XI has one or more characteristic XRPD peaks selected from about 8.2, about 9.8, and about 13.5 degrees 2-theta; and exhibits a DSC thermogram having an endotherm peak at a temperature of about 208° C.

In some embodiments, Form XI has at least one characteristic XRPD peaks selected from about 8.2, about 9.8, about 13.5, about 16.1, about 18.0, and about 22.7 degrees 2-theta; and exhibits a DSC thermogram having an endotherm peak at a temperature of about 208° C.

In some embodiments, Form XI has an XRPD pattern substantially as depicted in FIG. 27 and a DSC thermogram substantially as depicted in FIG. 28.

In some embodiments, Form XI can be isolated with a purity of at least about 80%, about 85%, about 90%, about 95%, about 96%, about 97%, about 98%, or about 99%. In some embodiments, Form XI can be isolated with a purity greater than about 99%.

Process for Preparation of Compound 1

The present application further provides a process of preparing Compound 1, where the process can be suitable for scale up. A process of preparing Compound 1 is described in US 2016/0244448, the entirety of which is incorporated herein by reference. In comparison to the process described in US 2016/0244448, the process provided herein has certain advantages making it suitable for scale up. For example, the process provided herein affords high yields and good quality products.

In some embodiments, the process for preparing Compound 1:

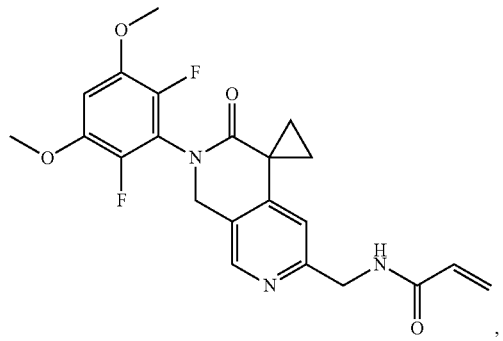

(Compound 1)

or a salt thereof, comprises:
(i) converting Compound 8:

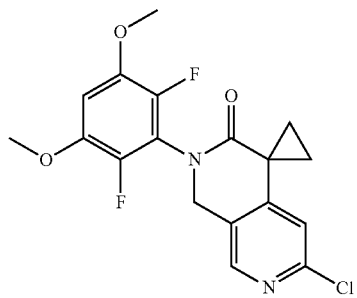

(Compound 8)

to Compound 9:

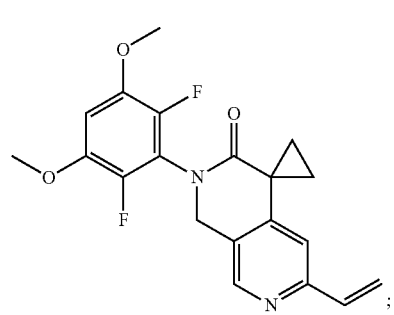

(Compound 9)

(ii) converting Compound 9 to Compound 10:

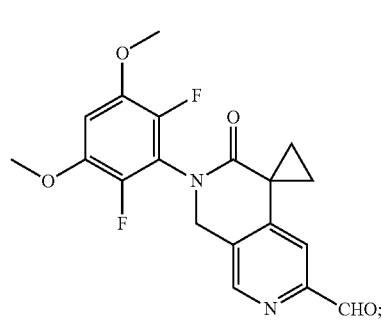

(Compound 10)

(iii) converting Compound 10 to Compound 11:

(Compound 11)

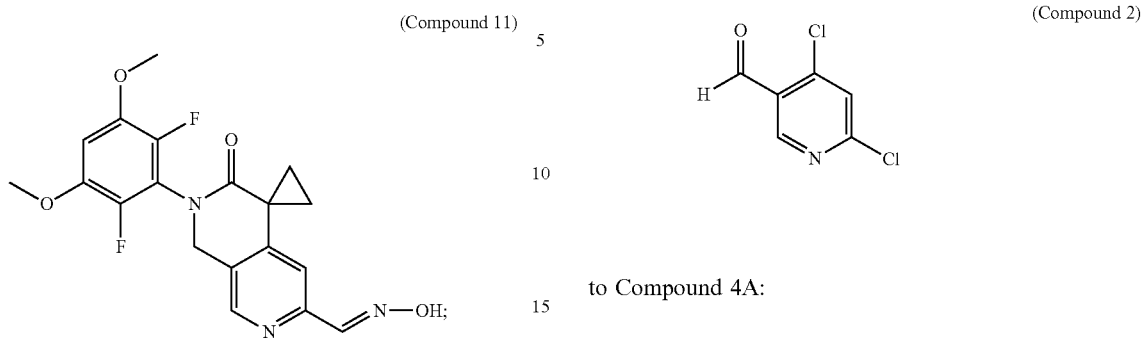

(iv) converting Compound 11 to Compound 12 diacetate:

(Compound 12 diacetate)

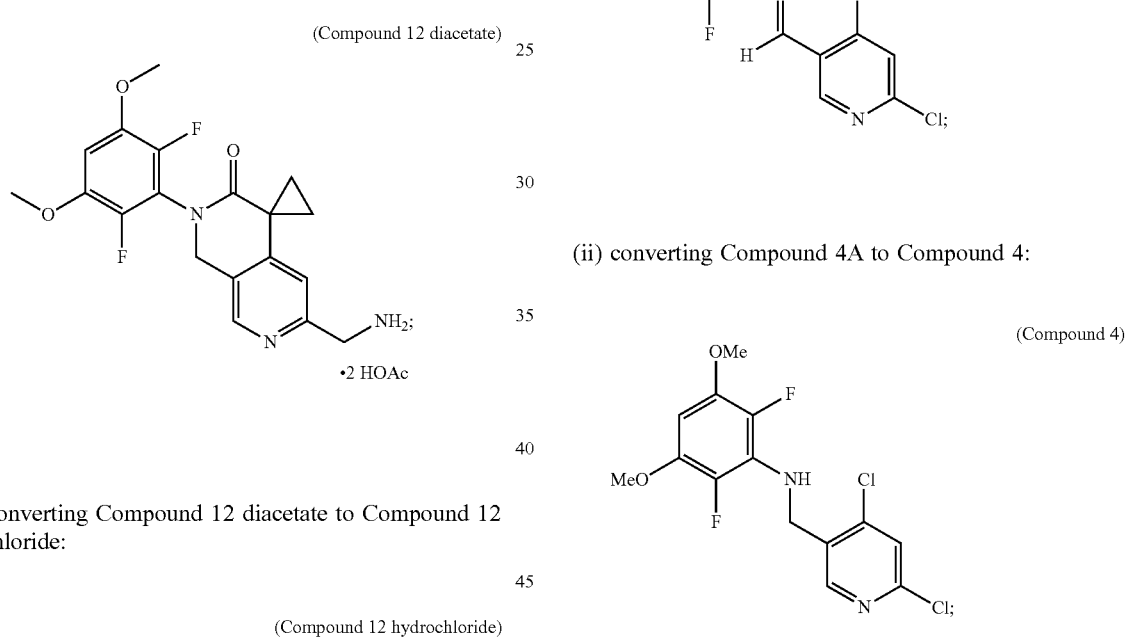

·2 HOAc (v) converting Compound 12 diacetate to Compound 12 hydrochloride:

(Compound 12 hydrochloride)

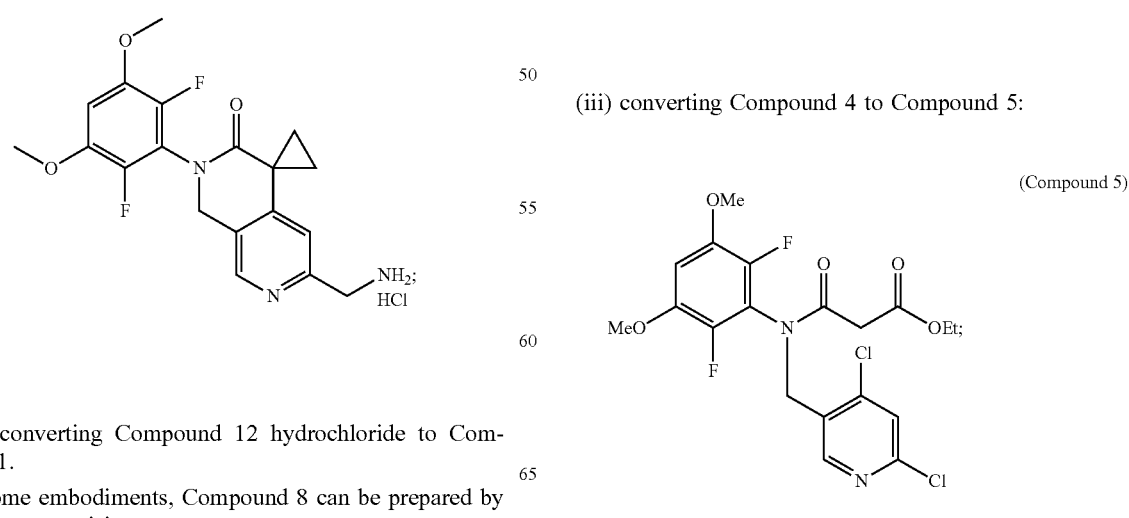

(vi) converting Compound 12 hydrochloride to Compound 1.

In some embodiments, Compound 8 can be prepared by a process comprising:

(i) converting Compound 2:

(Compound 2)

to Compound 4A:

(Compound 4A)

(ii) converting Compound 4A to Compound 4:

(Compound 4)

(iii) converting Compound 4 to Compound 5:

(Compound 5)

(iv) converting Compound 5 to Compound 6:

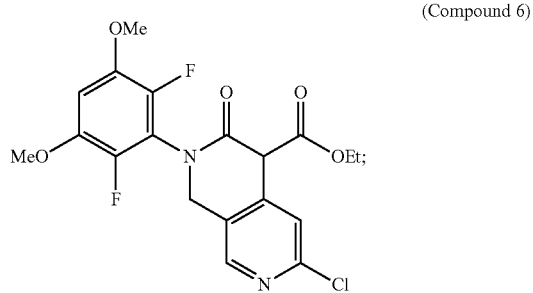 [SMILES: CCOC(=O)C1C(=O)N(c2c(F)c(OC)cc(OC)c2F)Cc2cnc(Cl)cc21]
(Compound 6)

(v) converting Compound 6 to Compound 7:

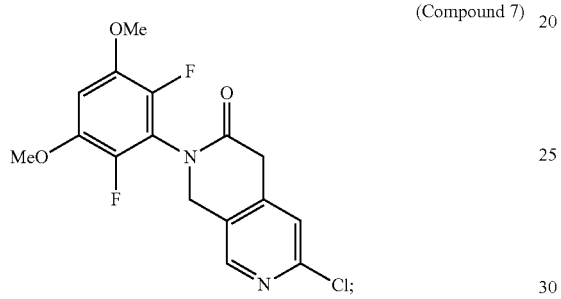
(Compound 7)

(vi) converting Compound 7 to Compound 8.

Provided herein are processes for preparing Compound 1, or a salt thereof, which comprise converting Compound 12 or a salt thereof to Compound 1.

In some embodiments, the salt of Compound 12 is Compound 12 hydrochloride:

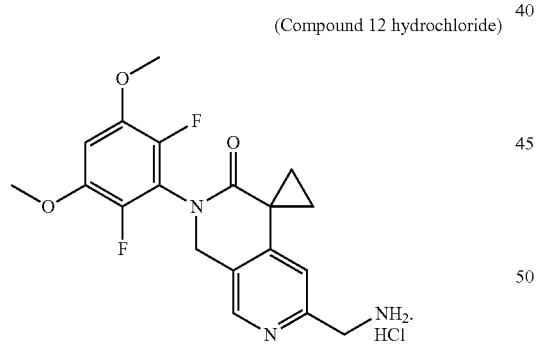
(Compound 12 hydrochloride)

The conversion of Compound 12 hydrochloride to Compound 1 can comprise reacting Compound 12 hydrochloride with acryloyl chloride in the presence of B1 and S1, wherein B1 is a base and S1 is a solvent. For example, B1 is an alkali metal hydroxide base (e.g., sodium hydroxide). In some embodiments, S1 comprises a halogenated solvent (e.g., dichloromethane). The conversion of Compound 12 hydrochloride to Compound 1 can be carried out at a temperature of about 30° C. or lower (e.g., about −10° C. to about 10° C., or about 0° C. to about 10° C.). In some embodiments, about 2 to about 4 equivalents (e.g, about 3 equivalents) of B1 is used based on 1 equivalent of Compound 12 hydrochloride. In some embodiments, about 1 to about 1.5 equivalents (e.g., about 1 equivalent) of acryloyl chloride is used based on 1 equivalent of Compound 12 hydrochloride.

In some embodiments, Compound 12 hydrochloride can be prepared by a process comprising converting Compound 12 diacetate:

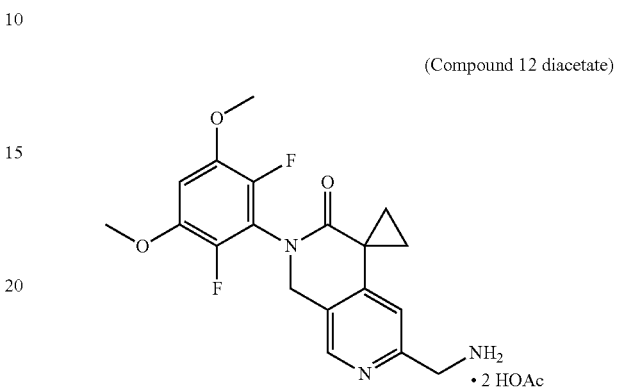
(Compound 12 diacetate)

to Compound 12 hydrochloride.

The conversion of Compound 12 diacetate to Compound 12 hydrochloride can comprise reacting Compound 12 diacetate with B2 and hydrochloric acid in the presence of S2, wherein B2 is a hydroxide base and S2 is a solvent. For example, B2 is an alkali metal hydroxide base such as sodium hydroxide and ammonium hydroxide. In some embodiments, S2 comprises a halogenated solvent, protic solvent, or a mixture thereof. For example, S2 comprises dichloromethane, water, or a mixture thereof.

In some embodiments, Compound 12 diacetate can be prepared by a process comprising converting Compound 11:

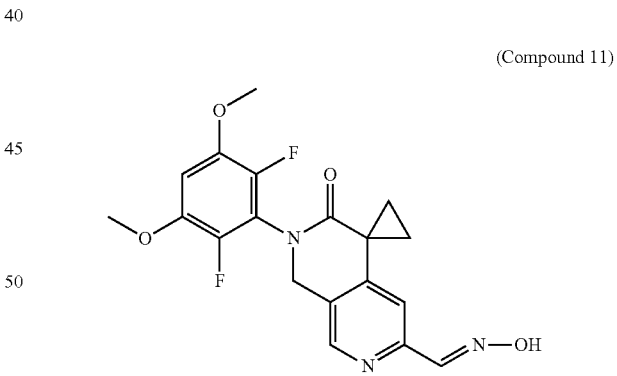
(Compound 11)

to Compound 12 diacetate.

The conversion of Compound 11 to Compound 12 diacetate can comprise reacting Compound 11 with acetic acid and zinc. In some embodiments, the conversion of Compound 11 to Compound 12 diacetate is carried out at a temperature of about 10° C. to about 30° C. (e.g., about 15° C. to about 25° C.). In some embodiments, about 5 to about 7 equivalents (e.g., about 6 equivalents) of zinc is used based on 1 equivalent of Compound 11.

In some embodiments, Compound 11 can be prepared by a process comprising converting Compound 10:

(Compound 10)

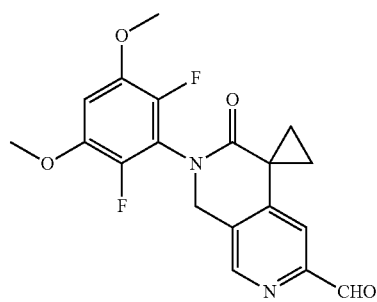

to Compound 11.

In some embodiments, the conversion of Compound 10 to Compound 11 comprises reacting Compound 11 with hydroxylamine hydrochloride in the presence of S3, wherein S3 is a solvent. For example, S3 comprises a protic solvent, a basic solvent, or a mixture thereof. In some embodiments, S3 comprises methanol, pyridine, or a mixture thereof. The conversion of Compound 10 to Compound 11 can be carried out at a temperature of about 45° C. or lower (e.g., about 15° C. to about 45° C.).

In some embodiments, Compound 10 can be prepared by a process comprising converting Compound 9:

(Compound 9)

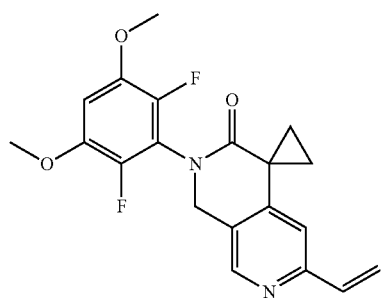

to Compound 10.

The conversion of Compound 9 to Compound 10 can comprise reacting Compound 10 with sodium periodate and osmium tetroxide in the presence of S4, wherein S4 is a solvent. The conversion can further comprise B4, wherein B4 is a base. In some embodiments, B4 is an alkali metal bicarbonate base (e.g., sodium bicarbonate). In some embodiments, S4 comprises an ether solvent, a protic solvent, an aprotic solvent, or a mixture thereof. In some embodiments, S4 comprises tetrahydrofuran, water, ethyl acetate, or a mixture thereof. The conversion can be carried out at a temperature of about 40° C. or lower (e.g., about 10° C. to about 40° C.). In some embodiments, about 3 to about 4 equivalents (e.g., about 3.5 equivalents) of sodium periodate is used based on 1 equivalent of Compound 9. In some embodiments, about 0.05 to about 0.10 equivalent (e.g., about 0.07 equivalent) of osmium tetroxide is used based on 1 equivalent of Compound 9.

In some embodiments, Compound 9 can be prepared by a process comprising converting Compound 8:

(Compound 8)

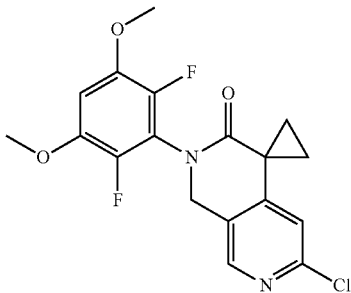

to Compound 9.

In some embodiments, the conversion of Compound 8 to Compound 9 comprises reacting Compound 8 with 4,4,5,5-tetramethyl-2-vinyl-1,3,2-dioxaborolane, P1, and B5 in the presence of S5, wherein P1 is a transition metal catalyst, B5 is a base, and S5 is a solvent. In some embodiments, P1 is a palladium catalyst (e.g., [1,1'-bis(diphenylphosphino)ferrocene]dichloropalladium (II) (Pd(dppf)Cl$_2$)). In some embodiments, B5 is cesium fluoride. In some embodiments, S5 comprises a protic solvent, an ether solvent, or a mixture thereof. In some embodiments, S5 comprises water, 1,4-dioxane, or a mixture thereof. The conversion can be carried out at a temperature of about 80° C. to about 100° C. (e.g., about 85° C. to about 95° C.). In some embodiments, about 3 to about 5 equivalents (e.g., about 4 equivalents) of B5 is used based on 1 equivalent of Compound 8. In some embodiments, about 0.01 to about 0.05 equivalent (about 0.02 equivalent) of P1 is used based on 1 equivalent of Compound 8.

Compound 12 hydrochloride can also be prepared using other processes. For example, Compound 12 hydrochloride can be prepared by a process comprising converting Compound 15:

(Compound 15)

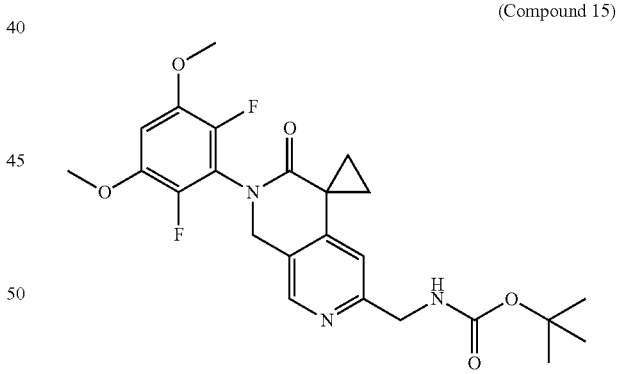

to Compound 12 hydrochloride.

In some embodiments, the conversion of Compound 15 to Compound 12 hydrochloride comprises reacting Compound 15 with hydrochloric acid in the presence of S6, wherein S6 is a solvent. In some embodiments, S6 comprises an aprotic solvent, an ether solvent, or a mixture thereof. In some embodiments, S6 comprises dichloromethane, 1,4-dioxane, or a mixture thereof. In some embodiments, about 5 to about 10 equivalents (about 8 equivalents) of hydrochloric acid is used based on 1 equivalent of Compound 15.

In some embodiments, Compound 15 can be prepared by a process comprising converting Compound 8 to Compound 15.

In some embodiments, the conversion of Compound 8 to Compound 15 comprises reacting Compound 8 with potassium N-Boc-aminomethyltrifluoroborate, P2, and B7, wherein P2 is a transitional metal catalyst and B7 is base. In some embodiments, P2 is a palladium catalyst (e.g., cataCXium Pd G4). In some embodiments, B7 is a carbonate base (e.g., cesium carbonate base). In some embodiments, the conversion is carried out in S7, wherein S7 is a solvent. S7 can comprise a protic solvent, an ether solvent, or a mixture thereof. In some embodiments, S7 comprises water, dioxane, or a mixture thereof. The conversion can be carried out at a temperature of about 80° C. to about 90° C. (e.g., about 85° C.). In some embodiments, about 2 to about 3 equivalents (e.g., about 2.5 equivalents) of N-Boc-aminomethyltrifluoroborate is used based on 1 equivalent of Compound 8. In some embodiments, about 4 to about 5 equivalents (about 4.5 equivalents) of B7 is used based on 1 equivalent of Compound 8. In some embodiments, about 0.01 to about 0.05 equivalent (0.03 equivalent) of P2 is used based on 1 equivalent of Compound 8.

In some embodiments, Compound 15 can be prepared by a process comprising converting Compound 12 diacetate to Compound 15.

In some embodiments, the conversion of Compound 12 diacetate to Compound 15 comprises reacting Compound 12 diacetate with di-tert-butyldicarbonate with B8. In some embodiments, B8 is an alkali metal hydroxide base such as sodium hydroxide. The conversion can be carried out in S8, wherein S8 is a solvent. In some embodiments, S8 comprises a protic solvent, an ether solvent, or a mixture thereof. In some embodiments, S8 comprises water, tetrahydrofuran, or a mixture thereof. In some embodiments, about 2 equivalents of di-tert-butyldicarbonate is used based on 1 equivalent of Compound 12 diacetate. In some embodiments, about 2 to about 4 equivalents (e.g., 3 equivalents) of B8 is used based on 1 equivalent of Compound 12 diacetate.

In some embodiments, Compound 8 can be prepared by a process comprising converting Compound 7:

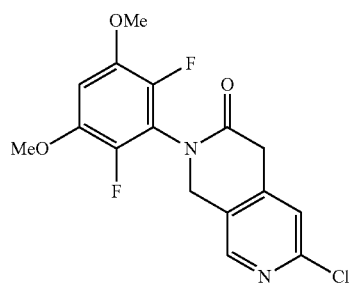

(Compound 7)

to Compound 8.

In some embodiments, the conversion of Compound 7 to Compound 8 comprises reacting Compound 7 with 1-bromo-2-chloroethane and B9, wherein B9 is a base. In some embodiments, B9 is carbonate base (e.g., cesium carbonate). The conversion can be carried out in S9, wherein S9 is a solvent. In some embodiments, S9 comprises an aprotic solvent such as N,N-dimethylformamide. In some embodiments, about 2 equivalents (e.g., about 1.5, about 1.6, about 1.7, about 1.8, about 1.9, or about 2.0 equivalents) of 1-bromo-2-chloroethane is used based on 1 equivalent of Compound 7. In some embodiments, about 1 to about 3 equivalents (2 equivalents) of B9 is used based on 1 equivalent of Compound 7.

In some embodiments, Compound 7 can be prepared by a process comprising converting Compound 6:

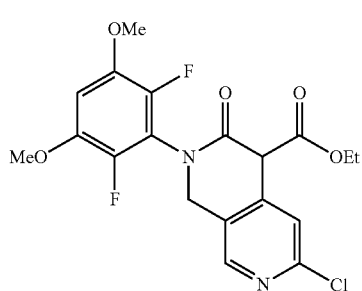

(Compound 6)

to Compound 7.

In some embodiments, the conversion of Compound 6 to Compound 7 comprises reacting Compound 6 with hydrogen chloride. The conversion can be carried out in S10, wherein S10 is a solvent. In some embodiments, S10 comprises a protic solvent, an ether solvent, or a mixture thereof. In some embodiments, S10 comprises water, 1,4-dioxane, or a mixture thereof. The conversion can be carried out at a temperature of about 70° C. to about 90° C. (e.g., about 80° C.). In some embodiments, about 5 to about 15 equivalents (e.g., about 10 equivalents) of hydrogen chloride is used based on 1 equivalent of Compound 6. The conversion of Compound 6 to Compound 7 can be deemed completed as indicated by HPLC. The pH of the reaction mixture can be adjusted to 8 with a solution of sodium hydroxide in water.

In some embodiments, Compound 6 can be prepared by a process comprising converting Compound 5:

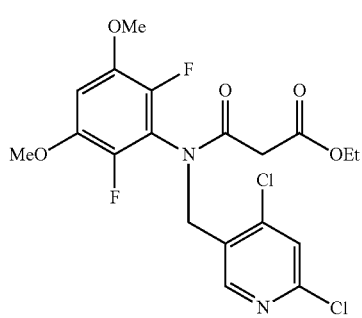

(Compound 5)

to Compound 6.

In some embodiments, the conversion of Compound 5 to Compound 6 comprises reacting Compound 5 with CuI, B11, and 2-pyridinecarboxylic acid, wherein B11 is a base. In some embodiments, B11 is a carbonate base such as cesium carbonate. The conversion can be carried out in S11, wherein S11 is a solvent. In some embodiments, S11 comprises an aprotic solvent such as dimethylsulfoxide. The conversion can be carried out at a temperature of about 110° C. to about 130° C. (e.g., about 120° C.). In some embodiments, about 0.1 to about 0.3 equivalent (e.g., about 0.2 equivalent) of CuI is used based on 1 equivalent of Compound 5. In some embodiments, about 2 to about 4 equivalents (e.g., about 3 equivalents) of B11 is used based on 1 equivalent of Compound 5. In some embodiments, about 0.5 to about 1 equivalent (e.g., about 0.8 equivalent) of 2-pyridinecarboxylic acid is used based on 1 equivalent of Compound 5.

Alternatively, the conversion of Compound 5 to Compound 6 comprises reacting Compound 5 with B12, wherein B12 is a base. In some embodiments, B12 is a phosphate base such as potassium phosphate. In some embodiments, the conversion can be carried out in S12, wherein S12 is a solvent. In some embodiments, S12 comprises an aprotic solvent (e.g., dimethylsulfoxide). In some embodiments, the conversion of Compound 5 to Compound 6 is carried out at a temperature of about 70° C. to about 100° C. (e.g., about 80° C. to about 90° C.). In some embodiments, about 3 to about 4 equivalents (e.g., about 3.5 equivalents) of B12 is used based on 1 equivalent of Compound 5.

In some embodiments, Compound 5 can be prepared by a process comprising converting Compound 4:

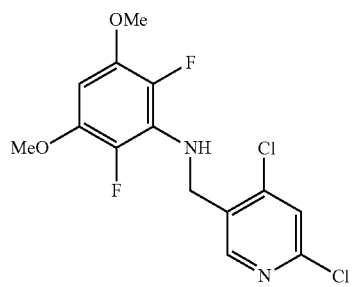

(Compound 4)

to Compound 5.

In some embodiments, the conversion of Compound 4 to Compound 5 comprises reacting Compound 4 with ethyl malonyl chloride and B13, wherein B13 is a base. In some embodiments, B13 is a trimethylamine or sodium bicarbonate. The conversion can be carried out in S13, wherein S13 is a solvent. In some embodiments, S13 comprises an aprotic solvent such as dichloromethane. In some embodiments, about 1 to about 1.5 equivalents (e.g., 1 equivalent) of ethyl malonyl chloride is used based on 1 equivalent of Compound 4. In some embodiments, about 1 to about 2 equivalents (e.g., 1.5 equivalents) of trimethylamine is used based on 1 equivalent of Compound 4. In some embodiments, about 2 to about 4 equivalents (e.g., 3 equivalents) of sodium bicarbonate is used based on 1 equivalent of Compound 4.

In some embodiments, Compound 4 can be prepared by a process comprising converting Compound 4A:

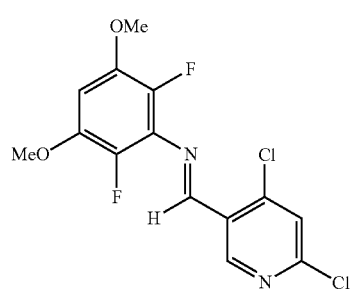

(Compound 4A)

to Compound 4.

In some embodiments, the conversion of Compound 4A to Compound 4 comprises reacting Compound 4A with sodium borohydride. The conversion can be carried out in S14, wherein S14 is a solvent. In some embodiments, S14 comprises a halogenated solvent, a protic solvent, or a mixture thereof. In some embodiments, S14 comprises dichloromethane, methanol, or a mixture thereof. The conversion can be carried out at a temperature of about 5° C. to about 10° C. (e.g., about 8° C.). In some embodiments, about 1 to about 1.5 equivalents (e.g., about 1 equivalent) of sodium borohydride is used based on 1 equivalent of Compound 4A.

In some embodiments, Compound 4A can be prepared by a process comprising converting Compound 2:

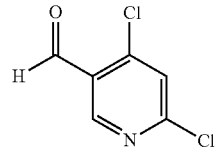

(Compound 2)

to Compound 4A.

In some embodiments, the conversion of Compound 2 to Compound 4A comprises reacting Compound 2 with 2,6-difluoro-3,5-dimethoxyaniline and acetic acid. The conversion can be carried out in S15, wherein S15 is a solvent. In some embodiments, S15 comprises a protic solvent such as ethanol. In some embodiments, about 1 equivalent of 2,6-difluoro-3,5-dimethoxyaniline is used based on 1 equivalent of Compound 2. In some embodiments, about 3 equivalents of acetic acid is used based on 1 equivalent of Compound 2.

Compound 4 can also be prepared starting from Compound 2 without the isolation of Compound 4A. For example, the conversion of Compound 2 to Compound 4A comprises reacting Compound 2 with 2,6-difluoro-3,5-dimethoxyaniline and dibutyltin dichloride. In some embodiments, the conversion of Compound 2 to Compound 4 further comprises phenylsilane. The conversion can be carried out in S16, wherein S16 is a solvent. In some embodiments, S16 comprises an ether solvent (e.g., tetrahydrofuran). In some embodiments, about 1 equivalent of 2,6-difluoro-3,5-dimethoxyaniline is used based on 1 equivalent of Compound 2. In some embodiments, about 0.1 to about 0.3 equivalent (e.g., about 0.2 equivalent) of dibutyltin dichloride is used based on 1 equivalent of Compound 2. In some embodiments, about 1 equivalent of phenylsilane is used based on 1 equivalent of Compound 2.

Alternatively, Compound 4 can be prepared starting from Compound 2 without the isolation of Compound 4A as described below. For example, the conversion of Compound 2 to Compound 4A comprises reacting Compound 2 with 2,6-difluoro-3,5-dimethoxyaniline, TMSCl and borane. The conversion can be carried out in S17, wherein S17 is a solvent. In some embodiments, S17 comprises a protic solvent, an ether solvent, or a mixture thereof. In some embodiments, S17 comprises water, tetrahydrofuran, or a mixture thereof. In some embodiments, about 1 equivalent of 2,6-difluoro-3,5-dimethoxyaniline is used based on 1 equivalent of Compound 2. In some embodiments, about 2 to about 3 equivalents (e.g., about 2.5 equivalents) of TMSCl is used based on 1 equivalent of Compound 2. In some embodiments, about 1 equivalent of borane is used based on 1 equivalent of Compound 2. In some embodiments, the conversion of Compound 2 to Compound 4 further comprises treating a mixture of Compound 2, 2,6-difluoro-3,5-dimethoxyaniline, TMSCL, and borane with ammonium hydroxide.

In some embodiments provided herein is a compound which is (Compound 9)

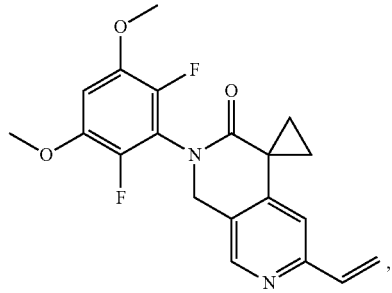

or a salt thereof.

In some embodiments provided herein is a compound which is (Compound 10)

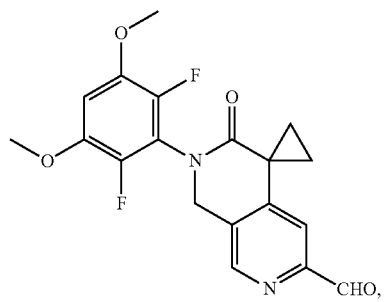

or a salt thereof.

In some embodiments provided herein is a compound which is (Compound 11)

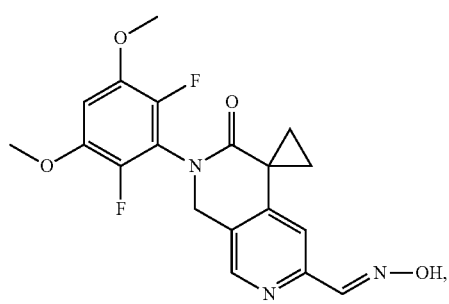

or a salt thereof.

In some embodiments provided herein is a compound which is (Compound 12 diacetate)

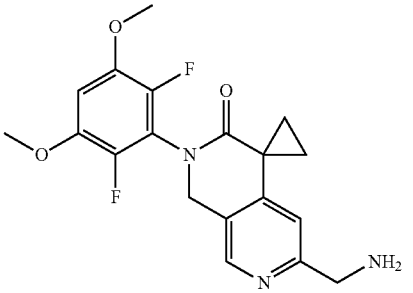

·2 HOAc.

In some embodiments provided herein is a compound which is (Compound 12 hydrochloride)

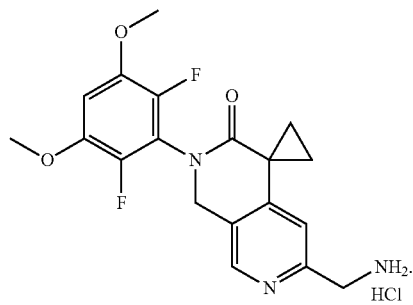

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis*, 4$^{th}$ Ed., John Wiley & Sons: New York, 2006, which is incorporated herein by reference in its entirety.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

In some embodiments, concentrating a solution as described herein refers to a solution where its volume is reduced by letting the solvent evaporate, by heating the solution, by subjecting the solution to reduced pressure, or any combination thereof.

As used herein, the phrase "alkali metal bicarbonate base," employed alone or in combination with other terms, refers to a base having formula M(HCO$_3$), wherein M refers to an alkali metal (e.g. lithium, sodium, or potassium). Example alkali metal bicarbonate bases include, but are not limited to, lithium bicarbonate, sodium bicarbonate, and potassium bicarbonate.

As used herein, the phrase "alkali metal hydroxide base," employed alone or in combination with other terms, refers to a base having formula MOH, wherein M refers to an alkali metal (e.g. lithium, sodium, or potassium). Example alkali metal hydroxide bases include, but are not limited to lithium hydroxide, sodium hydroxide, and potassium hydroxide.

As used herein, the phrase "transition metal catalyst" refers to a metal catalyst (e.g., palladium or nickel catalyst) suitable to catalyze a carbon-carbon coupling reaction. Example transition metal catalysts include, but are not limited to, PdCl$_2$(PPh$_3$)$_2$, Pd(PPh$_3$)$_4$, dichloro(bis {di-tert-butyl[4-(dimethylamino)phenyl]-phosphoranyl})palladium (Pd-132), NiCl$_2$(dppf), and NiCl$_2$(dppp), where (dppf) refers to 1,1'-bis(diphenylphosphino)ferrocene and (dppp) refers to 1,3-bis(diphenylphosphino)propane.

Example palladium catalysts include but are not limited to PdCl$_2$(PPh$_3$)$_2$, Pd(PPh$_3$)$_4$, dichloro(bis {di-tert-butyl[4-(dimethylamino)phenyl]-phosphoranyl})palladium (Pd-132), palladium on carbon, PdCl$_2$, Pd(OAc)$_2$, PdCl$_2$(MeCN)$_2$, tris(dibenzylideneacetone)dipalladium(0) (Pd$_2$(dba)$_3$, 4-(di-tert-butylphosphino)-N,N-dimethylaniline-dichloropalladium (2:1), Pd(dppf)Cl$_2$ (e.g., Pd(dppf)Cl$_2$—CH$_2$Cl$_2$), and tetrakis(tri(o-tolyl)phosphine)palladium(0).

In some embodiments, anti-solvent as described herein refers to a solvent where Compound 1 is less soluble relative to another solvent or solvent mixture in the solution. For example, anti-solvent can include but not limited to benzene, cyclohexane, pentane, hexane, heptane (e.g., n-heptane), toluene, cycloheptane, methylcyclohexane, heptane, ethylbenzene, m-, o-, or p-xylene, octane, indane, nonane, or naphthalene.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane (methylene chloride), tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, tetrahydrofuran (THF), diethyl ether, ethylene glycol dimethyl ether, ethylene glycol diethyl ether, diethylene glycol dimethyl ether (diglyme), diethylene glycol diethyl ether, triethylene glycol dimethyl ether, anisole, tert-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out in air or under an inert atmosphere. Typically, reactions containing reagents or products that are substantially reactive with air can be carried out using air-sensitive synthetic techniques that are well known to the skilled artisan.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

Methods of Use

Compound 1 or solid forms thereof as described herein can inhibit the activity of the FGFR4 enzyme. For example, Compound 1 can be used to inhibit activity of an FGFR4 enzyme in a cell or in an individual or patient in need of inhibition of the enzyme by administering an inhibiting amount of Compound 1 to the cell, individual, or patient.

In some embodiments, Compound 1 is selective for the enzyme FGFR4 over one or more of FGFR1, FGFR2, and/or FGFR3. In some embodiments, Compound 1 is selective for the enzyme FGFR4 over FGFR1, FGFR2, and FGFR3. In some embodiments, Compound 1 is selective for the enzyme FGFR4 over VEGFR2. In some embodiments, the selectivity is 2-fold or more, 3-fold or more, 5-fold or more, 10-fold or more, 25-fold or more, 50-fold or more, or 100-fold or more.

As FGFR4 inhibitors, Compound 1 is useful in the treatment of various diseases associated with abnormal expression or activity of the FGFR4 enzyme or FGFR ligands. Compounds which inhibit FGFR will be useful in providing a means of preventing the growth or inducing apoptosis in tumors, particularly by inhibiting angiogenesis. It is therefore anticipated that Compound 1 will prove useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the FGFR4, or a mutant thereof, activity is inhibited irreversibly. In certain embodiments, FGFR4, or a mutant thereof, activity is inhibited irreversibly by covalently modifying Cys 552 of FGFR4.

In certain embodiments, the disclosure provides a method for treating a FGFR4-mediated disorder in a patient in need thereof, comprising the step of administering to said patient Compound 1, or a pharmaceutically acceptable composition thereof.

For example, Compound 1 or solid forms thereof are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with Compound 1 or solid forms thereof include tumors of the eye, glioblastoma, melanoma, rhabdosarcoma, lymphosarcoma, and osteosarcoma.

Compound 1 or solid forms thereof can also be useful in the inhibition of tumor metastases.

In some embodiments, the present disclosure provides a method for treating hepatocellular carcinoma in a patient in need thereof, comprising the step of administering to said patient Compound 1, or a pharmaceutically acceptable composition thereof.

In some embodiments, the present disclosure provides a method for treating Rhabdomyosarcoma, esophageal cancer, breast cancer, or cancer of a head or neck, in a patient in need thereof, comprising the step of administering to said patient Compound 1, or a pharmaceutically acceptable composition thereof.

In some embodiments, the present disclosure provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR4 enzyme with a compound described herein (e.g., Compound 1) includes the administration of a compound described herein to an individual or patient, such as a human, having FGFR, as well as, for example, introducing a compound described herein (e.g., Compound 1) into a sample containing a cellular or purified preparation containing the FGFR4 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with Compound 1 for treatment of FGFR-associated diseases, disorders or conditions, or diseases or conditions as described herein. The agents can be combined with the present compounds in a single dosage form, or the agents can be administered simultaneously or sequentially as separate dosage forms.

Compound 1 can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Additionally, Compound 1 can be combined with inhibitors of kinases associated with the PIK3/Akt/mTOR signaling pathway, such as PI3K, Akt (including Akt1, Akt2 and Akt3) and mTOR kinases.

In some embodiments, Compound 1 can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, Compound 1 can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, Compound 1 can be used in combination with targeted therapies, including JAK kinase inhibitors (Ruxolitinib, additional JAK1/2 and JAK1-selective, baricitinib or INCB39110), Pim kinase inhibitors (e.g., INCB53914), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors, TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as INCB54329 or INCB57643), LSD1 inhibitors (e.g., INCB59872 or INCB60003), arginase inhibitors (e.g., INCB1158), indoleamine 2,3-dioxygenase inhibitors (e.g., epacadostat, NLG919 or BMS-986205), and PARP inhibiors (e.g., olaparib or rucaparib).

For treating cancer and other proliferative diseases, Compound 1 can be used in combination with chemotherapeutic agents, agonists or antagonists of nuclear receptors, or other anti-proliferative agents. Compound 1 or solid forms thereof can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, baricitinib, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, niraparib, nofetumomab, olaparib, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, rucaparib, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, veliparib, talazoparib and zoledronate.

In some embodiments, Compound 1 can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, Compound 1 can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012, nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anticancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383.

In some embodiments, Compound 1 can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with Compound 1 can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with Compound 1 for the treatment of cancer include chemotherapeutic agents, targeted cancer therapies, immunotherapies or radiation therapy. Compound 1 may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with Compound 1. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compound 1 may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with Compound 1 include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with Compound 1. In some embodiments, the JAK inhibitor is selective for JAK1 over JAK2 and JAK3.

Other suitable agents for use in combination with Compound 1 include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with Compound 1 include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compound 1 may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, Compound 1 as described herein can be administered in the form of pharmaceutical compositions which refers to a combination of Compound 1 as described herein, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, Compound 1 in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of Compound 1. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the Compound 1, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of Compound 1 can vary according to, for example, the particular use for which the treatment is made, the manner of administration of the compound, the health and condition of the patient, and the judgment of the prescribing physician. The proportion or concentration of Compound 1 in a pharmaceutical composition can vary depending upon a number of factors including dosage, chemical characteristics (e.g., hydrophobicity), and the route of administration. For example, Compound 1 can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Compound 1 can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

Example 1

Synthesis of N-((2'-(2,6-difluoro-3,5-dimethoxyphenyl)-3'-oxo-2',3'-dihydro-1'H-spiro[cyclopropane-1,4'-[2,7]naphthyridine]-6'-yl)methyl)acrylamide (Compound 1)

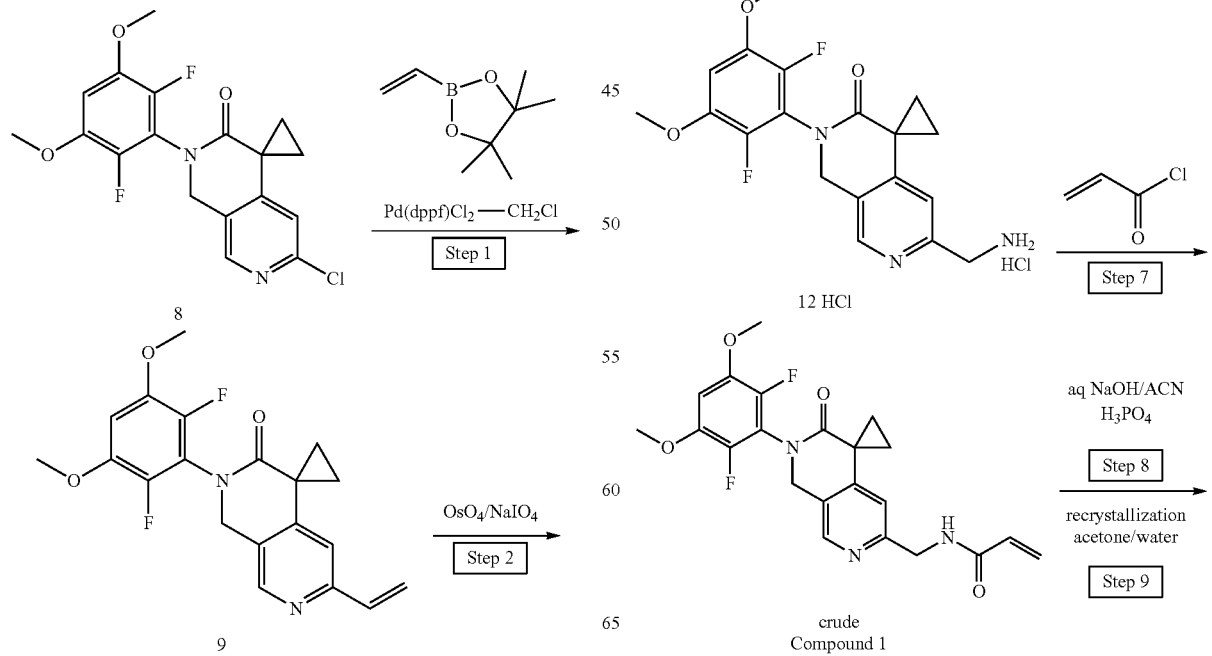

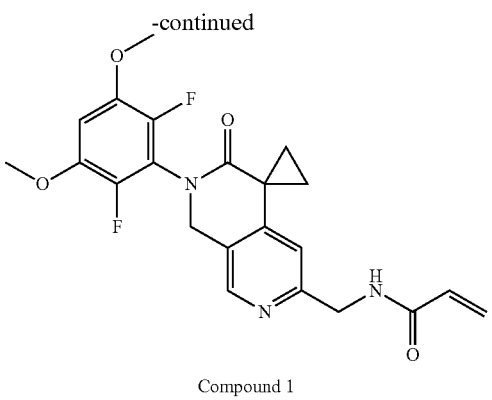

Compound 1

Step 1: 2'-(2,6-Difluoro-3,5-dimethoxyphenyl)-6'-vinyl-1',2'-dihydro-3'H-spiro[cyclo-propane-1,4'-[2,7]naphthyridin]-3'-one (9)

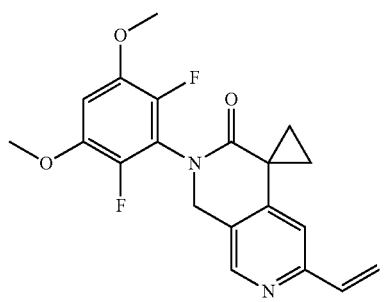 [SMILES: C=Cc1cc2c(cn1)CN(c1c(F)c(OC)cc(OC)c1F)C(=O)C21CC1]

Water (9.5 L), cesium fluoride (CsF, 3.0 kg, 19.75 mol), 1,4-dioxane (8.0 L), 6'-chloro-2'-(2,6-difluoro-3,5-dimethoxyphenyl)-1',2'-dihydro-3'H-spiro[cyclopropane-1,4'-[2,7]naphthyridin]-3'-one (2000 g, 5.25 mol) and 4,4,5,5-tetramethyl-2-vinyl-1,3,2-dioxaborolane (971 g, 6.30 mol) were charged sequentially to a reactor with agitation. After the mixture was purged with nitrogen, [1,1'-bis(diphenylphosphino)ferrocene]dichloropalladium (II), complex with dichloromethane (Pd(dppf)Cl₂—CH₂Cl₂) (64 g, 0.08 mol) was charged to the reactor. After the reaction mixture was purged with nitrogen, it was heated to 85-95° C. and agitated at this temperature until reaction completion was indicated by HPLC. The reaction mixture was concentrated by vacuum distillation, then cooled to approximately 40-50° C. Water (8.0 L) was charged to the reaction mixture. The mixture was cooled to 15-30° C. and stirred for no less than 1 hour. The solids were filtered, washed with n-heptane (10.0 L), partially dried to provide the desired compound (2772 g).

The crude product (7692 g, combined from two batches starting with 5.9 kg of starting chloride) was redissolved in DCM (41.3 L). The water phase was removed and the DCM solution containing the desired product was loaded onto a silica gel column (17.7 kg) with sea sand (5.9 kg) on top of the column. The column was eluted with DCM, followed by a mixture of ethyl acetate (EtOAc) and DCM. The desired fractions were combined and concentrated under reduced pressure to afford the desired compound (5386 g, 93.4% yield). LCMS calculated for $C_{20}H_{19}F_2N_2O_3[M+H]^+$: 373.14; Found: 373.2; $^1$H NMR (300 MHz, CDCl₃) δ 8.32 (s, 1H), 6.80-6.60 (m, 3H), 6.18 (m, 1H), 5.45 (m, 1H), 4.95 (s, 2H), 3.90 (s, 6H), 2.0 (m, 2H), 1.35 (m, 2H).

Steps 2 and 3: (E)-2'-(2,6-difluoro-3,5-dimethoxyphenyl)-3'-oxo-2',3'-dihydro-1'H-spiro-[cyclopropane-1,4'-[2,7]naphthyridine]-6'-carbaldehyde oxime (11)

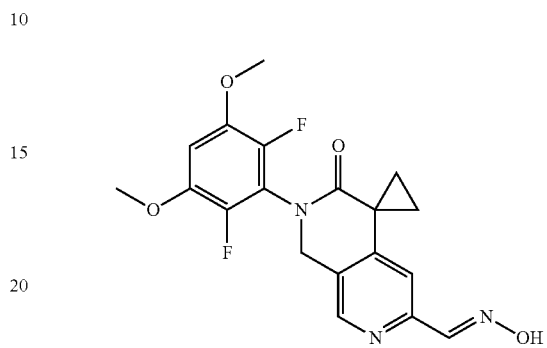

To a solution of 2'-(2,6-Difluoro-3,5-dimethoxyphenyl)-6'-vinyl-1',2'-dihydro-3'H-spiro[cyclo-propane-1,4'-[2,7]naphthyridin]-3'-one (1700 g, 4.57 mol) in tetrahydrofuran (THF, 30.1 L), were charged sodium periodate (NaIO₄, 3476 g, 16.25 mol) and water (8.7 L). A solution of osmium tetroxide (OsO₄, 80 g, 0.32 mol) in THF (300 mL) was charged in portions to the reactor while maintaining the reaction temperature below 40° C. The reaction was agitated at approximately 10-40° C. until reaction completion was indicated by HPLC. If necessary, additional OsO4 in THF may be added. Ethyl acetate (EtOAc, 8.5 L) was charged to the reactor followed by sodium bicarbonate (NaHCO₃, 1534 g, 18.26 mol) in portions with agitation to adjust the pH of the resulting mixture to 6-8. The reaction mixture was filtered to remove solids. The reactor and filter cake were rinsed with additional EtOAc (17.0 L). The filtrate and rinsings containing the desired product were charged back to the reactor and the phases were separate. The organic phase was washed sequentially with aqueous NaHCO₃ (238 g in 3.4 L water) and water (3.4 L). To the organic solution, with agitation, hydroxylamine hydrochloride (698 g, 10.04 mol) was added in portions, followed by pyridine (1.1 L) and a methanol (0.9 L) rinse, maintaining the temperature below 40° C. The reaction mixture was agitated at approximately 15-45° C. until reaction completion is indicated by HPLC. Methyl t-butyl ether (MTBE, 8.2 L) was added to the reactor and the reaction mixture was cooled to approximately 0-10° C. and stirred at this temperature for no less than 1 hour. The precipitated solid was filtered, washed with MTBE (5.4 L), dried to give the desired compound (1233.0 g).

The filtrate and MTBE rinse were combined and concentrated under reduced pressure. The residue was transferred to a reactor using MeOH (6.1 L). The mixture was cooled and stirred for no less than 1 hour. The precipitated solids were filtered, washed with MTBE (4.3 L) and dried to afford additional desired compound (439.6 g). Total amount of solids: 1672.6 g (94% yield) for two crops. LCMS calculated for $C_{19}H_{18}F_2N_3O_4[M+H]^+$: 390.13; Found: 390.1; $^1$H NMR (300 MHz, DMSO-d₆) δ 11.60 (s, 1H), 8.42 (s, 1H), 8.05 (s, 1H), 7.22 (s, 1H), 7.06 (m, 1H), 4.96 (s, 2H), 3.88 (s, 6H), 1.75 (m, 2H), 1.49 (m, 2H).

Step 4: 6'-(aminomethyl)-2'-(2,6-difluoro-3,5-dimethoxyphenyl)-1'H-spiro[cyclopropane-1,4'-[2,7]naphthyridin]-3'(2'H)-one diacetate (12 diacetate)

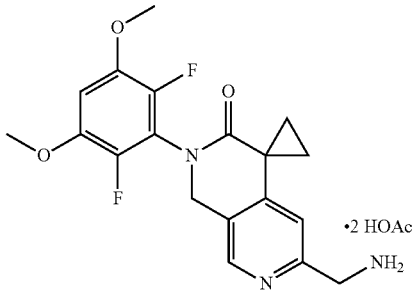

To an agitated mixture of (E)-2'-(2,6-difluoro-3,5-dimethoxyphenyl)-3'-oxo-2',3'-dihydro-1'H-spiro-[cyclopropane-1,4'-[2,7]naphthyridine]-6'-carbaldehyde oxime (1700 g, 4.37 mol) and acetic acid (HOAc, 42.5 L) cooled to approximately 15-25° C., was charged zinc (Zn, 1656 g, 25.32 mol) powder in portions while maintaining the temperature at or below 25° C. After the reaction was complete as indicated by HPLC, the mixture was filtered through Celite (850 g). The filter cake was rinsed with HOAc (3.4 L). The filtrate and washes were combined and concentrated under reduced pressure, adding n-heptane (17.0 L) to assist the distillation, to afford the desired amine as the diacetate salt, which is used in the next step without further purification.

Steps 5 and 6: 6'-(aminomethyl)-2'-(2,6-difluoro-3,5-dimethoxyphenyl)-1'H-spiro[cyclopropane-1,4'-[2,7]naphthyridin]-3'(2'H)-one hydrochloride (12 HCl)

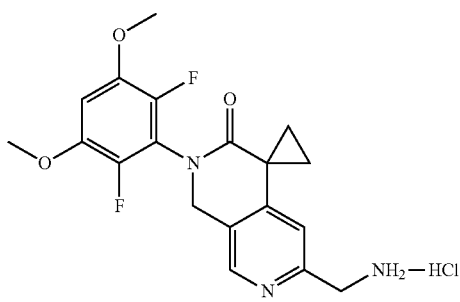 [SMILES: COc1cc(OC)c(F)c(N2Cc3cnc(CNCl)cc3C3(CC3)C2=O)c1F]

To a mixture of 6'-(aminomethyl)-2'-(2,6-difluoro-3,5-dimethoxyphenyl)-1'H-spiro[cyclopropane-1,4'-[2,7]naphthyridin]-3'(2'H)-one diacetate (4560 g, 10.47 mol) in DCM (45.6 L) was charged aqueous sodium hydroxide (NaOH, 1823 g in water 22.8 L) solution while maintaining the reaction temperature at or below 30° C. After the reaction mixture was agitated for no less than 30 minutes, phases were separated. If necessary, the mixture may be filtered through Celite to facilitate phase separation. The aqueous phase was extracted with additional DCM (36.5 L). The organic phases were combined, dried over magnesium sulfate (MgSO$_4$, 4560 g) and concentrated under reduced pressure to afford the free base (1532.6 g). Alternatively, the diacetate was free based using aqueous ammonium hydroxide solution. To a turbid mixture of crude 6'-(aminomethyl)-2'-(2,6-difluoro-3,5-dimethoxyphenyl)-1',2'-dihydro-3'H-spiro[cyclopropane-1,4'-[2,7]naphthyridin]-3'-one (9.70 g, 25.8 mmol) in methylene chloride (150.0 ml) was added water (50 ml, 2775 mmol). Solids precipitated. Concentrated ammonia in H$_2$O (28%) (16.0 mL, 237 mmol) was added. Solids dissolved to give a two phase mixture. Organic phase was separated and washed with a premixed solution of ammonia in H$_2$O (28%) (16.0 mL, 846 mmol) and water (50.0 mL). Aqueous phases were combined and back extracted with dichloromethane (50.0 ml). All organic phases were combined, washed with water (75.0 ml×2) and concentrated to dryness to afford the free base, which after salt formation step afforded 10.5 g of hydrochloride salt.

To the 6'-(aminomethyl)-2'-(2,6-difluoro-3,5-dimethoxyphenyl)-1'H-spiro[cyclopropane-1,4'-[2,7]naphthyridin]-3'(2'H)-one free base (3352 g, 8.93 mol) was added DCM (70.4 L). The resulting solution was cooled to approximately 15-30° C. A solution of HCl in 1,4-dioxane (4 N, 2.46 L, 9.82 mol) was added to the solution while maintaining the reaction temperature at or below 30° C. After stirred for no less than 1 hour, the solid was filtered, washed with DCM (25.1 L) and dried to afford the desired HCl salt of the compound 6'-(aminomethyl)-2'-(2,6-difluoro-3,5-dimethoxyphenyl)-1'H-spiro[cyclopropane-1,4'-[2,7]naphthyridin]-3'(2'H)-one (3552 g, 96.6% yield, 97.55 A % purity).

Steps 7,8 and 9: N-((2'-(2,6-difluoro-3,5-dimethoxyphenyl)-3'-oxo-2',3'-dihydro-1'H-spiro[cyclopropane-1,4'-[2,7]naphthyridine]-6'-yl)methyl)acrylamide (Compound 1)

To a cooled mixture of 6'-(aminomethyl)-2'-(2,6-difluoro-3,5-dimethoxyphenyl)-1'H-spiro[cyclopropane-1,4'-[2,7]naphthyridin]-3'(2'H)-one HCl salt (1000 g, 2.43 mol) in DCM (15.0 L) was added aqueous sodium hydroxide (NaOH, 291 g, 7.28 mol, in 3.4 L of water) solution while maintaining the reaction temperature at or below 30° C. The resulting mixture was agitated for no less than 1 hour and cooled to −10-10° C. Acryloyl chloride (216 mL, 2.67 mol) was added. The mixture was agitated at approximately 0-10° C. until reaction completion was indicated by HPLC. The reaction mixture was warmed to rt and phases were separated. The aqueous phase was extracted with additional DCM (7.5 L). The organic phases were combined, washed with water and loaded onto a silica gel (15 kg) column with sea sand (5 kg) on top of the column. The column was eluted with a mixture of acetone and DCM. The desired fractions were combined and concentrated under reduced pressure to afford crude amide (782.7 g, 75% yield).

To a mixture of crude acrylamide (2675 g, 6.23 mol), acetonitrile (53.5 L), and water (18.7 L) at 30-40° C. was added aqueous NaOH (234.2 g, 5.86 mol, in 5.65 L of water) solution. The mixture was stirred at 30-40° C. until adequate removal of chloro impurity was demonstrated by HPLC. The reaction mixture was cooled and aqueous phosphoric acid (H$_3$PO$_4$, 85%, 321.5 g, 2.79 mol, diluted in 1.67 L of water) solution was slowly charged to adjust pH of the reaction mixture to between 8-10. The batch was agitated for 1 hour and concentrated under reduced pressure. Water (13.4 L) was charged to the reaction residue and the mixture was agitated. The solids were recovered and washed with water (2.7 L). The wet cake was returned to the reactor and reslurried in water (13.4 L) with agitation for no less than 30 minutes. The solid was recovered and the reslurry operation in water (13.4 L) was repeated one additional time. The solids were recovered and dried under vacuum to afford purified acrylamide (2962.9 g).

The solid (2950 g, 6.87 mol) was reslurried in acetone (17.7 L) at 40-60° C. for no less than 1 hour. After cooled to 0-10° C., the solids were recovered by filtration followed with washing with cooled acetone (3.0 L).

The recovered solids were dissolved in acetone (59.0 L)/USP grade purified water (17.7 L) at 40-60° C. and stirred with activated charcoal (590 g) for 0.5-2 hours. While hot, it was filtered through a bed of Celite (590 g). The Celite bed was rinsed with a hot mixture of acetone (6.64 L) and water (2.21 L). The filtrate and washes were combined and polish filtered into a clean reactor. The mixture was concentrated under reduced pressure and cooled to the room temperature. The solids were filtered, washed with filtered USP grade purified water (14.8 L) and dried under vacuum at 40-50° C. to afford the final compound N-((2'-(2,6-difluoro-3,5-dimethoxyphenyl)-3'-oxo-2',3'-dihydro-1'H-spiro[cyclopropane-1,4'-[2,7]naphthyridine]-6'-yl)methyl)acrylamide (2301 g, 78% yield). The compound isolated was determined to be Form I.

LC-MS calculated for $C_{22}H_{22}F_2N_3O_4[M+H]^+$ m/z: 430.15; found 430.1; $^1$H NMR (500 MHz, DMSO-d$_6$) δ 8.58 (t, J=5.7 Hz, 1H), 8.36 (s, 1H), 7.06 (t, J=8.2 Hz, 1H), 6.89 (s, 1H), 6.32 (dd, J=17.1, 10.2 Hz, 1H), 6.11 (dd, J=17.1, 2.1 Hz, 1H), 5.61 (dd, J=10.2, 2.1 Hz, 1H), 4.94 (s, 2H), 4.41 (d, J=5.8 Hz, 2H), 3.89 (s, 6H), 1.74 (dd, J=3.9, 3.9 Hz, 2H), 1.43 (dd, J=4.0, 4.0 Hz, 2H); $^{13}$C NMR (150 MHz, DMSO-d$_6$) δ 168.7, 164.6, 157.6, 145.6, 145.1, 143.5, 141.3, 131.6, 125.4, 125.0, 119.7, 114.4, 100.0, 56.9, 49.2, 44.1, 23.6, 20.4; $^{19}$F NMR (376 MHz, DMSO-d$_6$) δ −150.9.

Alternative Synthesis of 6'-(aminomethyl)-2'-(2,6-difluoro-3,5-dimethoxyphenyl)-1'H-spiro[cyclopropane-1,4'-[2,7]naphthyridin]-3'(2'H)-one (12)

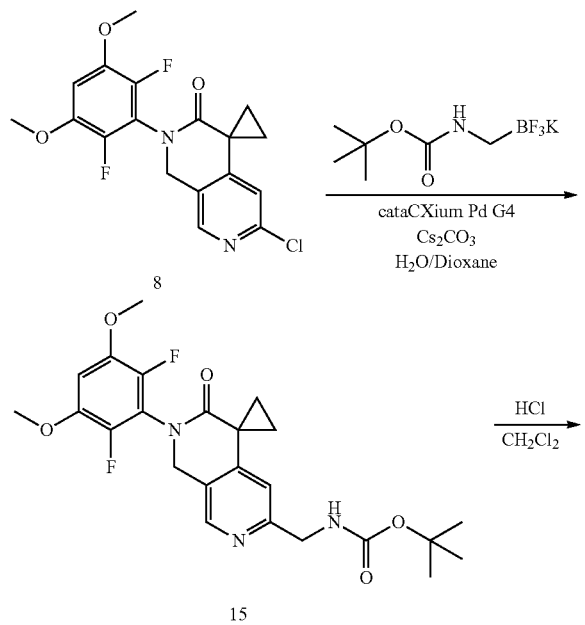

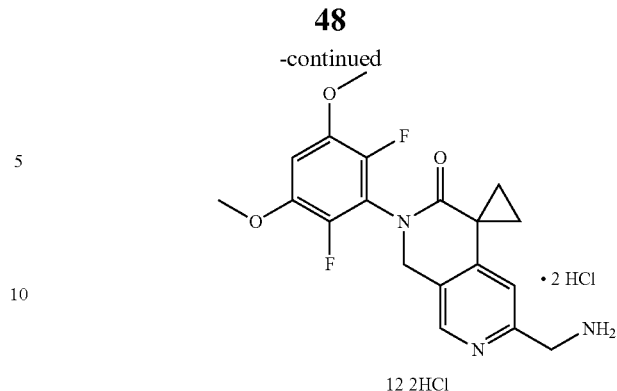

tert-butyl (2'-(2,6-difluoro-3,5-dimethoxyphenyl)-3'-oxo-2',3'-dihydro-1'H-spiro[cyclopropane-1,4'-[2,7]naphthyridine]-6'-yl)methylcarbamate (15)

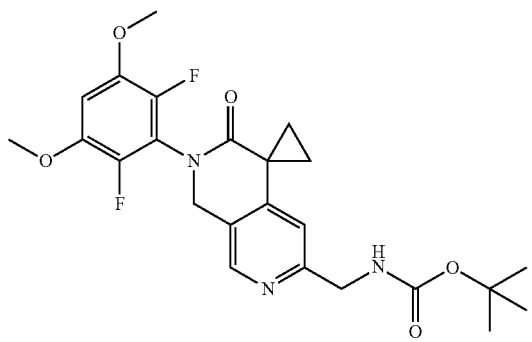 [SMILES: COc1cc(OC)c(F)c(N2Cc3cnc(CNC(=O)OC(C)(C)C)cc3C3(CC3)C2=O)c1F]

A degassed mixture of 6'-chloro-2'-(2,6-difluoro-3,5-dimethoxyphenyl)-1',2'-dihydro-3'H-spiro[cyclopropane-1,4'-[2,7]naphthyridin]-3'-one (2000.0 mg, 5.25 mmol), potassium N-Boc-aminomethyltrifluoroborate (3213 mg, 13.55 mmol), cesium carbonate (7838 mg, 24.06 mmol), cataCXium Pd G4 (116 mg, 0.157 mmol), water (20.0 ml, 1110 mmol) and dioxane (20.0 ml) was heated at 85° C. for 3 hours. The reaction was allowed to cool to room temperature. The organic phase was separated and heptane (10 mL) was added, followed by MTBE (10 mL). The mixture was stirred for 30 min. The solids were filtered, dried under vacuum at 50° C. overnight to give 1.78 g of the desired product as a brown solid. $^1$H NMR (400 MHz, CDCl$_3$) δ 8.26 (s, 1H), 6.68-6.59 (m, 2H), 5.43 (s, 1H), 4.90 (s, 2H), 4.37 (d, J=5.5 Hz, 2H), 3.87 (s, 6H), 2.00 (m, J=3.6 Hz, 2H), 1.64 (s, 1H), 1.44 (s, 9H), 1.36 (q, J=4.2 Hz, 2H).

6'-(aminomethyl)-2'-(2,6-difluoro-3,5-dimethoxy-phenyl)-1'H-spiro[cyclopropane-1,4'-[2,7]naphthyridin]-3'(2'H)-one dihydrochloride (12 2HCl)

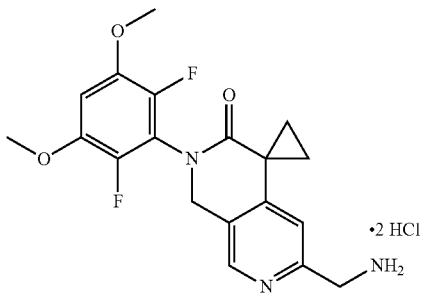 [SMILES: COc1cc(OC)c(F)c(N2Cc3cnc(CN)cc3C3(CC3)C2=O)c1F ; "·2 HCl"]

Into a 500 mL round bottom with stir bar was charged tert-butyl {[2'-(2,6-difluoro-3,5-dimethoxyphenyl)-3'-oxo-2',3'-dihydro-1'H-spiro[cyclopropane-1,4'-[2,7]naphthyridin]-yl]methyl}carbamate (14.7 g, 30.9 mmol) and methylene chloride (250.0 mL) at room temperature to give a thin slurry. 4.0 M Hydrogen chloride in dioxane (59.1 mL, 236 mmol) was added at room temperature. The mixture was stirred for four hours. The solids were filtered, washed with a generous volume of DCM and dried on the filter then overnight under vacuum to give 14.14 g of the desired bis-HCl salt (102% yield). $^1$H NMR (400 MHz, DMSO-$d_6$) δ 8.73 (s, 3H), 8.52 (s, 1H), 7.45 (s, 1H), 7.08 (t, J=8.2 Hz, 1H), 6.81 (s, 1H), 5.01 (s, 2H), 4.32-4.08 (m, 2H), 3.89 (s, 6H), 1.82 (q, J=3.9 Hz, 2H), 1.59 (q, J=4.0 Hz, 2H).

Alternative Synthesis of 6'-(aminomethyl)-2'-(2,6-difluoro-3,5-dimethoxyphenyl)-1'H-spiro[cyclopropane-1,4'-[2,7]naphthyridin]-3'(2'H)-one (12)

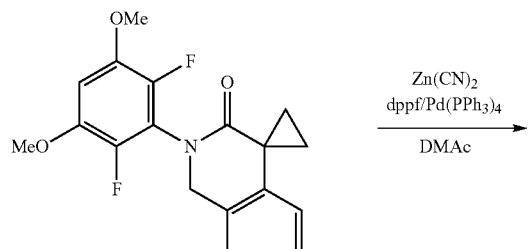

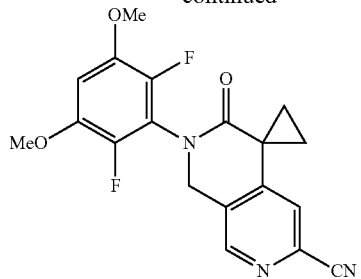

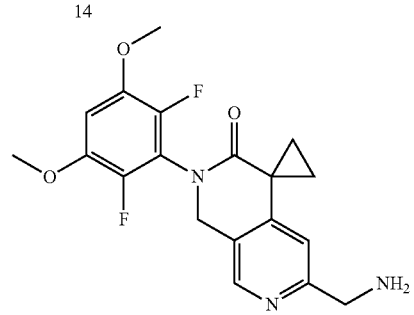

2'-(2,6-difluoro-3,5-dimethoxyphenyl)-3'-oxo-2',3'-dihydro-1'H-spiro[cyclopropane-1,4'-[2,7]naphthyridine]-6'-carbonitrile (14)

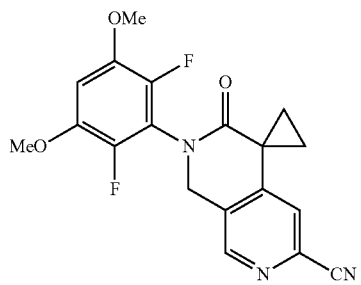 [SMILES: COc1cc(OC)c(F)c(N2Cc3cnc(C#N)cc3C3(CC3)C2=O)c1F]

A degassed mixture of 6'-chloro-2'-(2,6-difluoro-3,5-dimethoxyphenyl)-1',2'-dihydro-3'H-spiro[cyclopropane-1,4'-[2,7]naphthyridin]-3'-one (2.25 g, 5.91 mmol), zinc cyanide (1.39 g, 11.8 mmol), dppf (0.15 g, 0.26 mmol), Pd(PPh$_3$)$_4$ (0.1 g, 0.089 mmol) and N,N-dimethylacetamide (25 mL, 270 mmol) was stirred at 100° C. for 1 hour. The reaction was cooled to room temperature and filtered through a pad of Celite. The Celite bed was washed with 25 mL of DMAC. The filtrate and washes were combined and cooled to 5° C. and 100 mL of water was added. The resulting yellow slurry was stirred for 1.5 hours and filtered. The solids were washed with water (3×30 mL) and heptane (3×20 mL) and dried to give 2.3 g of the desired crude product. LC-MS calculated for $C_{19}H_{16}F_2N_3O_3$[M+H]$^+$ m/z: 372.11; found 372.1. $^1$H NMR (400 MHz, DMSO-$d_6$) δ 8.55 (s, 1H), 7.70 (s, 1H), 7.08 (t, J=8.2 Hz, 1H), 5.06 (s, 2H), 3.89 (s, 6H), 1.79 (q, J=4.0, 3.6 Hz, 2H), 1.64 (q, J=4.1 Hz, 2H).

51

6'-(aminomethyl)-2'-(2,6-difluoro-3,5-dimethoxy-phenyl)-1'H-spiro[cyclopropane-1,4'-[2,7]naphthyridin]-3'(2'H)-one (12)

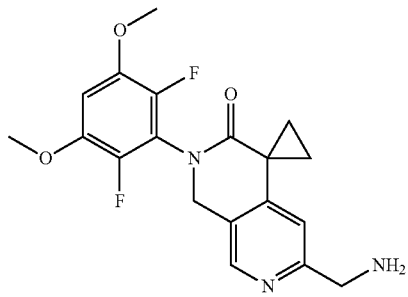 [SMILES: COc1cc(OC)c(F)c(N2Cc3cnc(CN)cc3C3(CC3)C2=O)c1F]

2'-(2,6-difluoro-3,5-dimethoxyphenyl)-3'-oxo-2',3'-dihydro-1'H-spiro[cyclopropane-1,4'-[2,7]naphthyridine]-6'-carbonitrile (37.1 mg, 0.100 mmol) in EtOH (2.0 ml) was stirred under $N_2$ at room temperature. Potassium borohydride (32.3 mg, 0.600 mmol) and Raney Nickel (11.7 mg, 0.200 mmol) were added. The reaction was stirred at room temperature for 15 minute and then 60° C. for 4 hours. The mixture was cooled to room temperature and filtered through a pad of Celite. The Celite was washed with DCM. The filtrate and washes were combined and concentrated to give crude product. LC-MS calculated for $C_{19}H_{20}F_2N_3O_3$ $[M+H]^+$ m/z: 376.1; found: 376.1.

Alternative purification of 6'-(aminomethyl)-2'-(2,6-difluoro-3,5-dimethoxyphenyl)-1'H-spiro[cyclopropane-1,4'-[2,7]naphthyridin]-3'(2'H)-one (12)

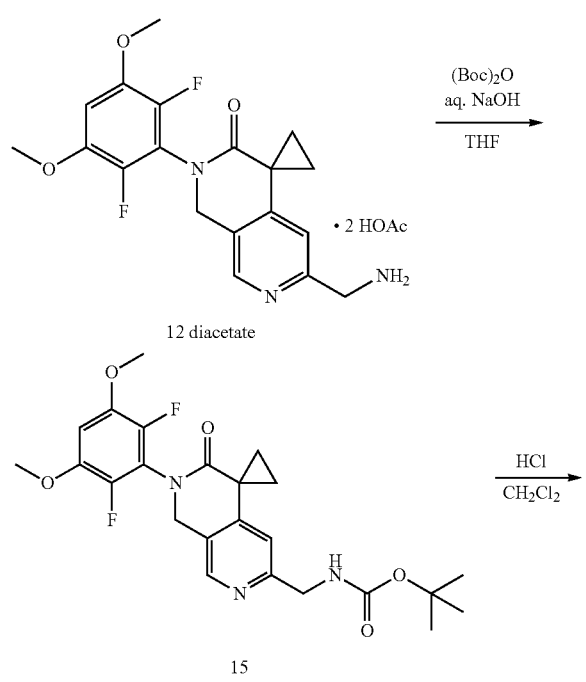

52

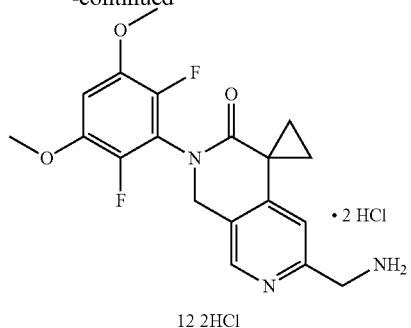

tert-butyl (2'-(2,6-difluoro-3,5-dimethoxyphenyl)-3'-oxo-2',3-dihydro-1'H-spiro[cyclopropane-1,4'-[2,7]naphthyridine]-6'-yl)methylcarbamate (15)

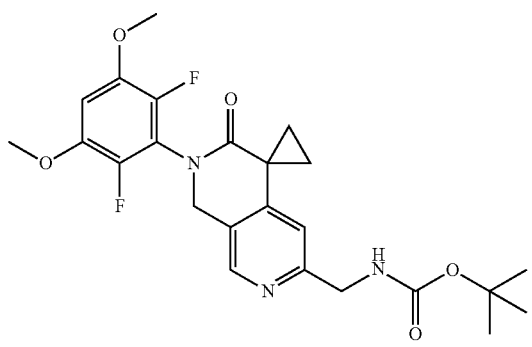 [SMILES: COc1cc(OC)c(F)c(N2Cc3cnc(CNC(=O)OC(C)(C)C)cc3C3(CC3)C2=O)c1F]

Into a 1 L round bottom with stir bar was charged [A] 6'-(aminomethyl)-2'-(2,6-difluoro-3,5-dimethoxyphenyl)-1',2'-dihydro-3'H-spiro[cyclopropane-1,4'-[2,7]naphthyridin]-3'-one acetate (17.5 g, 40.2 mmol) and Tetrahydrofuran (350.0 mL) to give a slurry. 2.0 M Sodium hydroxide in water (60.3 mL, 1.20E2 mmol) was added and the resulting mixture was stirred for 5 minutes to give a homogeneous solution. Di-tert-Butyldicarbonate (17.5 g, 80.4 mmol) was added at room temperature in one portion. The reaction was complete after 2 hours as indicated by HPLC. The reaction was diluted with water (350.0 mL) and ethyl acetate (350.0 mL). After phase separation, the aqueous fraction was extracted with ethyl acetate (100.0 mL). The organic extracts were combined, dried over $MgSO_4$, filtered and concentrated to a thick slurry. MTBE was added and the mixture was concentrated again to a fairly thick slurry. Heptane was added. The mixture was stirred at room temperature for 1 hour. The solids were filtered, rinsed with fresh heptane and dried under vacuum to give 15.3 g of off-white solids (80.1% yield). $^1$H NMR (400 MHz, $CDCl_3$) δ 8.26 (s, 1H), 6.68-6.59 (m, 2H), 5.43 (s, 1H), 4.90 (s, 2H), 4.37 (d, J=5.5 Hz, 2H), 3.87 (s, 6H), 2.00 (m, J=3.6 Hz, 2H), 1.64 (s, 1H), 1.44 (s, 9H), 1.36 (q, J=4.2 Hz, 2H).

Synthesis of 6'-chloro-2'-(2,6-difluoro-3,5-dimethoxyphenyl)-1',2'-dihydro-3'H-spiro[cyclopropane-1,4'-[2,7]naphthyridin]-3'-one (8)

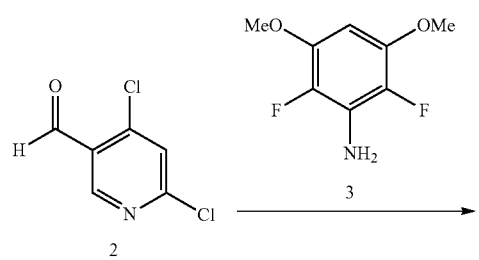

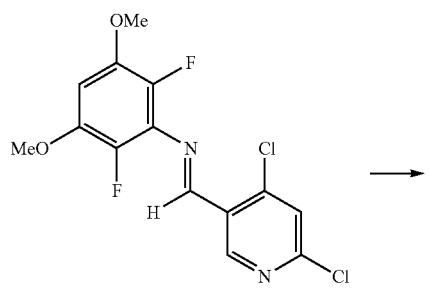

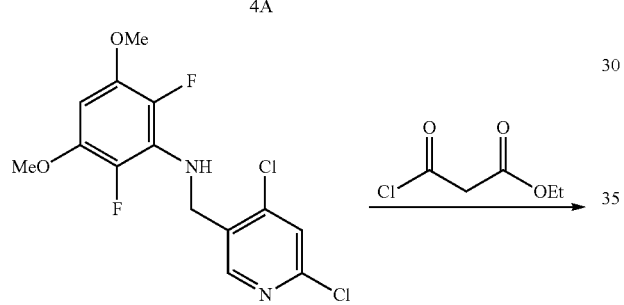

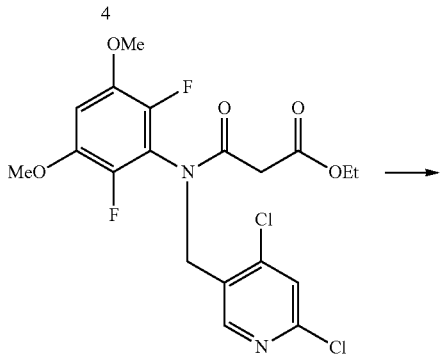

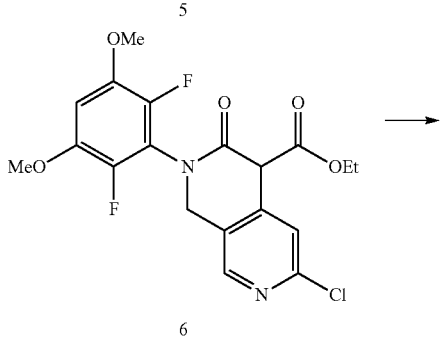

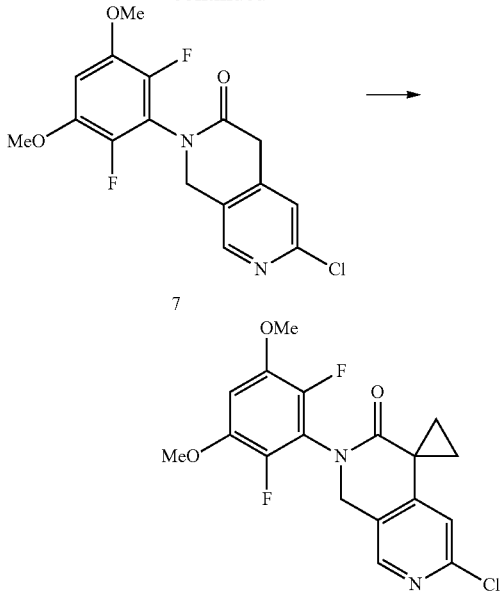

N-[(4,6-dichloropyridin-3-yl)methyl]-2,6-difluoro-3,5-dimethoxyaniline

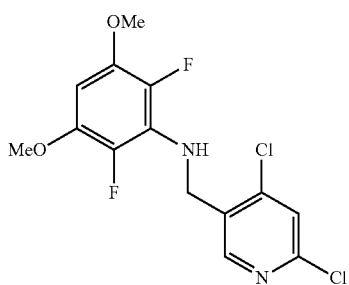 [SMILES: COc1cc(OC)c(F)c(NCc2cnc(Cl)cc2Cl)c1F]

Procedure 1:

To a stirred solution of 4,6-dichloronicotinaldehyde (105.7 g, 546.5 mmol) in anhydrous THF (200 mL) under $N_2$ was added 2,6-difluoro-3,5-dimethoxyaniline (109.6 g, 573.8 mmol) and dibutyltin dichloride (3.46 g, 10.9 mmol). After stirred 6 min at rt, phenylsilane (65.1 g, 601.2 mmol) was added in portions, and the mixture was stirred at rt for 48 h. The reaction mixture was diluted with hexanes (1400 mL), stirred for 2 h, and the resulting precipitate was filtered to afford the crude product (141 g). The product was purified by filtration via a pack of silica gel on a disposable funnel eluting with EtOAc to afford the desired product (138.6 g, 72.6%). LC-MS calculated for $C_{14}H_{13}Cl_2F_2N_2O_2$ m/z $[M+H]^+$; 349; found 349.

Procedure 2:

To a stirred solution of 2,6-difluoro-3,5-dimethoxyaniline (10.09 g, 53.3 mmol) and 4,6-dichloronicotinaldehyde (10.0 g, 52.3 mmol) and DMF (150 ml) in oven-dried 100 mL RBF under $N_2$ in a water bath was added TMSCl (16.70 ml, 131 mmol) dropwise at rt over 15 minutes to give a solution. The mixture was stirred at room temperature for 2.5 hours to give a thick slurry. Borane in THF (1.0 M, 52.3 ml, 52.3 mmol) was added. The mixture was stirred at room temperature for 3 hours and cooled to 0° C. Water (110 ml) was added and the mixture was stirred for 20 minutes. Ammonium hydroxide (14.2 ml, 89 mmol) in water (21.6 ml, 1197 mmol) was added dropwise to the reaction and the mixture was stirred for additional 20 minutes. Water (184 ml) was added and the stirring was continued. The solid was filtered, washed sequentially with water (3×15 mL) and heptane (2×15 mL) and dried under vacuum at 50° C. to give the crude product (17.1 g, 94% yield, 99.55 A % purity).

Procedure 3:

To a stirred solution of 2,6-difluoro-3,5-dimethoxyaniline (9.03 g, 47.7 mmol) and sodium triacetoxyborohydride (38.0 g, 180 mmol) in methylene chloride (60 mL)/trifluoroacetic acid (30 mL) was added 4,6-dichloronicotinaldehyde (8.00 g, 45.5 mmol) in small portions at room temperature. After 1 hour, the volatiles were removed under vacuo and saturated aqueous NaHCO$_3$ (200 mL) was added. The resulting mixture was extracted with DCM (3×150 mL). The organic layers were combined, dried over Na$_2$SO$_4$, and concentrated. The residue was purified on silica gel (eluting with 0 to 0-40% EtOAc in hexanes) to afford the desired product (15.0 g). LC-MS calculated for C$_{14}$H$_{13}$Cl$_2$F$_2$N$_2$O$_2$ [M+H]$^+$ m/z: 349.0; found 349.1.

Procedure 4:

(E)-1-(4,6-dichloropyridin-3-yl)-N-(2,6-difluoro-3,5-dimethoxyphenyl)methan-imine (4A)

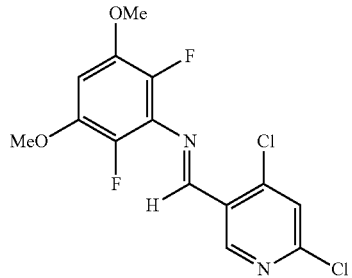 [SMILES: COc1cc(OC)c(F)c(/N=C/c2cnc(Cl)cc2Cl)c1F]

4,6-Dichloronicotinaldehyde (1293 g, 7.347 moles, 1.00 equiv) and acetic acid (1300 mL, 22.86 mol, 3.1 equiv) were sequentially added to a solution of 2,6-difluoro-3,5-dimethoxyaniline (1409 g, 7.449 mol, 1.014 equiv) in ethanol (9 L) at room temperature. After stirring for 18 hours, the solids were collected by filtration and rinsed with ethanol (4 L). The filtrates were concentrated under reduced pressure to a volume of 3 L. The solids were collected by filtration and rinsed with ethanol (2 L). The filtrates were concentrated under reduced pressure to a volume of 1.5 L. The solids were collected by filtration and rinsed with ethanol (1 L). The three batches of solids were dried separately under vacuum at 40° C. overnight to give the desired compound (1509 g, 360 g and 419 g respectively). The three batches were combined and dry blended to give the desired compound (2287 g, 89.7% yield, >97% purity). LCMS calculated for C$_{14}$H$_{11}$Cl$_2$F$_2$N$_2$O$_2$(M+H): 347.02; Found: 347.1. $^1$H NMR (300 MHz, CDCl$_3$) δ 9.23 (s, 1H), 8.95 (s, 1H), 7.45 (s, 1H), 6.50 (m, 1H), 3.90 (s, 6H).

N-((4,6-dichloropyridin-3-yl)methyl)-2,6-difluoro-3,5-dimethoxyaniline (4)

Solid sodium borohydride (88 g, 2.33 moles, 1.1 equiv) was added portionwise keeping temperature between 27-33° C. to a solution of compound (E)-1-(4,6-dichloropyridin-3-yl)-N-(2,6-difluoro-3,5-dimethoxyphenyl)methan-imine (732 g, 2.11 moles, 1.0 equiv) in dichloromethane (3.65 L) and methanol (1.8 L) at 8° C. The reaction mixture was stirred at room temperature overnight, at which point LCMS indicated the reaction was complete. The reaction was diluted with dichloromethane (1.5 L) and water (3.0 L) and stirred for one hour. The organic layer was separated and the aqueous layer was back-extracted with dichloromethane (2×1 L). The combined organic layers were concentrated under reduced pressure to give crude product (739.5 g, over theory), which was used subsequently. LCMS calculated for C$_{14}$H$_{13}$Cl$_2$F$_2$N$_2$O$_2$(M+H): 349.03; Found: 349.2. $^1$H NMR (300 MHz, CDCl$_3$) δ 8.32 (s, 1H), 7.35 (s, 1H), 6.10 (m, 1H), 4.62 (s, 2H), 4.25 (s, 1H), 3.85 (s, 6H).

ethyl 3-[[(4,6-dichloropyridin-3-yl)methyl](2,6-difluoro-3,5-dimethoxyphenyl)amino]-3-oxopropanoate (5)

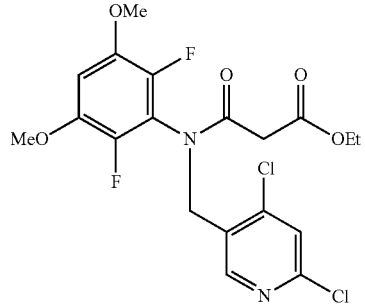 [SMILES: CCOC(=O)CC(=O)N(Cc1cnc(Cl)cc1Cl)c1c(F)c(OC)cc(OC)c1F]

Procedure 1:

To a stirred solution of N-[(4,6-dichloropyridin-3-yl)methyl]-2,6-difluoro-3,5-dimethoxyaniline (138.6 g, 397.0 mmol) in THF (500 mL) was added NaH (60% w/w in mineral oil, 10.0 g, 417 mmol) in portions at rt. After stirred at rt for 15 minutes, the solution was cooled to 0° C., and ethyl malonyl chloride (92.5 g, 614.4 mmol) was added dropwise under N$_2$. The ice-bath was removed after 10 min, and the reaction mixture was stirred at rt for 1.5 h. The reaction mixture was diluted with DCM and was quenched with saturated aqueous NH$_4$Cl, and extracted with DCM (3×1000 mL). The organic layers were combined, washed with 5% NaHCO$_3$ solution, dried over Na$_2$SO$_4$, and concentrated. The crude was added 25% MTBE in hexane, and colorless solid formed. Filtration gave the product as a colorless crystalline solid (177.5 g, 96.5%). LC-MS calculated for C$_{19}$H$_{19}$Cl$_2$F$_2$N$_2$O$_5$ m/z [M+H]$^+$: 463; found 463.

Procedure 2:

To a stirred solution of N-[(4,6-dichloropyridin-3-yl)methyl]-2,6-difluoro-3,5-dimethoxyaniline (138.6 g, 397.0 mmol) and triethylamine (44 g, 430 mmol) in DCM (500 mL) was added ethyl malonyl chloride (65 g, 430 mmol) in dropwise at rt. After stirred at rt for 10 minutes, LC-MS showed the completion of the reaction. The reaction mixture was partitioned between DCM and 1.0 N HCl solution. The organic layer was washed with saturated NaHCO$_3$ solution, brine, dried and concentrated to give the crude oil product. Treatment with 25% MTBE in hexane gave the product (131 g, 98.7% yield) for the next step.

Procedure 3:

Ethyl malonyl chloride (477 g, 3.17 moles, 1.5 equiv) was added dropwise at room temperature to a mixture of crude N-[(4,6-dichloropyridin-3-yl)methyl]-2,6-difluoro-3,5-dimethoxyaniline (739.5 g, 2.11 moles, 1 equiv) and sodium bicarbonate (550 g, 6.55 moles, 3.1 equiv) in dichloromethane (3 L). After stirring for 1 hour, water (3 L) was added and the layers were separated. The aqueous layer was back extracted with dichloromethane (1 L). The combined organic layers were concentrated under reduced pressure. The crude product was purified by over silica gel (6.5 kg), eluting with a gradient of 20 to 50% ethyl acetate in heptanes to give the desired product (754.5 g, 77% yield, >95% purity). LCMS calculated for $C_{19}H_{19}Cl_2F_2N_2O_5[M+H]^+$: 463.06; Found: 462.9. $^1$H NMR (300 MHz, CDCl$_3$) δ 8.35 (s, 1H), 7.30 (s, 1H), 6.67 (m, 1H), 5.02 (s, 2H), 4.10 (m, 2H), 3.82 (s, 6H), 3.23, (s, 2H), 1.21 (m, 3H).

6-chloro-2-(2,6-difluoro-3,5-dimethoxyphenyl)-3-oxo-1,2,3,4-tetrahydro-2,7-naphthyridine-4-carboxylate (6)

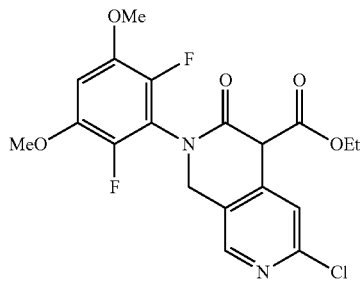 [SMILES: CCOC(=O)C1C(=O)N(c2c(F)c(OC)cc(OC)c2F)Cc2cnc(Cl)cc21]

Procedure 1:

A mixture of ethyl 3-[[(4,6-dichloropyridin-3-yl)methyl](2,6-difluoro-3,5-dimethoxyphenyl)amino]-3-oxopropanoate (36.0 g, 77.7 mmol), Cu(I)I (2.80 g, 14.7 mmol), Cs$_2$CO$_3$ (70.0 g, 215 mmol), and 2-pyridinecarboxylic acid (7.23 g, 58.7 mmol) in DMSO (204 mL) was stirred and degassed with N$_2$ three times, then heated to 120° C. for 2 h, HPLC indicated no starting material left. The heat was removed, the reaction was cooled to rt, and then slowly filtered the reaction mixture into 500 mL of aqueous 2N HCl in ice-bath with stirring, and rinsed with more 2N HCl solution. The resulting solid in aqueous HCl solution was filtered, washed with water (3×300 mL), dried in air to afford the crude product. The crude was stirred and slurried in 60% EtOAc in hexane (400 mL). Filtration, washed with more 60% EtOAc in hexane gave the product as an off-white solid (28.6 g, 86.2% yield). LC-MS calculated for $C_{19}H_{18}ClF_2N_2O_5$ m/z [M+H]$^+$: 427; found 427.

Procedure 2:

Into a 2 L, 4-neck round bottom flask equipped with stir bar, thermocouple, condenser and 3-way valve were charged ethyl 3-[[(4,6-dichloropyridin-3-yl)methyl](2,6-difluoro-3,5-dimethoxyphenyl)amino]-3-oxopropanoate (107.9 g, 232.9 mmol), dimethyl sulfoxide (647 mL) and K$_3$PO$_4$ (173 g, 813 mmol) to give a slurry. After degassed 4× backfilling with nitrogen each time, the reaction mixture was stir at 80° C. overnight and 90° C. for 1 hour, at which time the reaction was complete as indicated by HPLC. The reaction was allowed to cool to room temperature and slowly added in portions over 52 minutes to a cooled 1.0 M Hydrogen chloride in water (1295 mL, 1295 mmol) in a 5 L, 4-neck round bottom flask with overhead stirring, while maintaining the temperature <15° C. Following the addition, the slurry was stirred for 90 minutes in the ice bath. The solid was filtered, washed with water (1000 mL) and dried on the filter under vacuum overnight to afford 141.2 g of tan solids. The solids were redissolved in methylene chloride (720 mL) and ethyl acetate (500 mL). The resulting solution was washed with water (1000 mL×2) and concentrate on a rotovap under mild vacuum (~200 mbar) to 314 g. Heptane (3500 mL) was added dropwise over 35 minutes. The slurry was stirred overnight at room temperature. The solids were filtered, washed with a solution of ethyl acetate (135 mL) and heptane (180 mL) and dried on the funnel under vacuum to afford 88 g (88.5% yield) of yellow solids.

6-chloro-2-(2,6-difluoro-3,5-dimethoxyphenyl)-1,2-dihydro-2,7-naphthyridin-3(4H)-one (7)

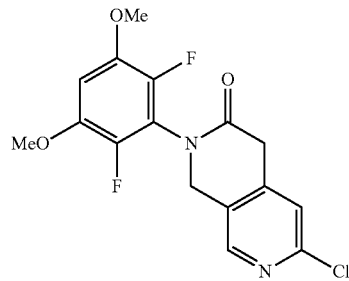 [SMILES: COc1cc(OC)c(F)c(N2Cc3cnc(Cl)cc3CC2=O)c1F]

Into 5 L, 4-neck round bottom flask with overhead stirring, thermocouple, heating mantle, condenser and nitrogen inlet were charged ethyl 6-chloro-2-(2,6-difluoro-3,5-dimethoxyphenyl)-3-oxo-1,2,3,4-tetrahydro-2,7-naphthyridine-4-carboxylate (227.1 g, 532.1 mmol) and 1,4-dioxane (900 mL) followed by 12.0 M hydrogen chloride in water (448 mL, 5380 mmol) and water (1695 mL). The reaction mixture was stirred at 80° C. for 6 hours and then allowed to cool to room temperature and stirred overnight. The reaction was complete after stirring overnight as indicated by HPLC. The mixture was cooled in an ice bath to 7.5° C. and the pH was adjusted to 8 with a solution of 6.0 M Sodium hydroxide in water (941 mL, 5646 mmol) added dropwise over 75 minutes via an addition funnel, while maintaining the internal temperature <15° C. After the pH adjustment, the cold bath was removed and water (1695 mL) was added dropwise via addition funnel over 17 minutes. The mixture was stirred at room temperature for 3.5 hours. The solids were filtered, washed with water (1695 mL), dried on the filter and then at 50° C. in vacuum oven overnight to afford 180.5 g (85.1% yield) of tan/light yellow solid. Purity was 99.2%.

6'-chloro-2'-(2,6-difluoro-3,5-dimethoxyphenyl)-1', 2'-dihydro-3'H-spiro[cyclopropane-1,4'-[2,7]naphthyridin]-3'-one (8)

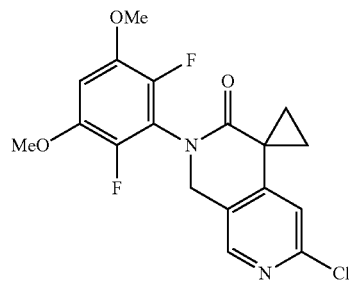 [SMILES: COc1cc(OC)c(F)c(N2Cc3cnc(Cl)cc3C3(CC3)C2=O)c1F]

Into a 5 L, 3-neck round bottom flask equipped with stir bar, thermocouple, addition funnel and nitrogen inlet were charged 6-chloro-2-(2,6-difluoro-3,5-dimethoxyphenyl)-1,4-dihydro-2,7-naphthyridin-3 (2H)-one (189.8 g, 519.0 mmol), N,N-dimethylformamide (570 mL) and cesium carbonate (377.3 g, 1157 mmol) under nitrogen. The mixture was cooled in an ice bath to 12° C. 1-Bromo-2-chloroethane (130.6 g, 892.1 mmol) was charged via the addition funnel dropwise over 12 minutes. Internal temperature rose to 19.5° C. at the end of the addition. After the addition, the cold bath was removed and the reaction was stirred at room temperature for 3 hours and 30° C. for 1 hour. Additional 1-bromo-2-chloroethane (5.0 mL, 60.0 mmol) was added and the reaction was stirred for additional 5 hours at 30° C. and overnight at room temperature. Additional cesium carbonate (12.0 g, 36.8 mmol) was charged and the reaction was stirred at 35° C. for 2 hours followed 40° C. for 4 hours. The reaction was found to be complete by HPLC.

To the reaction mixture was added heptane (750 mL) followed by water (2300 mL). The mixture was stirred for 1 hour. The solids were filtered, washed water (2300 mL), dried on the filter under vacuum to afford 207 g (105%) of the desired product, which was used in the next reaction without further purification.

Preparation of 4,6-Dichloronicotinaldehyde (2)

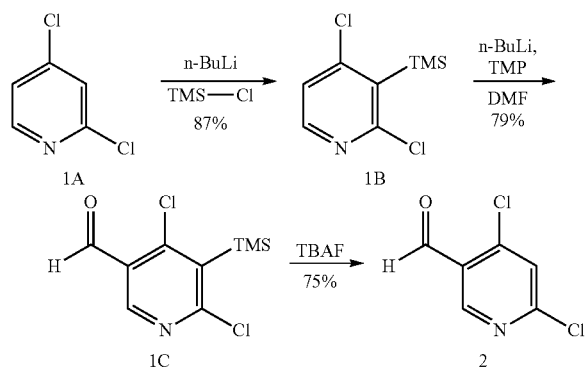

2,4-Dichloro-3-(trimethylsilyl)pyridine (1B)

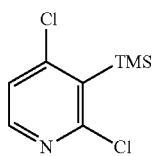 [SMILES: C[Si](C)(C)c1c(Cl)ccnc1Cl]

A solution of 2,4-dichloropyridine (650 g, 4.39 mol, 1 equiv) in THF (2 L) was added dropwise over one hour, while maintaining the internal temperature below −65° C., to a solution of 2.5 M n-butyllithium in hexanes (1.95 L, 4.875 mol, 1.1 equiv) in THF (5.2 L) at −78° C. After stirring at −78° C. for 30 minutes, trimethylchlorosilane (580 g, 680 mL, 5.34 mol, 1.2 equiv) was added over one minute. The internal temperature increased to −50° C. The reaction mixture was stirred cold for 10 minutes and quenched with 20% aqueous ammonium chloride (4.3 L) and saturated brine (1.45 L). The product was extracted with MTBE (2×6 L). The combined organic layers were washed with brine (2×0.9 L) and concentrated under reduced pressure. The residue was purified over silica gel (4 kg), eluting with a gradient of 0 to 20% ethyl acetate in heptanes, to give the desired compound (841 g, yield 87%, purity 97%) as a dark oil. LCMS calculated for $C_8H_{12}Cl_2NSi$ $[M+H]^+$: 220.01; Found: 219.9. $^1$H NMR (300 MHz, CDCl$_3$) δ 8.20 (d, 5.27 Hz, 1H), 7.20 (d, 5.27 Hz, 1H), 0.52 (s, 9H).

4,6-Dichloro-5-(trimethylsilyl)nicotinaldehyde (IC)

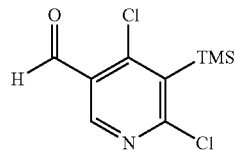

2.5 M n-Butyllithium in hexane (1540 mL, 3.85 mol, 1.4 equiv) was added over 10 minutes, while maintaining temperature below −10° C., to a solution of 2,2,6,6-tetramethylpiperidine (568 g, 4.02 mol, 1.46 equiv) in THF (5 L) at −40° C. The reaction mixture was allowed to warm-up to 0° C. and was stirred at this temperature for 30 minutes. The mixture was cooled to −78° C. and a solution of 2,4-dichloro-3-(trimethylsilyl)pyridine (604 g, 2.74 mol, 1 equiv) in THF (2.9 L) was added over 30 minutes maintaining the internal temperature below −70° C. The reaction was stirred at −78° C. for an additional 90 minutes. 4-Formylmorpholine (552 g, 4.8 mol. 1.75 equiv) was added over 30 minutes, while maintaining the internal temperature below −70° C., and the reaction was stirred at −78° C. for 30 minutes. The reaction was quenched with 1N HCl and the product was extracted with MTBE (2×8 L). The combined organic layers were washed with saturated brine (2×4 L) and the solvent was removed under reduced pressure. The crude product was purified by over silica gel (3 kg), eluting with a gradient of 0 to 20% ethyl acetate in heptanes, to give the desired compound (538 g, 79% yield, 95% purity) as light yellow oil which partially solidified upon standing. LCMS calculated for $C_9H_{12}Cl_2NOSi$ $[M+H]^+$: 248.01; Found: 248.1. $^1$H NMR (300 MHz, CDCl$_3$) δ 10.49 (s, 1H), 8.74 (s, 1H), 0.57 (s, 9H).

4,6-Dichloronicotinaldehyde (2)

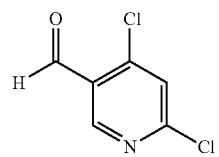

A solution of 4,6-dichloro-5-(trimethylsilyl)-nicotinaldehyde (1112 g, 4.48 mol, 1 equiv) in THF (8.8 L) and water (4.4 L) was cooled in ice/water bath to 5° C. Tetrabutylammonium fluoride trihydrate (1556 g, 4.92 mol, 1.1 equiv) was added portion-wise over 5 minutes. THF (2 L) was used to rinse reagents into the flask. A mild exothermic effect was observed (temperature increased to 15° C.). The cooling bath was removed and the reaction mixture was stirred at room temperature overnight, at which point LCMS indicated the reaction was complete. Water (11 L) was added and the product was extracted with ethyl acetate (3×12 L). The combined organic layers were washed with 10% sodium bicarbonate (10 L) and saturated brine (10 L). The solvent was evaporated under reduced pressure and the residue was purified over silica gel (3 kg), eluting with a gradient of 0 to 6% ethyl acetate in heptanes. The product was dried under vacuum at 30° C. for one hour to give the desired compound (596 g, 75% yield, 99% purity) as white solid. LCMS calculated for $C_6H_6Cl_2NO_2$ $[M+H_2O+H]^+$: 193.98; Found: 194.1. $^1H$ NMR (300 MHz, $CDCl_3$) δ 10.44 (s, 1H), 8.85 (s, 1H), 7.49 (s, 1H).

Alternative Synthesis of
4,6-Dichloronicotinaldehyde (2)

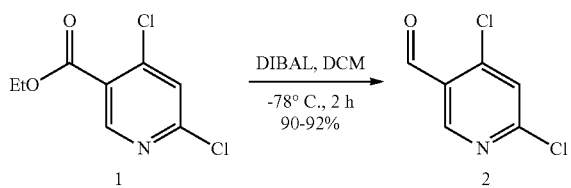 [SMILES: CCOC(=O)c1cnc(Cl)cc1Cl ; O=Cc1cnc(Cl)cc1Cl]

4,6-Dichloronicotinaldehyde (2)

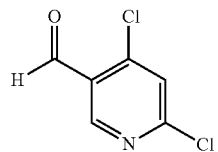

To a stirred solution of 2,4-dichloro-5-carbethoxypyridine (199.0 g, 904.3 mmol) in methylene chloride (2000.0 mL) at −78° C. under $N_2$ was added a solution of diisobutylaluminum hydride in methylene chloride (994.8 mL, 1.0 M, 994.8 mmol) dropwise over 85 min. After 2 h, LCMS indicated the reaction was complete. The reaction was quenched with aqueous 2 N HCl solution (600 mL), warmed up to room temperature, and stirred for 30 min. The organic layer was separated, and the aqueous layer was extracted with DCM (300 ml). The combined organic layers were washed with water (500 mL), dried over $Na_2SO_4$ and concentrated in vacuo to afford the crude aldehyde (161.5 g with 91.7% purity), which was used in the next step without further purification. LC-MS calculated for $C_6H_4Cl_2NO$ m/z $[M+H]^+$: 176; found 176.

Example 2

Preparation and Characterization of Form I

In one experiment, Form I was prepared according to the procedures in Example 1. Form I was characterized by XRPD. The XRPD was obtained from Rigaku MiniFlex X-ray Powder Diffractometer (XRPD). The general experimental procedures for XRPD were: (1) X-ray radiation from copper at 1.054056 Å with $K_β$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min. The XRPD pattern is shown in FIG. 1 and the XRPD data are provided in the table below.

TABLE 1

| 2-Theta | Height | H % |
|---|---|---|
| 8.1 | 974 | 92.5 |
| 9.0 | 235 | 22.3 |
| 11.5 | 54 | 5.1 |
| 12.3 | 602 | 57.2 |
| 15.2 | 94 | 8.9 |
| 16.0 | 226 | 21.5 |
| 17.2 | 48 | 4.6 |
| 18.0 | 202 | 19.2 |
| 18.8 | 66 | 6.3 |
| 19.5 | 118 | 11.2 |
| 20.0 | 130 | 12.3 |
| 20.4 | 85 | 8.1 |
| 21.1 | 142 | 13.5 |
| 21.6 | 49 | 4.7 |
| 22.6 | 83 | 7.9 |
| 23.3 | 1053 | 100 |
| 24.2 | 342 | 32.5 |
| 24.7 | 446 | 42.4 |
| 25.5 | 47 | 4.5 |
| 26.5 | 147 | 14 |
| 27.1 | 374 | 35.5 |
| 28.1 | 42 | 4 |
| 28.6 | 67 | 6.4 |
| 29.3 | 196 | 18.6 |
| 30.1 | 45 | 4.3 |
| 31.7 | 81 | 7.7 |
| 32.2 | 120 | 11.4 |
| 33.8 | 51 | 4.8 |
| 35.1 | 42 | 4 |
| 36.7 | 115 | 10.9 |
| 37.3 | 69 | 6.6 |
| 38.8 | 38 | 3.6 |
| 40.1 | 41 | 3.9 |
| 41.4 | 240 | 22.8 |
| 42.2 | 73 | 6.9 |
| 42.6 | 179 | 17 |
| 43.3 | 40 | 3.8 |
| 43.8 | 42 | 4 |

Form I was characterized by DSC. The DSC was obtained from TA Instruments Differential Scanning Calorimetry, Model Q200 with autosampler. The DSC instrument conditions were as follows: 30-300° C. at 10° C./min; Tzero aluminum sample pan and lid; and nitrogen gas flow at 50 mL/min. The DSC thermogram is shown in FIG. 2. The DSC thermogram revealed an endothermic event at an onset temperature of 206.9° C. with a peak temperature of 207.7° C.

Form I was characterized by TGA. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan. The TGA thermogram is shown in FIG. 3.

Example 3

Preparation and Characterization of Form II

In one experiment, Form II was prepared by adding about 30 mg of Form I to about 3 mL of saturated or cloudy solution of Form I prepared in chloroform followed by stirring at 22±1° C. for 3 days, which was filtered. Form II was also prepared in accordance with the procedures set forth in the examples provided herein, e.g., Examples 15 and 19.

Form II was characterized by XRPD. The XRPD was obtained using similar conditions as those for Form I. The XRPD pattern is shown in FIG. 4 and the XRPD data are provided in the table below.

TABLE 2

| 2-Theta | Height | H % |
| --- | --- | --- |
| 11.4 | 120 | 8.2 |
| 12.6 | 237 | 16.3 |
| 14.5 | 117 | 8.1 |
| 14.7 | 123 | 8.4 |
| 16.1 | 134 | 9.2 |
| 17.5 | 52 | 3.6 |
| 18.3 | 224 | 15.4 |
| 19.0 | 41 | 2.8 |
| 20.0 | 56 | 3.8 |
| 21.2 | 544 | 37.3 |
| 23.3 | 86 | 5.9 |
| 24.8 | 1457 | 100 |
| 26.2 | 110 | 7.5 |
| 26.7 | 146 | 10 |
| 27.9 | 167 | 11.5 |
| 28.3 | 256 | 17.6 |
| 29.7 | 157 | 10.8 |
| 31.3 | 53 | 3.7 |
| 32.1 | 130 | 8.9 |
| 32.4 | 198 | 13.6 |
| 33.6 | 39 | 2.7 |
| 34.9 | 106 | 7.3 |
| 36.6 | 71 | 4.9 |
| 39.3 | 56 | 3.8 |
| 40.0 | 54 | 3.7 |
| 41.0 | 51 | 3.5 |
| 44.3 | 137 | 9.4 |

Form II was characterized by DSC. The DSC was obtained using similar conditions as those for Form I. The DSC thermogram is shown in FIG. 5. The DSC thermogram revealed an endothermic event at an onset temperature of 206.5° C. with a peak temperature of 207.8° C.

Example 4

Preparation and Characterization of Form III

In one experiment, Form III was prepared as follows. To about 3 mL of saturated or cloudy solutions of Form I prepared in 1,4-dioxane was added about 30 mg of Form I followed by stirring at 22±1° C. for 3 days, which was filtered. Form III was also prepared in accordance with the procedures set forth in the examples provided herein, e.g., Examples 15, 19, and 20.

Form III was characterized by XRPD. The XRPD was obtained using similar conditions as those for Form I. The XRPD pattern is shown in FIG. 6 and the XRPD data are provided in the table below.

TABLE 3

| 2-Theta | Height | H % |
| --- | --- | --- |
| 4.2 | 335 | 23.1 |
| 7.6 | 1448 | 100 |
| 8.0 | 180 | 12.5 |
| 12.5 | 83 | 5.8 |
| 13.2 | 946 | 65.4 |
| 15.2 | 299 | 20.6 |
| 16.0 | 117 | 8.1 |
| 18.2 | 45 | 3.1 |
| 19.3 | 166 | 11.5 |
| 20.7 | 1158 | 80 |
| 21.2 | 168 | 11.6 |
| 22.3 | 77 | 5.4 |

TABLE 3-continued

| 2-Theta | Height | H % |
| --- | --- | --- |
| 22.8 | 135 | 9.3 |
| 25.6 | 305 | 21.1 |
| 26.7 | 166 | 11.5 |
| 27.2 | 100 | 6.9 |
| 27.4 | 80 | 5.5 |
| 28.4 | 51 | 3.5 |
| 29.3 | 45 | 3.1 |
| 30.7 | 44 | 3 |
| 33.9 | 37 | 2.6 |
| 42.4 | 30 | 2.1 |

Form III was characterized by DSC. The DSC was obtained using similar conditions as those for Form I. The DSC thermogram is shown in FIG. 7. The DSC thermogram revealed an endothermic event at an onset temperature of 205.5° C. with a peak temperature of 206.9° C.

Example 5

Preparation and Characterization of Form IV

In one experiment, Form IV was prepared as follows. To about 3 mL of saturated or cloudy solutions of Form I prepared in toluene was added about 30 mg of Form I followed by stirring at 25±1° C. for 3 days, which was filtered. Form IV was also prepared in accordance with the procedures set forth in the examples provided herein, e.g., Example 15.

Form IV was characterized by XRPD. The XRPD was obtained using similar conditions as those for Form I. The XRPD pattern is shown in FIG. 8 and the XRPD data are provided in the table below.

TABLE 4

| 2-Theta | Height | H % |
| --- | --- | --- |
| 4.3 | 251 | 33.4 |
| 11.9 | 689 | 91.9 |
| 12.9 | 353 | 47.1 |
| 14.3 | 270 | 36 |
| 15.1 | 198 | 26.5 |
| 15.5 | 109 | 14.5 |
| 16.6 | 61 | 8.1 |
| 16.8 | 39 | 5.3 |
| 18.0 | 322 | 42.9 |
| 19.6 | 57 | 7.7 |
| 19.7 | 69 | 9.2 |
| 18.0 | 55 | 7.3 |
| 21.1 | 113 | 15.1 |
| 21.4 | 91 | 12.2 |
| 22.1 | 48 | 6.5 |
| 22.9 | 555 | 74 |
| 23.3 | 750 | 100 |
| 24.5 | 149 | 19.9 |
| 25.1 | 160 | 21.4 |
| 26.8 | 337 | 44.9 |
| 28.6 | 68 | 9.1 |
| 29.6 | 100 | 13.3 |
| 32.6 | 77 | 10.3 |
| 33.6 | 47 | 6.3 |
| 33.8 | 42 | 5.6 |
| 36.7 | 48 | 6.4 |
| 41.0 | 38 | 5.1 |
| 41.4 | 34 | 4.5 |
| 42.2 | 42 | 5.6 |
| 43.6 | 72 | 9.5 |

Form IV was characterized by DSC. The DSC was obtained using similar conditions as those for Form I. The DSC thermogram is shown in FIG. 9. The DSC thermogram revealed an endothermic event at an onset temperature of 206.7° C. with a peak temperature of 208.2° C.

Example 6

Preparation and Characterization of Form V

In one experiment, Form V was prepared according to the procedures below. Approximately 3-4 mL of saturated solution of Form I in chloroform were evaporated under air without stirring at 22±1° C. Form V was also prepared in accordance with the procedures set forth in the examples provided herein, e.g., Examples 16 and 20.

Form V was characterized by XRPD. The XRPD was obtained using similar conditions as those for Form I. The XRPD pattern is shown in FIG. 10 and the XRPD data are provided in the table below.

TABLE 5

| 2-Theta | Height | H % |
|---|---|---|
| 6.6 | 121 | 4 |
| 8.2 | 94 | 3.1 |
| 9.2 | 128 | 4.2 |
| 11.5 | 1696 | 55.9 |
| 12.5 | 84 | 2.8 |
| 13.5 | 302 | 10 |
| 14.0 | 79 | 2.6 |
| 15.6 | 3031 | 100 |
| 17.9 | 307 | 10.1 |
| 19.0 | 207 | 6.8 |
| 19.4 | 336 | 11.1 |
| 20.7 | 1025 | 33.8 |
| 21.4 | 282 | 9.3 |
| 23.5 | 922 | 30.4 |
| 24.1 | 523 | 17.3 |
| 25.2 | 219 | 7.2 |
| 26.8 | 1010 | 33.3 |
| 27.5 | 149 | 4.9 |
| 28.5 | 194 | 6.4 |
| 30.8 | 146 | 4.8 |
| 32.0 | 172 | 5.7 |
| 33.9 | 143 | 4.7 |
| 34.5 | 66 | 2.2 |
| 36.3 | 47 | 1.5 |
| 38.6 | 42 | 1.4 |
| 41.1 | 68 | 2.2 |
| 42.2 | 90 | 3 |
| 42.7 | 64 | 2.1 |

Form V was characterized by DSC. The DSC was obtained using similar conditions as those for Form I. The DSC thermogram is shown in FIG. 11. The DSC thermogram revealed an endothermic event at an onset temperature of 206.6° C. with a peak temperature of 208.1° C.

Form V was characterized by TGA. The TGA was obtained using similar conditions as Form I. The TGA thermogram is shown in FIG. 12.

Example 7

Preparation and Characterization of Form VI

In one experiment, Form VI was prepared according to the procedures below. Approximately 3-4 mL of saturated solution of Form I in 1,4-dioxane were evaporated under air without stirring at 22±1° C. Form VI was also prepared in accordance with the procedures set forth in the examples provided herein, e.g., Example 16.

Form VI was characterized by XRPD. The XRPD was obtained using similar conditions as those for Form I. The XRPD pattern is shown in FIG. 13 and the XRPD data are provided in the table below.

TABLE 6

| 2-Theta | Height | H % |
|---|---|---|
| 4.4 | 267 | 25.8 |
| 5.2 | 1034 | 100 |
| 6.9 | 148 | 14.3 |
| 8.0 | 51 | 4.9 |
| 8.8 | 36 | 3.5 |
| 10.1 | 178 | 17.2 |
| 10.5 | 90 | 8.7 |
| 12.7 | 58 | 5.6 |
| 13.2 | 146 | 14.1 |
| 15.8 | 206 | 20 |
| 18.4 | 67 | 6.5 |
| 19.2 | 73 | 7 |
| 19.6 | 68 | 6.6 |
| 20.4 | 76 | 7.4 |
| 21.3 | 66 | 6.4 |
| 21.9 | 52 | 5.1 |
| 22.5 | 33 | 3.2 |
| 23.4 | 92 | 8.9 |
| 23.6 | 44 | 4.3 |
| 24.2 | 50 | 4.9 |
| 24.5 | 47 | 4.5 |
| 24.7 | 34 | 3.3 |
| 25.5 | 75 | 7.2 |
| 26.0 | 34 | 3.3 |
| 26.7 | 58 | 5.6 |
| 27.6 | 53 | 5.2 |
| 28.9 | 31 | 3 |
| 29.6 | 50 | 4.8 |
| 31.2 | 39 | 3.7 |
| 32.1 | 34 | 3.3 |
| 35.4 | 30 | 2.9 |
| 42.5 | 36 | 3.5 |

Example 8

Preparation and Characterization of Form VII

In one experiment, Form VII was prepared according to the procedures below. Approximately 3-4 mL of saturated solution of Form I in THF were evaporated under air without stirring at 22±1° C. Form VII was also prepared in accordance with the procedures set forth in the examples provided herein, e.g., Examples 16, 17, and 18.

Form VII was characterized by XRPD. The XRPD was obtained using similar conditions as those for Form I. The XRPD pattern is shown in FIG. 14 and the XRPD data are provided in the table below.

TABLE 7

| 2-Theta | Height | H % |
|---|---|---|
| 3.6 | 123 | 14.2 |
| 5.1 | 330 | 38.2 |
| 8.0 | 865 | 100 |
| 8.9 | 44 | 5 |
| 10.2 | 75 | 8.7 |
| 12.3 | 508 | 58.7 |
| 13.0 | 174 | 20.2 |
| 13.5 | 251 | 29.1 |
| 14.8 | 51 | 5.9 |
| 15.7 | 66 | 7.6 |
| 16.3 | 289 | 33.4 |
| 17.5 | 43 | 4.9 |
| 18.2 | 99 | 11.4 |
| 20.0 | 161 | 18.6 |
| 21.3 | 533 | 61.6 |
| 23.4 | 74 | 8.6 |
| 24.1 | 209 | 24.1 |
| 24.7 | 856 | 99 |
| 25.7 | 71 | 8.2 |
| 26.5 | 148 | 17.2 |
| 27.3 | 121 | 13.9 |

TABLE 7-continued

| 2-Theta | Height | H % |
|---|---|---|
| 28.2 | 63 | 7.3 |
| 29.7 | 71 | 8.2 |
| 31.6 | 69 | 8 |
| 32.2 | 36 | 4.1 |
| 33.3 | 36 | 4.1 |
| 37.4 | 430 | 49.7 |
| 40.0 | 57 | 6.5 |
| 42.2 | 38 | 4.4 |
| 43.7 | 74 | 8.5 |

Form VII was characterized by DSC. The DSC was obtained using similar conditions as those for Form I. The DSC thermogram is shown in FIG. 15. The DSC thermogram revealed an endothermic event at an onset temperature of 201.7° C. with a peak temperature of 204.9° C.

Form VII was characterized by TGA. The TGA was obtained using similar conditions as Form I. The TGA thermogram is shown in FIG. 16.

Example 9

Preparation and Characterization of Form VIII

In one experiment, Form VIII was prepared according to the procedures below. Approximately 3-4 mL of saturated solution of Form I in 1,4-dioxane was evaporated under air without stirring at 50±1° C. Form VIII was also prepared in accordance with the procedures set forth in the examples provided herein, e.g., Example 18.

Form VIII was characterized by XRPD. The XRPD was obtained using similar conditions as those for Form I. The XRPD pattern is shown in FIG. 17 and the XRPD data are provided in the table below.

TABLE 8

| 2-Theta | Height | H % |
|---|---|---|
| 4.5 | 188 | 18.2 |
| 8.0 | 181 | 17.5 |
| 9.0 | 477 | 46.1 |
| 12.7 | 202 | 19.5 |
| 13.3 | 230 | 22.2 |
| 14.3 | 987 | 95.5 |
| 15.5 | 198 | 19.1 |
| 16.4 | 573 | 55.4 |
| 16.9 | 104 | 10 |
| 18.1 | 902 | 87.3 |
| 19.6 | 664 | 64.2 |
| 20.2 | 281 | 27.2 |
| 20.7 | 157 | 15.2 |
| 21.7 | 135 | 13.1 |
| 23.1 | 191 | 18.5 |
| 24.0 | 1034 | 100 |
| 24.4 | 421 | 40.7 |
| 25.4 | 490 | 47.4 |
| 26.6 | 476 | 46.1 |
| 27.3 | 151 | 14.6 |
| 27.9 | 270 | 26.1 |
| 29.8 | 40 | 3.8 |
| 30.5 | 48 | 4.6 |
| 31.2 | 199 | 19.3 |
| 32.2 | 86 | 8.3 |
| 32.8 | 53 | 5.2 |
| 33.4 | 55 | 5.3 |
| 34.0 | 135 | 13 |
| 38.6 | 41 | 4 |
| 39.0 | 69 | 6.6 |
| 39.6 | 41 | 3.9 |
| 40.2 | 44 | 4.3 |
| 41.7 | 108 | 10.5 |

Form VIII was characterized by DSC. The DSC was obtained using similar conditions as those for Form I. The DSC thermogram is shown in FIG. 18. The DSC thermogram revealed an endothermic event at an onset temperature of 205.6° C. with a peak temperature of 207.3° C.

Form VIII was characterized by TGA. The TGA was obtained using similar conditions as Form I. The TGA thermogram is shown in FIG. 19.

Example 10

Preparation and Characterization of Form IX

In one experiment, Form IX was prepared according to the procedures below. To 1 mL of saturated solution of Form I prepared in chloroform was added 5.0 mL hexane to give slurry, which was filtered. Form IX was also prepared in accordance with the procedures set forth in the examples provided herein, e.g., Example 17.

Form IX was characterized by XRPD. The XRPD was obtained using similar conditions as those for Form I. The XRPD pattern is shown in FIG. 20 and the XRPD data are provided in the table below.

TABLE 9

| 2-Theta | Height | H % |
|---|---|---|
| 6.4 | 1533 | 75 |
| 8.0 | 1091 | 53.4 |
| 9.6 | 284 | 13.9 |
| 11.3 | 133 | 6.5 |
| 12.3 | 47 | 2.3 |
| 13.3 | 2043 | 100 |
| 15.3 | 479 | 23.4 |
| 16.0 | 228 | 11.1 |
| 17.9 | 303 | 14.8 |
| 18.7 | 181 | 8.9 |
| 19.0 | 191 | 9.4 |
| 19.7 | 180 | 8.8 |
| 20.5 | 251 | 12.3 |
| 21.2 | 176 | 8.6 |
| 22.4 | 838 | 41 |
| 23.3 | 214 | 10.5 |
| 24.2 | 333 | 16.3 |
| 26.6 | 177 | 8.7 |
| 27.2 | 130 | 6.4 |
| 28.2 | 109 | 5.3 |
| 28.5 | 73 | 3.6 |
| 29.3 | 41 | 2 |
| 30.8 | 50 | 2.4 |
| 31.9 | 224 | 11 |
| 35.3 | 43 | 2.1 |
| 41.3 | 52 | 2.5 |
| 42.3 | 46 | 2.3 |

Form IX was characterized by DSC. The DSC was obtained using similar conditions as those for Form I. The DSC thermogram is shown in FIG. 21. The DSC thermogram revealed an endothermic event at an onset temperature of 205.5° C. with a peak temperature of 207.2° C.

Form IX was characterized by TGA. The TGA was obtained using similar conditions as Form I. The TGA thermogram is shown in FIG. 22.

Example 11

Preparation and Characterization of Form IXa

In one experiment, Form IXa was prepared according to the procedures below. To 1 mL of saturated solution of Form I prepared in chloroform was added 7.5 mL MTBE to give slurry, which was filtered. Form IXa was also prepared in accordance with the procedures set forth in the examples provided herein, e.g., Example 17.

Form IXa was characterized by XRPD. The XRPD was obtained using similar conditions as those for Form I. The XRPD pattern is shown in FIG. 23 and the XRPD data are provided in the table below.

TABLE 10

| 2-Theta | Height | H % |
|---|---|---|
| 6.4 | 88 | 8.7 |
| 8.1 | 1005 | 100 |
| 11.3 | 600 | 59.7 |
| 12.4 | 177 | 17.7 |
| 13.2 | 178 | 17.7 |
| 13.8 | 77 | 7.7 |
| 15.4 | 935 | 93.1 |
| 16.0 | 58 | 5.8 |
| 16.7 | 56 | 5.6 |
| 17.8 | 303 | 30.1 |
| 19.0 | 409 | 40.7 |
| 19.9 | 43 | 4.3 |
| 20.5 | 366 | 36.5 |
| 21.3 | 232 | 23.1 |
| 22.8 | 358 | 35.7 |
| 23.3 | 809 | 80.5 |
| 23.9 | 341 | 33.9 |
| 24.7 | 202 | 20.1 |
| 25.0 | 207 | 20.6 |
| 26.6 | 673 | 67 |
| 27.3 | 112 | 11.1 |
| 28.3 | 234 | 23.2 |
| 30.6 | 188 | 18.7 |
| 32.0 | 111 | 11 |
| 33.8 | 102 | 10.2 |
| 36.6 | 70 | 7 |
| 40.9 | 75 | 7.5 |
| 41.2 | 61 | 6.1 |
| 41.9 | 55 | 5.5 |
| 42.3 | 101 | 10 |

Form IXa was characterized by DSC. The DSC was obtained using similar conditions as those for Form I. The DSC thermogram is shown in FIG. 24. The DSC thermogram revealed an endothermic event at an onset temperature of 206.7° C. with a peak temperature of 208.0° C.

Form IXa was characterized by TGA. The TGA was obtained using similar conditions as Form I. The TGA thermogram is shown in FIG. 25.

Example 12

Preparation and Characterization of Form X

In one experiment, Form X was prepared according to the procedures below. To 1 mL of saturated solution of Form I prepared in 1,4-dioxane was added 5.0 mL heptane to give slurry, which was filtered. Form X was also prepared in accordance with the procedures set forth in the examples provided herein, e.g., Examples 17 and 18.

Form X was characterized by XRPD. The XRPD was obtained using similar conditions as those for Form I. The XRPD pattern is shown in FIG. 26 and the XRPD data are provided in the table below.

TABLE 11

| 2-Theta | Height | H % |
|---|---|---|
| 4.4 | 5308 | 100 |
| 6.6 | 293 | 5.5 |
| 8.2 | 779 | 14.7 |
| 8.7 | 164 | 3.1 |
| 9.5 | 51 | 1 |
| 10.1 | 56 | 1.1 |
| 12.5 | 77 | 1.4 |

TABLE 11-continued

| 2-Theta | Height | H % |
|---|---|---|
| 12.9 | 409 | 7.7 |
| 16.3 | 158 | 3 |
| 16.5 | 141 | 2.6 |
| 17.2 | 58 | 1.1 |
| 18.3 | 127 | 2.4 |
| 19.8 | 74 | 1.4 |
| 21.4 | 494 | 9.3 |
| 22.4 | 502 | 9.5 |
| 23.3 | 324 | 6.1 |
| 25.8 | 767 | 14.5 |
| 29.8 | 61 | 1.2 |
| 30.8 | 206 | 3.9 |
| 32.5 | 54 | 1 |
| 33.0 | 56 | 1.1 |
| 35.1 | 81 | 1.5 |
| 38.1 | 49 | 0.9 |
| 39.0 | 88 | 1.7 |
| 39.5 | 60 | 1.1 |
| 42.4 | 139 | 2.6 |
| 43.6 | 94 | 1.8 |
| 43.8 | 76 | 1.4 |

Example 13

Preparation and Characterization of Form XI

In one experiment, Form XI was prepared according to the procedures below. To 5.0 mL of heptane was added 1.5 mL of saturated solution of Form I prepared in dichloromethane to give slurry, which was filtered. Form XI was also prepared in accordance with the procedures set forth in the examples provided herein, e.g., Example 18.

Form XI was characterized by XRPD. The XRPD was obtained using similar conditions as those for Form I. The XRPD pattern is shown in FIG. 27 and the XRPD data are provided in the table below.

TABLE 12

| 2-Theta | Height | H % |
|---|---|---|
| 4.6 | 104 | 1.9 |
| 6.5 | 91 | 1.6 |
| 8.2 | 5604 | 100 |
| 9.1 | 58 | 1 |
| 9.8 | 269 | 4.8 |
| 12.2 | 83 | 1.5 |
| 13.5 | 1859 | 33.2 |
| 14.5 | 45 | 0.8 |
| 15.4 | 66 | 1.2 |
| 15.6 | 58 | 1 |
| 16.1 | 731 | 13 |
| 18.0 | 362 | 6.5 |
| 18.9 | 186 | 3.3 |
| 19.7 | 185 | 3.3 |
| 20.5 | 134 | 2.4 |
| 21.3 | 104 | 1.9 |
| 22.7 | 1590 | 28.4 |
| 23.6 | 507 | 9 |
| 24.3 | 330 | 5.9 |
| 24.7 | 171 | 3 |
| 25.6 | 47 | 0.8 |
| 26.2 | 84 | 1.5 |
| 27.3 | 344 | 6.1 |
| 28.1 | 150 | 2.7 |

TABLE 12-continued

| 2-Theta | Height | H % |
|---|---|---|
| 28.8 | 113 | 2 |
| 30.2 | 44 | 0.8 |
| 31.4 | 76 | 1.3 |
| 32.5 | 572 | 10.2 |
| 34.0 | 112 | 2 |
| 35.2 | 58 | 1 |
| 36.4 | 61 | 1.1 |
| 38.1 | 37 | 0.7 |
| 41.4 | 52 | 0.9 |
| 42.4 | 311 | 5.5 |

Form XI was characterized by DSC. The DSC was obtained using similar conditions as those for Form I. The DSC thermogram is shown in FIG. 28. The DSC thermogram revealed an endothermic event at an onset temperature of 206.5° C. with a peak temperature of 207.6° C.

Form XI was characterized by TGA. The TGA was obtained using similar conditions as Form I. The TGA thermogram is shown in FIG. 29.

Example 14

Solubility Measurement

The solubility of the Compound 1 Form I was measured according to Procedure 1 for solubility in 23±1° C. (Table 13) and Procedure 2 for 50±1° C. (Table 14) and the results are summarized in Table 15.

Compound 1 Form I is completely soluble (>50 mg/mL) in DMSO, DMF, DCM/MeOH (1:1), and THF/water (4:1) at 23° C. and 50° C., and in acetone/water (4:1) and chloroform at 50° C. It is insoluble (<1 mg/mL) in heptane, hexane, toluene, MTBE, isobutyl acetate, IPAc, water, and acetone water (1:4) at 23° C. and 50° C., and in MIBK, EtOAc, IPA, and acetone water (1:2) at 23° C. It is slightly soluble (1-50 mg/mL) in MeCN, 1,4-dioxane, MeOH, 2-methoxyethanol, THF, acetone, n-BuOH, EtOH, ethyl formate, 1-propanol, MEK, acetone water (2:1), and acetone water (1:1) at 23° C. and 50° C., and in chloroform and dichloromethane at 23° C., and in MIBK, EtOAc, IPA, and acetone water (1:2) at 50° C.

TABLE 13

Procedure 1 for solubility measurement of Compound 1 Form I in various solvents at 23 ± 1° C.

| Op# | Operation |
|---|---|
| 1 | Added 2 mL solvents listed in the Table 15 to the individual vials |
| 2 | Added Compound 1 Form I to cloudy solution at 23 ± 1° C. |
| 3 | Added another about 20 mg Compound 1 Form I |
| 4 | Agitated the mixture at 23 ± 1° C. over the weekend, which is controlled by IKA ® ETS-D5 temperature controller and IKA ® RCT basic safety control |
| 5 | Filtered the supernatant using syringe filter (PTFE, 0.22 µm, 13 mm, Agela Technologies Inc.) |
| 6 | Pipetted the saturated solution into HPLC vials. |
| 7 | Diluted the saturated solution in HPLC vials with acetonitrile. |
| 8 | HPLC analysis |
| 9 | Calculated solubility as indicated in Table 15 |

TABLE 14

Procedure 2 for solubility measurement of Compound 1 Form I in various solvents at 50 ± 1° C.

| Op# | Operation |
|---|---|
| 1 | Added 2 mL solvents listed in the Table 15 to the individual vials |
| 2 | Added Compound 1 Form I to cloudy solution at 50° C. |
| 3 | Added another about 30-40 mg Compound 1 Form I |
| 4 | Agitated the mixture at 50 ± 1° C. for 24 h, which is controlled by IKA ® ETS-D5 temperature controller and IKA ® RCT basic safety control |
| 5 | Filtered quickly the supernatant using warmed syringe filter at 50 ± 1° C. (PTFE, 0.22 µm, 13 mm, Agela Technologies Inc.) |
| 6 | Pipetted the saturated solution into HPLC vials |
| 7 | Diluted the saturated solution in HPLC vials with acetonitrile. |
| 8 | HPLC analysis and calculated solubility as indicated in Table 15 |

TABLE 15

Solubility of Compound 1 Form I in various solvents

| Solvent | Solubility at 23 ± 1° C. (mg/mL) | Solubility at 50 ± 1° C. (mg/mL) |
|---|---|---|
| MeCN | 4.59 | 11.57 |
| Chloroform[1] | 26.66 | >50 |
| Dichloromethane | 12.45 | N/A |
| DMF | >50 | >50 |
| 1,4-Dioxane[2] | 3.02 | 37.78 |
| Methanol | 5.35 | 17.86 |
| 2-Methoxyethanol | 20.20 | 36.63 |
| MIBK | 0.91 | 2.95 |
| Toluene[3] | 0.15 | 0.17 |
| Hexane | 0.00 | 0.06 |
| THF | 3.77 | 11.31 |
| Acetone | 5.10 | 15.52 |
| n-BuOH | 1.18 | 6.20 |
| MTBE | 0.00 | 0.00 |
| DMSO | >50 | >50 |
| EtOH | 2.01 | 8.56 |
| EtOAc | 0.89 | 2.71 |
| Ethyl formate | 2.20 | 6.58 |
| Heptane | 0.00 | 0.00 |
| Isobutyl acetate | 0.28 | 0.75 |
| IPAc | 0.44 | 0.98 |
| 1-Propanol | 1.72 | 2.89 |
| IPA | 0.90 | 2.22 |
| Water | 0.01 | 0.01 |
| MEK | 3.58 | 3.73 |
| DCM/MeOH (1:1) | >50 | >50 |
| THF/water (4:1) | >50 | >50 |
| Acetone/water (4:1) | 19.41 | >50 |
| Acetone/water (2:1) | 12.47 | 46.97 |
| Acetone/water (1:1) | 3.97 | 12.63 |
| Acetone/water (1:2) | 0.86 | 3.53 |
| Acetone/water (1:4) | 0.17 | 0.57 |

Note:
[1]Solubility of Form II in chloroform;
[2]Solubility of Form III in 1,4-Dioxane;
[3]Solubility of Form IV in Toluene.

Example 15

Phase Equilibration at 23±1° C. and 50±1° C.

Phase equilibration studies were designed to provide information on a predominant crystal form for phase identification. Based on its solubility in various solvent systems in Example 14, Compound 1 was equilibrated in a representative group of solvents at 23±1° C. (Table 16) and 50±1° C. (Table 17). To the solvents listed in Table 16 (23±1° C.) and Table 17 (50±1° C.) was added Compound 1 Form I until a cloudy solution was obtained, then about 20-40 mg of Compound 1 Form I was added to the cloudy solution. The mixture was stirred at 23±1° C. over weekend and 50±1° C. for 2 days. The solid was filtered and analyzed by XRPD to give the results in Table 16 and Table 17.

Three new polymorphic forms were found by XRPD in the phase equilibration at 23±1° C. including Form II (chloroform), Form III (1,4-dioxane), and Form IV (toluene). Form III (1,4-dioxane) was also identified in the phase equilibration at 50±1° C.

TABLE 16

Crystal form for phase equilibration at 23 ± 1° C.

| No. | Solvent | Solid State Form |
|---|---|---|
| 1 | Acetonitrile | I |
| 2 | Chloroform | II |
| 3 | DCM | I |
| 4 | 1,4-Dioxane | III |
| 5 | Methanol | I |
| 6 | 2-Methoxyethanol | I |
| 7 | MIBK | I |
| 8 | Toluene | IV |
| 9 | Hexane | I |
| 10 | THF | I |
| 11 | Acetone | I |
| 12 | n-BuOH | I |
| 13 | MTBE | I |
| 14 | EtOH | I |
| 15 | EtOAc | I |
| 16 | Ethyl formate | I |
| 17 | Heptane | I |
| 18 | Isobutyl acetate | I |
| 19 | IPAc | I |
| 20 | 1-Propanol | I |
| 21 | IPA | I |
| 22 | Water | I |
| 23 | MEK | I |
| 24 | Acetone/water (4:1) | I |
| 25 | Acetone/water (2:1) | I |
| 26 | Acetone/water (1:1) | I |
| 27 | Acetone/water (1:2) | I |
| 28 | Acetone/water (1:4) | I |

TABLE 17

Crystal form for phase equilibration at 50 ± 1° C.

| No. | Solvent | Solid State Form |
|---|---|---|
| 1 | Acetonitrile | I |
| 2 | Chloroform | I |
| 3 | 1,4-Dioxane | III |
| 4 | Methanol | I |
| 5 | 2-Methoxyethanol | I |
| 6 | MIBK | I |
| 7 | Toluene | I |
| 8 | Hexane | I |
| 9 | THF | I |
| 10 | Acetone | I |
| 11 | n-BuOH | I |
| 12 | MTBE | I |
| 13 | EtOH | I |
| 14 | EtOAc | I |
| 15 | Ethyl formate | I |
| 16 | Heptane | I |
| 17 | Isobutyl acetate | I |
| 18 | IPAc | I |
| 19 | 1-Propanol | I |
| 20 | IPA | I |
| 21 | Water | I |
| 22 | MEK | I |
| 23 | DCM/MeOH (1:1) | I |
| 24 | Acetone/water (4:1) | I |
| 25 | Acetone/water (2:1) | I |
| 26 | Acetone/water (1:1) | I |
| 27 | Acetone/water (1:2) | I |

TABLE 17-continued

Crystal form for phase equilibration at 50 ± 1° C.

| No. | Solvent | Solid State Form |
|---|---|---|
| 28 | Acetone/water (1:4) | I |

Example 16

Evaporation at 23±1° C. and 50±1° C.

Evaporation studies were carried out to identify the predominant crystal form during uncontrolled precipitation. Experiments that did not result in any particulate solids (i.e. clear thin films and oils) were not studied further. XRPD was used to study the solid-state morphology of the crystalline forms of the evaporation samples at 23±1° C. and 50±1° C. The results are presented in Table 18 (23±1° C.) and Table 19 (50±1° C.).

Evaporation at 23±1° C. (Table 18) resulted in new polymorphic Form V (chloroform), Form VI (1,4-dioxane), and Form VII (THF). Evaporation at 50±1° C. (Table 19) resulted in new polymorphic Form VIII (1,4-dioxane).

TABLE 18

Crystal form identification from evaporation at 23 ± 1° C.

| No. | Solvent | Solid State Form |
|---|---|---|
| 1 | Acetonitrile | I |
| 2 | Chloroform | V |
| 3 | DCM | I |
| 4 | DMF | I |
| 5 | 1,4-Dioxane | VI |
| 6 | Methanol | I |
| 7 | 2-Methoxyethanol | |
| 8 | MIBK | N/A |
| 9 | THF | VII |
| 10 | Acetone | I |
| 11 | n-BuOH | N/A |
| 12 | DMSO | I |
| 13 | EtOH | I |
| 14 | EtOAc | N/A |
| 15 | Ethyl formate | I |
| 16 | Isobutyl acetate | N/A |
| 17 | IPAc | I |
| 18 | 1-Propanol | I |
| 19 | IPA | I |
| 20 | MEK | I |
| 21 | DCM/MeOH (1:1) | I |
| 22 | THF/water (4:1) | I |
| 23 | Acetone/water (4:1) | I |
| 24 | Acetone/water (2:1) | I |

TABLE 19

Crystal form identification from evaporation at 50 ± 1° C.

| No. | Solvent | Solid State Form |
|---|---|---|
| 1 | Acetonitrile | I |
| 2 | Chloroform | I |
| 3 | DCM | I |
| 4 | DMF | I |
| 5 | 1,4-Dioxane | VIII |
| 6 | Methanol | I |
| 7 | 2-Methoxyethanol | I |
| 8 | MIBK | N/A |
| 9 | THF | I |
| 10 | Acetone | I |
| 11 | n-BuOH | I |
| 12 | EtOH | I |
| 13 | EtOAc | I |
| 14 | Ethyl formate | I |
| 15 | Isobutyl acetate | I |
| 16 | IPAc | N/A |
| 17 | 1-Propanol | I |
| 18 | IPA | I |
| 19 | MEK | I |
| 20 | DCM/MeOH (1:1) | I |
| 21 | THF/water (4:1) | I |
| 22 | Acetone/water (4:1) | I |
| 23 | Acetone/water (2:1) | I |
| 24 | Acetone/water (1:1) | I |
| 25 | Acetone/water (1:2) | I |
| 26 | Acetone/water (1:4) | I |

Example 17

Anti-Solvent Addition

Saturated solutions of Compound 1 were prepared by adding the compound (Compound 1 Form I) to the solvents respectively. An anti-solvent was added to induce precipitation. MTBE, toluene, water, heptane, and hexane were selected as the anti-solvents. Experiments that did not produce any particulate solids on anti-solvent addition were not studied further. The results are presented in Table 20. Antisolvent addition resulted in Form IX (chloroform-hexane), Form IXa (chloroform-MTBE), Form X (1,4-dioxane-heptane and 1,4-dioxane-hexane), and Form VII (THF-hexane).

TABLE 20

Antisolvent addition of Compound 1 Form I in various solvents

| No. | Solvent (mL) | Anti-solvent (mL) | Form |
|---|---|---|---|
| 1 | Chloroform (1.0) | Heptane (5.0) | I |
| 2 | Chloroform (1.0) | Hexane (5.0) | IX |
| 3 | Chloroform (1.0) | MTBE (7.5) | IXa |
| 4 | Chloroform (1.0) | Toluene (5.0) | N/A |

TABLE 20-continued

Antisolvent addition of Compound 1 Form I in various solvents

| No. | Solvent (mL) | Anti-solvent (mL) | Form |
|---|---|---|---|
| 5 | Dichloro-methane (2.0) | Heptane (5.0) | I |
| 6 | Dichloro-methane (2.0) | Hexane (5.0) | I |
| 7 | Dichloro-methane (2.0) | MTBE (5.0) | I |
| 8 | Dichloro-methane (2.0) | Toluene (5.0) | N/A |
| 9 | 1,4-Dioxane (1..0)* | Heptane (5.0) | X |
| 10 | 1,4-Dioxane (1.0)* | Hexane (5.0) | X |
| 11 | 1,4-Dioxane | MTBE | N/A |
| 12 | 1,4-Dioxane | Toluene | N/A |
| 13 | Methanol (1.0) | MTBE (5.0) | N/A |
| 14 | Methanol (1.0) | Toluene (5.0) | N/A |
| 15 | 2-Methoxy-ethanol (1.0) | MTBE (5.0) | N/A |
| 16 | THF (5.0) | Heptane (2.0) | I |
| 17 | THF (5.0) | Hexane (2.0) | VII |
| 18 | THF (5.0) | MTBE (1.5) | N/A |
| 19 | Acetone (5.0) | Heptane (2.5) | I |
| 20 | Acetone (5.0) | Hexane (2.5) | I |
| 21 | Acetone (5.0) | MTBE (2.5) | N/A |
| 22 | Acetone (5.0) | Toluene (2.5) | N/A |
| 23 | DCM/MeOH (1:1, 1.5 mL) | Heptane (5.0) | I |
| 24 | DCM/MeOH (1:1, 1.5 mL) | Hexane (5.0) | I |
| 25 | DCM/MeOH (1:1, 1.5 mL) | MTBE (5.0) | I |
| 26 | DCM/MeOH (1:1, 1.5 mL) | Toluene (5.0) | N/A |
| 27 | THF/water (4:1, 1.0 mL) | MTBE (5.0) | I |
| 28 | THF/water (4:1, 1.0 mL) | Toluene (5.0) | I |

*The saturated solution was prepared at 30° C.

Example 18

Reverse Addition

Saturated solutions of Compound 1 Form I were prepared in solvents listed in Table 21, and added to a larger volume of a miscible anti-solvent. Experiments that did not produce any particulate solids upon addition to the anti-solvent were not studied further. Reverse addition resulted in Form XI (dichloromethane-heptane), Form X (1,4-dioxane-heptane and 1,4-dioxane-hexane), and Form VII (THF-hexane).

TABLE 21

Reverse addition of INCB062079 in various solvents

| No. | Solvent (mL) | Anti-solvent (mL) | Form |
|---|---|---|---|
| 1 | Acetonitrile (1.0) | MTBE (5.0) | N/A |
| 2 | Chloroform (1.0) | Heptane (5.0) | I |
| 3 | Chloroform (1.0) | Hexane (5.0) | I |
| 4 | Chloroform (1.0) | MTBE (7.5) | I |
| 5 | Chloroform (1.0) | Toluene (5.0) | N/A |
| 6 | Dichloromethane (1.5) | Heptane (5.0) | XI |
| 7 | Dichloromethane (1.5) | Hexane (5.0) | XI (major) + I |
| 8 | Dichloromethane (2.0) | MTBE (5.0) | I |
| 9 | Dichloromethane (1.5) | Toluene (5.0) | N/A |
| 10 | 1,4-Dioxane* (2.0) | Heptane (5.0) | X |
| 11 | 1,4-Dioxane* (2.0) | Hexane (5.0) | X |
| 12 | 1,4-Dioxane* (2.0) | MTBE (5.0) | N/A |
| 13 | Methanol (1.5) | MTBE (6.0) | N/A |
| 14 | THF (2.0) | Heptane (5.0) | I |
| 15 | THF (2.0) | Hexane (5.0) | VII |
| 16 | THF (1.5) | MTBE (5.0) | N/A |
| 17 | Acetone (2.0) | Heptane (5.0) | I |
| 18 | Acetone (2.5) | Hexane (5.0) | I |
| 19 | Acetone (2.5) | MTBE (5.0) | N/A |
| 20 | Acetone (2.5) | Toluene (5.0) | N/A |
| 21 | DCM/MeOH (1:1, 1.5) | Heptane (5.0) | I |
| 22 | DCM/MeOH (1:1, 1.5) | Hexane (5.0) | I |
| 23 | DCM/MeOH (1:1, 1.5) | MTBE (5.0) | I |
| 24 | DCM/MeOH (1:1, 1.5) | Toluene (5.0) | N/A |
| 25 | THF/water (4:1, 1.0) | Heptane (5.0) | I |
| 26 | THF/water (4:1, 1.0) | Hexane (5.0) | I |
| 27 | THF/water (4:1, 1.0) | MTBE (5.0) | I |
| 28 | THF/water (4:1, 1.0) | Toluene (5.0) | I |
| 29 | THF/water (4:1, 1.0) | Water (5.0) | I |

Example 19

Quench Cool of Saturated Solution

Saturated solutions of Compound Form I prepared at about 35° C. were quenched cooled to induce precipitation of higher energy forms. Representative solvents were chosen based on solubility data measured at 23° C. and 50° C. The studied solvents and the crystal form of the sample in each of the solvent were shown in Table 22. Quench cooling resulted in Form II (chloroform) and Form III (1,4-dioxane).

TABLE 22

Crystal form identification for Compound 1 Form I from quench cool

| No. | Solvent | Form |
|---|---|---|
| 1 | MeCN (cooled to −15° C.) | I |
| 2 | Chloroform (cooled to −5° C.) | II |
| 3 | 1,4-Dioxane (cooled to 13° C.) | III |
| 4 | Methanol (cooled to −15° C.) | I |
| 5 | 2-Methoxyethanol (cooled to −15° C.) | I |
| 6 | THF | |

TABLE 22-continued

Crystal form identification for Compound 1 Form I from quench cool

| No. | Solvent | Form |
|---|---|---|
| 7 | Acetone (cooled to −15° C.) | I |
| 8 | n-BuOH (cooled to −15° C.) | |
| 9 | Acetone/water (4:1) (cooled to 5° C.) | I |
| 10 | Acetone/water (2:1) (cooled to 5° C.) | I |
| 12 | Acetone/water (1:1) (cooled to 5° C.) | I |

Example 20

Crystallization of Saturated Solution with Heating and Cooling Cycles

Saturated solutions of Compound 1 Form I were prepared at 50° C., and cooled in a bath slowly by using a programmed circulating bath. To the clear solution was added about 10 mg of Compound 1 Form I to give slurry. The formed slurry was then heated to 50° C. over 2 hours and then cooled down to 5° C. over 2 hours. This process was repeated for 3 days and the solid was filtered for further analysis. The results are presented in Table 23. Heating and cooling cycles resulted in Form V (chloroform) and Form III (1,4-dioxane).

TABLE 23

Crystallization of saturated solution of Compound 1 with heating and cooling recycles

| No. | Solvent | Form |
|---|---|---|
| 1 | MeCN | I |
| 2 | Chloroform | V |
| 3 | 1,4-Dioxane | III |
| 4 | Methanol | I |
| 5 | 2-Methoxyethanol | I |
| 6 | THF | I |
| 7 | Acetone | I |
| 8 | Acetone/water (4:1) | I |
| 9 | Acetone/water (2:1) | I |
| 10 | Acetone/water (1:1) | I |
| 11 | Acetone/water (1:2) | I |
| 12 | Acetone/water (1:4) | I |

Example 21

Studies of Stability Relationship of Compound 1 Forms

To evaluate the transformation of Compound 1 solid forms, competitive slurry experiments in production crystallization solvents at 23-25° C. were performed with a mixture of twelve (12) polymorphs (Form I through Form XI) according to the procedures in Table 25 (acetone/water 2:1) and Table 26 (acetone/water 1:1). The mixture of forms (Form I through Form XI) was converted to Form I after stirring for 3.5 hours as shown by XRPD (data not shown). These results indicate that the Form I is the most stable polymorphic form in acetone/water (2:1) and acetone/water (1:1).

TABLE 24

Mixed samples in different solvents (competitive slurries) 23-25° C.

| No. | Solvent | Solid State Form (after stirring 3.5 h) | Solid State Form (after stirring 24 h) |
|---|---|---|---|
| 1 | Acetone/water (2:1) | Form I | Form I |
| 2 | Acetone/water (1:1) | Form I | Form I |

TABLE 25

Procedure for competitive experiment in Acetone/water (2:1) at 23-25° C.

| OP# | Operation |
|---|---|
| 1 | Added saturated solution of Form I (1.5 mL) in Acetone/water (2:1) |
| 2 | Added 3 mg of Form I, and stirred to give a cloudy solution |
| 3 | Added the mixture of 3 mg each of Form II, III, IV, V, VI, VII, VIII, IX, IXa, X and XI |
| 4 | Stirred for 3.5 h at 23-25° C.: XRPD shows Form I |
| 5 | Stirred for 26 h at 25.5-28.8° C.: XRPD shows Form I |

TABLE 26

Procedure for competitive experiment in Acetone/water (1:1) at 23-25° C.

| OP# | Operation |
|---|---|
| 1 | Added saturated solution of Compound 1 Form I (1.5 mL) in acetone/water (1:1) |
| 2 | Added 3 mg of Form I and stirred to give a cloudy solution, |
| 3 | Added the mixture of 3 mg each of Form II, III, IV, V, VI, VII, VIII, IX, IXa, X and XI |
| 4 | Stirred for 3.5 h at 23-25° C.: XRPD shows Form I |
| 5 | Stirred for 26 h at 25.5-28.8° C.: XRPD shows Form I |

Example A

FGFR Enzymatic Assay

The inhibitor potency of the exemplified compounds is measured in an enzyme assay that measures peptide phosphorylation using FRET measurements to detect product formation. Inhibitors are serially diluted in DMSO and a volume of 0.5 µL is transferred to the wells of a 384-well plate. For FGFR3, a 10 µL volume of FGFR3 enzyme (Millipore) diluted in assay buffer (50 mM HEPES, 10 mM $MgCl_2$, 1 mM EGTA, 0.01% Tween-20, 5 mM DTT, pH 7.5) is added to the plate and pre-incubated for a time between 5-10 minutes and up to 4 hours. Appropriate controls (enzyme blank and enzyme with no inhibitor) are included on the plate. The assay is initiated by the addition of a 10 µL solution containing biotinylated EQEDEPEGDYFEWLE peptide substrate (SEQ ID NO: 1) and ATP (final concentrations of 500 nM and 140 µM respectively) in assay buffer to the wells. The plate was incubated at 25° C. for 1 hr. The reactions are ended with the addition of 10 µL/well of quench solution (50 mM Tris, 150 mM NaCl, 0.5 mg/mL BSA, pH 7.8; 30 mM EDTA with Perkin Elmer Lance Reagents at 3.75 nM Eu-antibody PY20 and 180 nM APC-Streptavidin). The plate is allowed to equilibrate for ~1 hr before scanning the wells on a PheraStar plate reader (BMG Labtech).

FGFR1, FGFR2, and FGFR4 are measured under equivalent conditions with the following changes in enzyme and ATP concentrations: FGFR1, 0.02 nM and 210 uM respectively, FGFR2, 0.01 nM and 100 uM, respectively, and FGFR4, 0.04 nM and 600 uM respectively. The enzymes can be purchased from Millipore or Invitrogen.

GraphPad prism3 is used to analyze the data. The $IC_{50}$ values are derived by fitting the data to the equation for a sigmoidal dose-response with a variable slope. Y=Bottom+(Top−Bottom)/(1+10^((Log $IC_{50}$−X)*HillSlope)) where X is the logarithm of concentration and Y is the response. Compounds having an $IC_{50}$ of 1 µM or less are considered active.

Example B

FGFR4 Cellular and In Vivo Assays

The FGFR4 inhibitory activity of the example compounds in cells, tissues, and/or animals can be demonstrated according to one or more assays or models described in the art such as, for example, in French et al. "Targeting FGFR4 Inihibits Hepatocellular Carcinoma in Preclinical Mouse Models," PLoS ONE, May 2012, Vol. 7, Issue 5, e36713, which is incorporated herein by reference in its entirety.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

---

---

What is claimed is:

1. A solid form of Compound 1 having the formula:

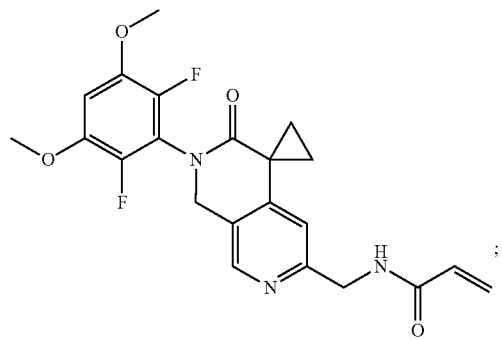

(Compound 1)

wherein the solid form is crystalline having Form I, wherein Form I has one or more characteristic XRPD peak selected from about 8.1, about 9.0, about 11.5, about 12.3, about 15.1, about 16.0, about 18.0, about 19.6, about 20.0, about 20.4, about 21.0, about 23.3, about 24.2, about 24.7, and about 27.1 degrees 2-theta.

2. The solid form of claim 1 having at least two characteristic XRPD peaks selected from about 8.1, about 9.0, about 11.5, about 12.3, about 15.1, about 16.0, about 18.0, about 19.6, about 20.0, about 20.4, about 21.0, about 23.3, about 24.2, about 24.7, and about 27.1 degrees 2-theta.

3. The solid form of claim 1 having at least three characteristic XRPD peaks selected from about 8.1, about 9.0, about 11.5, about 12.3, about 15.1, about 16.0, about 18.0, about 19.6, about 20.0, about 20.4, about 21.0, about 23.3, about 24.2, about 24.7, and about 27.1 degrees 2-theta.

4. The solid form of claim 1 having an XRPD pattern with characteristic peaks as substantially shown in FIG. 1.

5. The solid form of claim 1 exhibits a DSC thermogram having an endotherm peak at a temperature of about 208° C.

6. The solid form of claim 1 having a DSC thermogram substantially as depicted in FIG. 2.

7. The solid form of claim 1 having a TGA thermogram substantially as depicted in FIG. 3.

8. A solid form of Compound 1 having the formula:

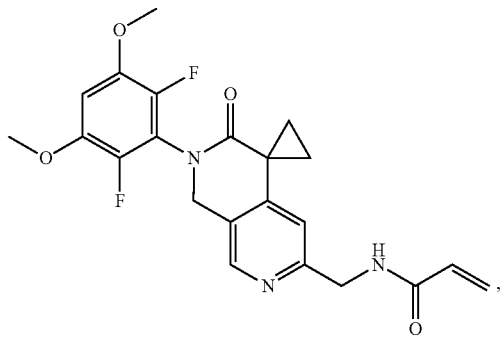

(Compound 1)

wherein the solid form is crystalline; and has Form II, Form III, Form IV, Form V, Form VI, Form VII, Form VIII, Form IX, Form IXa, Form X, or Form XI; and wherein Form II has one or more characteristic XRPD peak selected from about 11.4, about 12.6, about 14.5, about 14.7, about 16.1, about 18.3, about 21.2, about 24.8, about 27.9, and about 28.3 degrees 2-theta;

Form III has one or more characteristic XRPD peak selected from about 4.2, about 7.6, about 8.0, about 12.5, about 13.2, about 15.2, about 16.0, about 19.3, about 20.7, and about 25.6 degrees 2-theta;

Form IV has one or more characteristic XRPD peaks selected from about 4.3, about 11.9, about 12.9, about 14.3, about 15.1, about 15.5, about 18.0, about 23.3, about 24.5, about 25.1, and about 26.8 degrees 2-theta;

Form V has one or more characteristic XRPD peaks selected from about 6.6, about 8.2, about 9.2, about 11.5, about 13.5, about 15.6, about 17.9, about 19.4, about 20.7, about 23.5, and about 26.8 degrees 2-theta;

Form VI has one or more characteristic XRPD peaks selected from about 4.4, about 5.2, about 6.8, about 10.1, about 10.5, about 12.7, about 13.2, about 15.8, about 18.4, about 19.2, about 19.6, and about 20.4 degrees 2-theta;

Form VII has one or more characteristic XRPD peaks selected from about 5.1, about 8.0, about 10.2, about 12.3, about 13.0, about 13.5, about 15.6, about 16.3, about 18.2, about 21.3, about 24.7, and about 37.4 degrees 2-theta;

Form VIII has one or more characteristic XRPD peaks selected from about 4.5, about 8.0, about 9.0, about 12.7, about 13.3, about 14.3, about 15.5, about 16.4, about 18.1, about 19.6, about 20.2, about 20.7, about 24.0, about 25.4, and about 26.6 degrees 2-theta;

Form IX has one or more characteristic XRPD peaks selected from about 6.4, about 8.0, about 9.6, about 13.3, about 15.3, about 16.0, about 17.9, about 18.7, about 19.7, about 20.5, about 22.4, about 23.3, about 24.2 degrees 2-theta;

Form IXa has one or more characteristic XRPD peaks selected from about 6.4, about 8.1, about 11.3, about 12.4, about 13.2, about 15.4, about 17.8, about 19.0, about 20.5, about 21.3, about 22.8, about 23.3, about 23.9, and about 26.6 degrees 2-theta;

Form X has one or more characteristic XRPD peaks selected from about 4.4, about 6.6, about 8.2, about 8.8, about 12.9, about 16.3, about 21.4, about 22.4, about 23.3, and about 25.8 degrees 2-theta; and Form XI has one or more characteristic XRPD peaks selected from about 8.2, about 9.8, about 13.5, about 16.1, about 18.0, about 18.9, about 19.7, about 20.5, about 22.7, and about 23.6 degrees 2-theta.

9. A pharmaceutical composition comprising a solid form of claim 1, and one or more pharmaceutically acceptable carriers or excipients.

10. The solid form of claim 8, having Form II.

11. The solid form of claim 10, having at least two characteristic XRPD peaks selected from about 11.4, about 12.6, about 14.5, about 14.7, about 16.1, about 18.3, about 21.2, about 24.8, about 27.9, and about 28.3 degrees 2-theta.

12. The solid form of claim 10, having an XRPD pattern with characteristic peaks as substantially shown in FIG. 4.

13. The solid form of claim 10, which exhibits a DSC thermogram having an endotherm peak at a temperature of about 208° C.

14. The solid form of claim 10, which exhibits a DSC thermogram substantially as depicted in FIG. 5.

15. The solid form of claim 8, having Form III.

16. The solid form of claim 15, having at least two characteristic XRPD peaks selected from about 4.2, about 7.6, about 8.0, about 12.5, about 13.2, about 15.2, about 16.0, about 19.3, about 20.7, and about 25.6 degrees 2-theta.

17. The solid form of claim 15, having an XRPD pattern with characteristic peaks as substantially shown in FIG. 6.

18. The solid form of claim 15, which exhibits a DSC thermogram having an endotherm peak at a temperature of about 207° C.

19. The solid form of claim 15, which exhibits a DSC thermogram substantially as depicted in FIG. 7.

20. The solid form of claim 8, having Form IV.

21. The solid form of claim 20, having at least two characteristic XRPD peaks selected from about 4.3, about 11.9, about 12.9, about 14.3, about 15.1, about 15.5, about 18.0, about 23.3, about 24.5, about 25.1, and about 26.8 degrees 2-theta.

22. The solid form of claim 20, having an XRPD pattern with characteristic peaks as substantially shown in FIG. 8.

23. The solid form of claim 20, which exhibits a DSC thermogram having an endotherm peak at a temperature of about 208° C.

24. The solid form of claim 20, which exhibits a DSC thermogram substantially as depicted in FIG. 9.

25. The solid form of claim 8, having Form V.

26. The solid form of claim 25, having at least two characteristic XRPD peaks selected from about 6.6, about 8.2, about 9.2, about 11.5, about 13.5, about 15.6, about 17.9, about 19.4, about 20.7, about 23.5, and about 26.8 degrees 2-theta.

27. The solid form of claim 25, having an XRPD pattern with characteristic peaks as substantially shown in FIG. 10.

28. The solid form of claim 25, which exhibits a DSC thermogram having an endotherm peak at a temperature of about 208° C.

29. The solid form of claim 25, which exhibits a DSC thermogram substantially as depicted in FIG. 11.

30. The solid form of claim 25, which exhibits a TGA thermogram substantially as depicted in FIG. 12.

31. The solid form of claim 8, having Form VI.

32. The solid form of claim 31, having at least two characteristic XRPD peaks selected from about 4.4, about 5.2, about 6.8, about 10.1, about 10.5, about 12.7, about 13.2, about 15.8, about 18.4, about 19.2, about 19.6, and about 20.4 degrees 2-theta.

33. The solid form of claim 31, having an XRPD pattern with characteristic peaks as substantially shown in FIG. 13.

34. The solid form of claim 8, having Form VII.

35. The solid form of claim 34, having at least two characteristic XRPD peaks selected from about 5.1, about 8.0, about 10.2, about 12.3, about 13.0, about 13.5, about 15.6, about 16.3, about 18.2, about 21.3, about 24.7, and about 37.4 degrees 2-theta.

36. The solid form of claim 34, having an XRPD pattern with characteristic peaks as substantially shown in FIG. 14.

37. The solid form of claim 34, which exhibits a DSC thermogram having an endotherm peak at a temperature of about 205° C.

38. The solid form of claim 34, which exhibits a DSC thermogram substantially as depicted in FIG. 15.

39. The solid form of claim 34, which exhibits a TGA thermogram substantially as depicted in FIG. 16.

40. The solid form of claim 8, having Form VIII.

41. The solid form of claim 40, having at least two characteristic XRPD peaks selected from about 4.5, about 8.0, about 9.0, about 12.7, about 13.3, about 14.3, about 15.5, about 16.4, about 18.1, about 19.6, about 20.2, about 20.7, about 24.0, about 25.4, and about 26.6 degrees 2-theta.

42. The solid form of claim 40, having an XRPD pattern with characteristic peaks as substantially shown in FIG. 17.

43. The solid form of claim 40, which exhibits a DSC thermogram having an endotherm peak at a temperature of about 207° C.

44. The solid form of claim 40, which exhibits a DSC thermogram substantially as depicted in FIG. 18.

45. The solid form of claim 40, which exhibits a TGA thermogram substantially as depicted in FIG. 19.

46. The solid form of claim 8, having Form IX.

47. The solid form of claim 46, having at least two characteristic XRPD peaks selected from about 6.4, about 8.0, about 9.6, about 13.3, about 15.3, about 16.0, about 17.9, about 18.7, about 19.7, about 20.5, about 22.4, about 23.3, about 24.2 degrees 2-theta.

48. The solid form of claim 46, having an XRPD pattern with characteristic peaks as substantially shown in FIG. 20.

49. The solid form of claim 46, which exhibits a DSC thermogram having an endotherm peak at a temperature of about 207° C.

50. The solid form of claim 46, which exhibits a DSC thermogram substantially as depicted in FIG. 21.

51. The solid form of claim 46, which exhibits a TGA thermogram substantially as depicted in FIG. 22.

52. The solid form of claim 8, having Form IXa.

53. The solid form of claim 52, having at least two characteristic XRPD peaks selected from about 6.4, about 8.1, about 11.3, about 12.4, about 13.2, about 15.4, about 17.8, about 19.0, about 20.5, about 21.3, about 22.8, about 23.3, about 23.9, and about 26.6 degrees 2-theta.

54. The solid form of claim 52, having an XRPD pattern with characteristic peaks as substantially shown in FIG. 23.

55. The solid form of claim 52, which exhibits a DSC thermogram having an endotherm peak at a temperature of about 208° C.

56. The solid form of claim 52, which exhibits a DSC thermogram substantially as depicted in FIG. 24.

57. The solid form of claim 52, which exhibits a TGA thermogram substantially as depicted in FIG. 25.

58. The solid form of claim 8, having Form X.

59. The solid form of claim 58, having at least two characteristic XRPD peaks selected from about 4.4, about 6.6, about 8.2, about 8.8, about 12.9, about 16.3, about 21.4, about 22.4, about 23.3, and about 25.8 degrees 2-theta.

60. The solid form of claim 58, having an XRPD pattern with characteristic peaks as substantially shown in FIG. 26.

61. The solid form of claim 8, having Form XI.

62. The solid form of claim 61, having at least two characteristic XRPD peaks selected from about 8.2, about 9.8, about 13.5, about 16.1, about 18.0, about 18.9, about 19.7, about 20.5, about 22.7, and about 23.6 degrees 2-theta.

63. The solid form of claim 61, having an XRPD pattern with characteristic peaks as substantially shown in FIG. 27.

64. The solid form of claim 61, which exhibits a DSC thermogram having an endotherm peak at a temperature of about 208° C.

65. The solid form of claim 61, which exhibits a DSC thermogram substantially as depicted in FIG. 28.

66. The solid form of claim 61, which exhibits a TGA thermogram substantially as depicted in FIG. 29.

67. A pharmaceutical composition comprising a solid form of claim 8, and one or more pharmaceutically acceptable carriers or excipients.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15
```